(12) United States Patent
Edwards, Jr. et al.

(10) Patent No.: US 9,364,539 B2
(45) Date of Patent: *Jun. 14, 2016

(54) PHARMACEUTICAL COMPOSITIONS AND METHODS TO VACCINATE AGAINST CANDIDIASIS

(71) Applicant: Los Angeles Biomedical Research Institute at Harbor-UCLA Medical Center, Torrance, CA (US)

(72) Inventors: John E. Edwards, Jr., Palos Verdes Estates, CA (US); Scott G. Filler, Rancho Palos Verdes, CA (US); Donald C. Sheppard, Montreal (CA); Ashraf S. Ibrahim, Irvine, CA (US); Yue Fu, Carson, CA (US); Brad J. Spellberg, Rancho Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/034,300

(22) Filed: Sep. 23, 2013

(65) Prior Publication Data

US 2014/0127243 A1    May 8, 2014

Related U.S. Application Data

(62) Division of application No. 10/245,802, filed on Sep. 13, 2002, now Pat. No. 8,541,008.

(51) Int. Cl.
| | |
|---|---|
| A61K 39/00 | (2006.01) |
| C07K 14/40 | (2006.01) |
| C07K 16/14 | (2006.01) |
| A61K 45/06 | (2006.01) |
| A61K 39/395 | (2006.01) |
| A61K 38/16 | (2006.01) |

(52) U.S. Cl.
CPC ............. *A61K 45/06* (2013.01); *A61K 38/16* (2013.01); *A61K 39/0002* (2013.01); *A61K 39/39575* (2013.01); *C07K 14/40* (2013.01); *C07K 16/14* (2013.01); *A61K 2039/505* (2013.01); *A61K 2039/53* (2013.01)

(58) Field of Classification Search
None
See application file for complete search history.

(56) References Cited

U.S. PATENT DOCUMENTS

| 6,248,329 B1 * | 6/2001 | Chandrashekar et al. . 424/191.1 |
| 8,541,008 B2 * | 9/2013 | Edwards et al. ........... 424/274.1 |
| 2012/0014995 A1 * | 1/2012 | Edwards et al. ........... 424/274.1 |

OTHER PUBLICATIONS

Spellberg et al. J. Infect. Dis. 194: 256-260, Jul. 15, 2006.*
Spellberg et al. Infect. Immun. 76: 4574-4580, Oct. 2008.*
Ellis RW. Vaccines, (Eds) Plotkin et al., W.B. Saunders Company, Philadelphia, Chapter 29, 568-575, 1988.*
Sheppard DC et al. J. Biol. Chem. 279: 30480-30489, Jul. 2004.*
Hoyer et al. Mol. Microbiol. 15: 39-54, Jan. 1995.*
Hoyer. Trends in Microbiology 9: 176-180, Apr. 2001.*
Greenspan et al. Nature Biotechnology 7: 936-937, 1999.*
Fu et al. Mol. Microbiol. 44: 61-72, Apr. 2002.*
Hoyer et al. Genetics 157: 1555-1567, Apr. 2001.*
Hoyer et al. J. Bacteriol. 180: 5334-5343, Oct. 1998.*
Hoyer et al. Infect. Immun. 67: 4251-4255, Aug. 1999.*

* cited by examiner

*Primary Examiner* — S. Devi
(74) *Attorney, Agent, or Firm* — Clark & Elbing LLP

(57) ABSTRACT

A *Candida albicans* bloodstream infections cause significant morbidity and mortality in hospitalized patients. Filament formation and adherence to host cells are critical virulence factors of *C. albicans*. Multiple filamentation regulatory pathways have been discovered, however the downstream effectors of these regulatory pathways remain unknown. The cell surface proteins in the ALS group are downstream effectors of the filamentation regulatory pathway. Particularly, Als1p mediates adherence to endothelial cells in vitro and is required for virulence. The blocking of adherence by the organism is described resulting from the use of a composition and method disclosed herein. Specifically, a pharmaceutical composition comprised of a gene, gene product, or specific antibody to the ALS gene family is administered as a vaccine to generate an immune response capable of blocking adherence of the organism.

9 Claims, 11 Drawing Sheets

A

B

Wild-Type    $P_{ADH1}$-ALS1

B

*efg1/efg1*  *efg1/efg1*, $P_{ADH1}$ *ALS1*

B a

Wild-Type  　　　　als1/als1　　　　als1/als1::ALS1 b

Wild-Type  　　　　als1/als1　　　　als1/als1::ALS1

Figure 7

PHARMACEUTICAL COMPOSITIONS AND METHODS TO VACCINATE AGAINST CANDIDIASIS

RELATED INFORMATION

This application is a divisional application of U.S. Ser. No. 10/245,802, filed Sep. 13, 2002, now U.S. Pat. No. 8,541,008. The priority of the prior application is expressly claimed, and the disclosure of the prior application is hereby incorporated in its entirety.

STATEMENT AS TO FEDERALLY SPONSORED RESEARCH

This invention was made with Government support under Public Health Service grants PO-1Al-37194, RO1A1-19990, and MO1 RR0425. The Government has certain rights in this invention.

FIELD OF INVENTION

This invention relates to *Candida albicans* surface adhesin proteins, to antibodies resulting from an immune response to vaccination, to compositions used as prophylactic or therapeutic vaccines, and to methods for the prevention and/or treatment of candidiasis.

BACKGROUND OF INVENTION

A dramatic increase in the incidence of nosocomial infections caused by *Candida* species has been observed in recent years. The incidence of hematogenously disseminated candidal infections increased 11-fold from 1980 to 1989. This increasing incidence has continued through the 1990s and into the 2000s. Infections by *Candida* species are now the fourth most common cause of nosocomial septicemia, are equal to that of *Escherichia coli*, and surpass the incidence caused by *Klebsiella* species. Furthermore, *Candida* species are the most common cause of deep-seated fungal infections in patients who have extensive burns. Up to 11% of individuals undergoing bone marrow transplantation and 13% of those having an orthotopic liver transplant will develop an invasive candidal infection.

*C. albicans* infections are difficult to diagnose and the organism can survive in vivo without causing overtly detectable disease symptoms and can cause overt disease symptoms that vary in site and in severity. The infection can be localized and superficial or systemic and disseminated. *C. albicans* possesses numerous mechanisms to adapt to host sites, and differential gene expression under these mechanisms. *Candida albicans* can switch between two morphologies: the blastospore (budding yeast) and filamentous (hyphae and pseudohyphae) phases. *Candida* mutants that are defective in genes regulating filamentation are reported to have reduced virulence in animal models. This reduced virulence suggests that the ability to change from a blastospore to a filament is a key virulence factor of *C. albicans*. To date, no essential effectors of these filamentation pathways have been identified in *C. albicans*. See Caesar-TonThat, T. C. and J. E. Cutler, "A monoclonal antibody to Candida albicans enhances mouse neutrophil candidacidal activity," Infect. Immun. 65:5354-5357, 1997.

The identification of effectors in the regulatory pathways of the organism that contribute to virulence offers the opportunity for therapeutic intervention with methods or compositions that are superior to existing antifungal agents. The identification of cell surface proteins that effect a regulatory pathway involved in virulence is particularly promising because characterization of the proteins enables immunotherapeutic techniques that are superior to existing antifungal agents when fighting a candidal infection. Also, both passive and active vaccination techniques offer unique prophylactic or therapeutic utilities depending on the clinical setting.

While potent antifungal agents exist that are microbicidal for *Candida*, the attributable mortality of candidemia is approximately 38%, even with treatment with potent antifungal agents such as amphotericin B. Also, existing agents such as amphotericin B tend to exhibit undesirable toxicity. Although additional antifungals may be developed that are less toxic than amphotericin B, it is unlikely that agents will be developed that are more potent. Therefore, either passive or active immunotherapy to treat or prevent disseminated candidiasis is a promising alternative to standard antifungal therapy.

The virulence of *Candida albicans* is regulated by several putative virulence factors, of which adherence to host constituents and the ability to transform from yeast-to-hyphae are among the most critical in determining pathogenicity. Adherent strains of *C. albicans* are more virulent than less-adhesive strains. Moreover, the more frequently isolated pathogenic species exhibit greater adhesive capacity. Investigations to understand *C. albicans* adhesion have involved characterization of the cell surface, since this is the initial point of contact between fungus and host. Moreover, filmentation pathways and their effect on molecules and pathways are implicated in virulence.

SUMMARY OF INVENTION

The present invention utilizes the gene, the family of gene products, a specific anisera of *C. albicans* agglutinin like sequence as a vaccine to treat, prevent, or alleviate disseminated candidiasis. The invention includes specially formulated compositions containing the ALS1a polynucleotides, the ALS1a polypeptides, monoclonal and polyclonal antisera specifically reactive with these molecules and compositions containing forms or derivatives of any of the foregoing molecules such as fragments or truncations. All of the compositions and methods of the invention take advantage of the role of the group of the ALS1 gene products in the adherence of the *C. albicans* to endothelial and epithelial cells and the role of ALS expression in adherence and filamentation and in the overall virulence of *C. Albicans*. Specifically, the control of ALS1 expression by transcription factor Efg1p, which is known to be a regulation of filamentation, demonstrates the susceptibility of the ALS1-expressed surface protein for use in therapeutic strategies, e.g. for use of the polypeptide as a vaccine to retard the pathogenesis of the organism, for use of antisera (polyclonal or monoclonal antibodies) in a passive immunization strategy, or for immunization by polynucleotide vaccination.

Pursuant to this invention, a member of the ALS gene family encodes a surface adhesin that is selected as the target of an immunotherapeutic strategy against *Candida albicans*. A demonstration that an expression product of an ALS gene has structural characteristics typical of surface proteins and is, in fact, expressed on the cell surface of *C. albicans* is a critical first criterion for any member of the group of proteins that acts as an adhesin to host tissues. For example, ALS1p has a signal peptide at the N-terminus, a glycosylphosphatidylinosine (GPI) anchorage sequence in the C-terminus, and a central region comprising repeats rich in threonine and serin. N—, and O— as well as several glycosylation sites, which is typical of proteins that are expressed on the cell surface. Indirect immunofluorescence using a monoclonal antibody directed against the N-terminus of Als1p revealed that Als1p is expressed during the log phase of blastospores. This expression of Als1p is increased during hyphal formation and is localized to the junction where the hyphal element extends from the blastospores as indicated by the diffused surface staining. Furthermore, a monoclonal antibody blocked the enhanced adherence of *C. albicans* overexpression mutant to endothelial cells, thereby establishing the principle for immunotherapy applications using members of the ALS family. The N-terminal region is a prime candidate for both passive and active immunization strategies and the gene and gene product can be used in a full length, truncated or modified form.

Additional evidence that ALS1p is a surface adhesin protein is based on data showing that antibodies that bind to the surface of *C. albicans* also bind to the surface of *S. cerevisiae* transformed with ALS1, but not with empty plasmid. The ALS1 protein also shares significant homology with the alpha-agglutinin of *S. cerevisiae*, which is expressed on the cell surface and mediates the binding of mating type alpha cells to mating type a cells. Moreover, expression of the ALS1 gene in *S. cerevisiae* increases the adherence of this organism to endothelial cells by approximately 100-fold. Because the ALS1 gene appears to encode a functional adhesin in Saccharomyes cerevisiae, it is certain that it also encodes a functional adhesin in *C. albicans*. The ALS1 gene was originally isolated by Hoyer et al. without a known function. Hoyer, L. L., S. Scherer, A. R. Shatzman, and G. P. Livi. 1995. *Candida albicans* ALM1: domains related to a *Saccharonzyces cerevisiae* sexual agglutinin separated the direct role of ALS1p in the various virulence pathways described herein, e.g. adherence, filamentation, and floculation satisfy a second criteria for use as a therapeutic agent, and lead to the therapeutic embodiments of the invention as described in greater detail below. Recognition of the unique characteristics of the ALS1 gene product in the pathogenesis of the organism suggests several discrete therapeutic approaches that interrupt critical virulence factors or pathways by a repeating motif. Mol. Microbiol. 15:39-54. (See also U.S. Pat. Nos. 5,668,263 and 5,817,466.)

In addition to the administration of anti-fungal agents, immunotherapeutic therapies enabled by the invention are employed to fight a fungal infection as part of an integrated anti-fungal clinical strategy that combines traditional anti-fungal agents with immunotherapeutics. Immunotherapeutics can be broadly defined in two categories: active and passive. Active immunotherapy relies on the administration of an antigenic compound as a vaccine that causes the body's immune system to mount an immune response to the compound. Typically, the immune response includes cell-mediated immune pathways and the generation of antibodies against the antigenic compound. In active immunization, antibodies specific for the compound and generated by the body also fight the fungal infection. Passive immunotherapy involves direct administration of the antibodies without the antigen. In passive immunization, the antibodies may be generated in vitro, such as in a conventional hybridoma or other expression system, and are administered directly to a patient. Both active and passive immunization offer the advantage of using antibodies that are highly specific and typically far less toxic than ordinary anti-fungal agents.

Although certain data and results presented herein are specific to the ALS1 species and related compounds, additional members of the ALS family exhibit similar functionality in the pertinent virulence pathways of *Candida*. The other members of the family, generally designated as ALS1-ALS1a share significant sequence homology with ALS1 and with each other and show highly conserved regions N terminal region. See FIG. 7. Thus, according to one aspect of the invention, a member of the ALS surface adhesin family of proteins or a fragment, conjugate, or analogue thereof, is formulated in a pharmaceutical composition and administered as a vaccine. ALS surface adhesin proteins are preferably obtained from *Candida albicans*, however, similar adhesin molecules or analogues or derivatives thereof may be of candidal origin and may be obtainable from strains belonging to the genera *Candida* such as *Candida parapsilosis*, *Candida guilliermondii*, *Candida krusei*, *Candida dubinoensis*, and *Candida tropicalis*. A surface adhesin protein according to the invention may be obtained in purified form, and thus, according to a preferred embodiment of the invention, a substantially pure ALS *Candida albicans* surface adhesin protein, or functional analogue, conjugate, or derivative thereof, is formulated as a vaccine to cause an immune response in a patient to block adhesion of the organism to the endothelial cells.

An analogue or derivative of the surface adhesion protein according to the invention may be identified and further characterized by the criteria described herein for the ALS gene and gene product. For example, a null mutant of the analogue or derivative would share markedly reduced adhesion to endothelial cells compared to controls. Similarly, over-expression of the analogue or derivative in an appropriate model would show an increased adherence to endothelial cells compared to controls and would be confirmed as a cell surface adhesin in accord with the criteria described above. Also, antisera to the analogue or derivative would cross-react with anti-ALS antibodies and would also exhibit increased survival times when administered in animal models of disseminated candidiasis as disclosed herein.

The present invention also provides an immunotherapeutic strategy against *Candida* infection at the level of binding to the vascular endothelial cells and through a downstream effector of the filamentation regulatory pathway. An immunotherapeutic strategy is uniquely advantageous in this context because: (i) the morbidity and mortality associated with hematogenously disseminated candidiasis remains unacceptably high, even with currently available antifungal therapy; (ii) a rising incidence of antifungal resistance is associated with the increasing use of antifungal agents, (iii) the population of patients at risk for serious *Candida* infections is well-defined and very large, and includes post-operative patients, transplant patients, cancer patients and low birth weight infants; and (iv) a high percentage of the patients who develop serious *Candida* infections are not neutropenic, and thus may respond to a vaccine. For these reasons, *Candida* is the most attractive fungal target for either passive or active immunotherapy.

Having determined the immunotherapeutic potential of members of the ALS family according to this invention, the gene, the protein gene product, conjugates, analogues, or derivative molecules thereof, and compositions containing specific monoclonal or polyclonal antisera may be used in treatment and/or prevention of candidal infections. Standard immunological techniques may be employed with the adhesion protein molecule, and its analogues, conjugates, or derivatives, to use the molecule as an immunogen in a pharmaceutically acceptable composition administered as a vaccine. For the purposes of this invention, "pharmaceutical" or "pharmaceutically acceptable" compositions are formulated by known techniques to be non-toxic and, when desired, used with carriers or additives that are approved for administration to humans in, for example, intravenous, intramuscular, intraperitoneal or sub-cutaneous injection. Such compositions may include buffers, salts or other solvents known to these skilled in the art to preserve the activity of the vaccine in solution.

With respect to the molecule used as the immunogen pursuant to the present invention, those of skill in the art will recognize that each protein molecule within the ALS family may be truncated or fragmented without losing the essential qualities as a vaccine. For example, the Als1p may be truncated to yield an N-terminal fragment by truncation from the C-terminal end with preservation of the functional properties described above and may include all or a portion of the GP1 anchor sequences on the central region. Likewise, C-terminal fragments may be created by truncation from the N-terminal end with preservation of the functional properties described above. Other modifications in accord with the foregoing rationale may be made pursuant to this invention to create other ALS protein analogs or derivatives, to achieve the benefits described herein with the native protein.

The goal of the immunotherapy provided by this invention is to interfere with regulation of filamentation, to block adherence of the organism to host constituents, and to enhance clearance of the organism by immunoeffector cells. Since endothelial cells cover the majority of the vasculature, specially selected strategies, compositions, and formulations to block the adherence of the organism to endothelial cells using antibodies are a preferred embodiment of the present invention and such adherence blocking strategies include active or passive immunotherapy directed against the candidal adhesin(s) disclosed herein. Specific anti-sera having demonstrated abilities to interrupt virulence factors and pathways implicated in virulence are identified herein based on the identification of the unique properties of the ALS family of proteins and specific derivatives thereof, including N-terminal fragments of the ALS proteins, specific monoclonal and polyclonal antisera against regions of the protein molecule, and polynucleotides selectively encoding this region.

Depending on the specific virulence of a strain in a clinical setting, a pharmaceutical composition comprising either monoclonal or polyclonal antibodies may be administered in a passive immunization therapy. Polyclonal antibodies are thought to involve fewer specific cross reactivity reactions that may lead to acute toxicity, whereas monoclonal antibodies provide more reproducible binding to a specific epitope of a target protein. Therefore, selection of the species for passive immunotherapy depends on the specific organism encoding the protein-antigen, as well as the specific antibody raised against the ALS protein. In either case, the antisera is specific to a portion of the ALS protein and functions to interrupt virulence regulatory pathways necessary for pathogenesis of the organism. Specifically, the antisera affects the Efg1p filamentation pathway and expression of the surface protein implicated in both floculation and adherence to endothelial cells. Characteristic antisera of the invention interrupt the role of ALS in filamentation and virulence mechanisms in both in vitro systems as well as animal models of disseminated candidiasis.

The method of the invention also includes ameliorating and/or preventing candidal infection by blocking the adherence of *C. albicans* to the endothelial cells of a host constituent. Thus, according to one aspect of the invention, a pharmaceutical composition comprising an ALS adhesin protein derivative, analogue, or conjugate is formulated as a vaccine in a pharmaceutical composition containing a biocompatible carrier for injection or infusion and is administered to a patient. Prior to injection, the adhesin protein may be formulated as a vaccine in a suitable vehicle, preferably a known immunostimulant such as a polysaccharide. Thus, according to a further aspect of the invention we provide a pharmaceutical composition comprising a candidal adhesin protein together with one or more pharmaceutically acceptable excipients in a formulation for use as a vaccine. Also, direct administration of antiserum raised against an ALS protein may be used as a therapeutic or prophylactic strategy to block the adherence of *C. albicans* to a mammalian host constituent. Thus, for example, any suitable host may be injected with protein and the serum collected to yield the desired antiadhesin antibody after appropriate purification and/or concentration. Monoclonal antiserum against adhesin protein can be obtained by known techniques, Kohler and Milstein, Nature 256: 495-499 (1975), and may be humanized to reduce antigenicity, see U.S. Pat. No. 5,693,762, or produced by immunization of transgenic mice having an unrearranged human immunoglobulin gene, see U.S. Pat. No. 5,877,397, to yield high affinity (e.g. $10^8$, $10^9$, or $10^{19}$) anti-ALS IgG monoclonal antibodies.

A still further use of the invention, for example, is using an ALS adhesin protein to develop a specific clinical vaccine strategies for the prevention and/or amelioration of candidal infections. Thus, according to one aspect of the invention, for example, standard immunology techniques may be employed to construct a multi-protein or protein fragment component vaccine strategy that may enhance and/or elicit immune response from a host constituent to bock adherence of *C. albicans*. Also, known immunostimulatory compositions may be added to the vaccine formulation, wherein such compounds include known proteins, saccharides or oligonucleotides. (See Krieg U.S. Pat. No. 6,008,200).

A still further use of the invention, for example, is an isolated polynucleotide, RNA or DNA vaccine strategy wherein the ALS polynucleotide encoding an ALS protein or a fragment or variant thereof is administered according to a protocol designed to yield an immune response to the gene product. See e.g., Felgner U.S. Pat. No. 5,703,055. Generally, the naked polynucleotide is combined in a pharmaceutically acceptable injectable carrier and injected into muscle tissue where the polynucleotide is transported into cells and expressed to produce a selectively induced immunogenic response comprised of antibodies against the polypeptide encoded by the polynucleotide. The tissue into which the polynucleotide is introduced is preferably muscle, but can be any tissue that expresses the polynucleotide. The polynucleotide may be either a DNA or an RNA sequence and when the DNA is used, the DNA sequence can be inserted into a plasmid that also contains a replicator. In this embodiment, a method of immunization is provided by obtaining an expressible polynucleotide coding for an immunogenic ALS polypeptide, and introducing the polynucleotide into a patient to elicit expression of the ALS polypeptide and the generation of an immune response against the immunogen such that an anti-ALS antibody composition produced in vivo provides protection against Candidiasis by disrupting the virulence pathway, for example, as has been associated with ALS1p and the effector pathway for adhesion and filamentation of the *Candida* organism. Particularly preferred polynucleotide compositions encode N-terminal regions of an ALS polypeptide and code for the specific regions that elicit the antisera production in vivo that are shown herein to exhibit the prophylactic therapeutic utility derived from interruption of *Candida* virulence mechanisms.

A still further use of the invention, for example, is developing combination vaccine strategies. Thus, according to one aspect of the invention, for example, anti-ALS antibodies may be used with antibodies in treating and/or preventing candidal infections. See U.S. Pat. No. 5,578,309.

DESCRIPTION OF THE FIGURES

Figure 7:
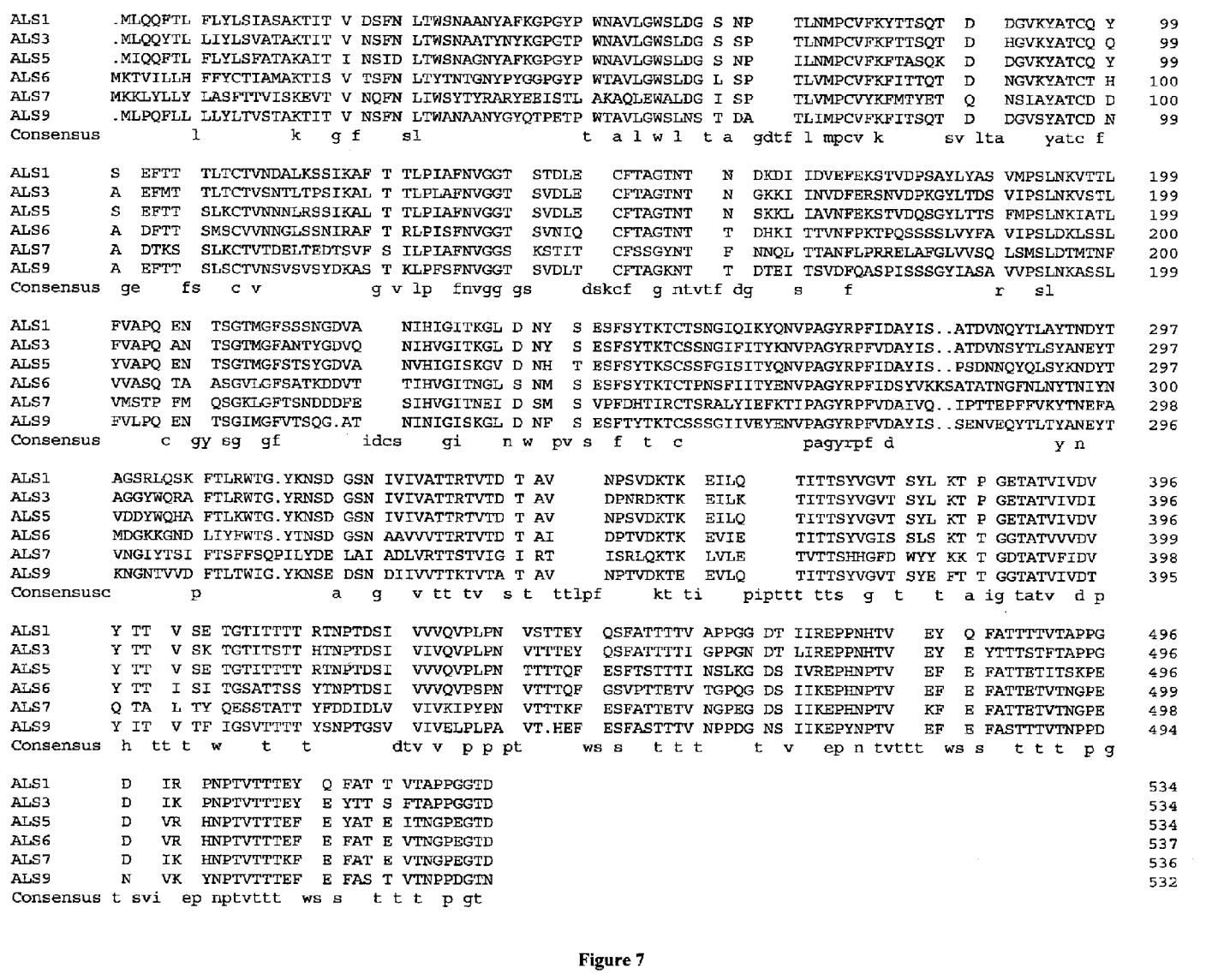

FIG. 7 is the protein sequence alignment of the N-terminal portion of select ALS proteins arranged by adherence phenotype. The top three lines are the sequences from ALS proteins that bind endothelial cells: ALS1 (SEQ ID NO: 25), ALS3 (SEQ ID NO: 26), and ALS 5 (SEQ ID NO: 27), and the bottom three sequences from ALS proteins that do not bind endothelial cells: ALS6 (SEQ ID NO: 28), ALS 7 (SEQ ID NO: 29), and ALS 9 (SEQ ID NO: 30). The line labeled "Consensus" includes the following amino acid sequences "gdtf" (SEQ ID NO: 31); "mpcv" (SEQ ID NO: 32); "yatc" (SEQ ID NO: 33); "fnvgg" (SEQ ID NO: 34); "dskcf" (SEQ ID NO: 35); "ntvtf" (SEQ ID NO: 36); "idcs" (SEQ ID NO: 37); "pagyrpf" (SEQ ID NO: 38); "ttlpf" (SEQ ID NO: 39); "pipttt" (SEQ ID NO: 40); "tatv" (SEQ ID NO: 41); "tvttt" (SEQ ID NO: 42); and "nptvttt" (SEQ ID NO: 43).

DETAILED DESCRIPTION OF THE INVENTION

Figure 1A:
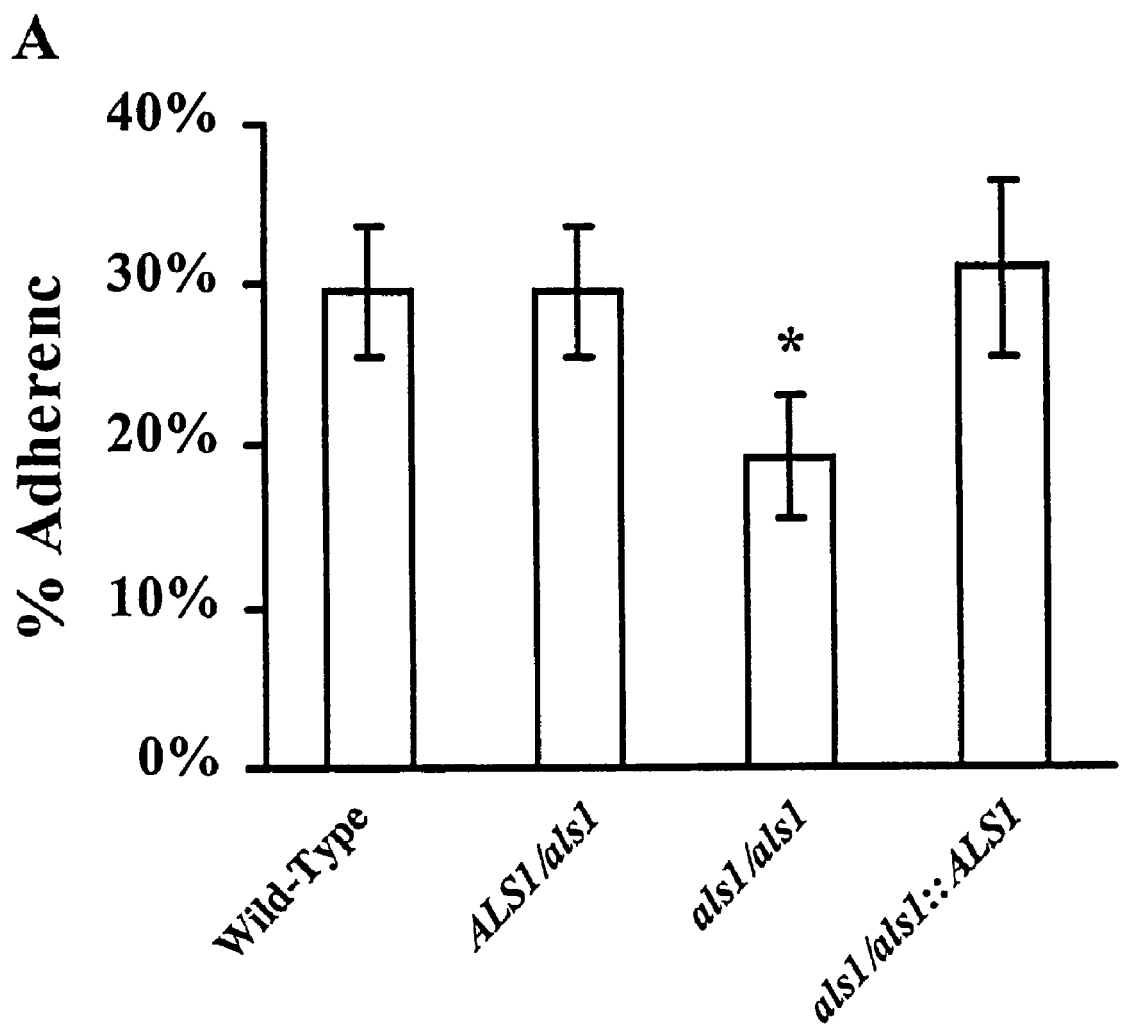
FIGS. 1A, 1B show the mediation of Als1p adherence of *C. albicans* to human umbilical vein endothelial cells. Values represent the mean±SD of at least three independent experiments, each performed in triplicate. (A) Endothelial cell adherence of ALS1/als2, als1/als1 and ALS1-complemented mutants and wild-type CAI12 (30) (B) Endothelial cell adherence of $P_{ADH1}$-ALS1 mutant that overexpresses ALS1, compared to wild type *C. albicans*. Statistical treatment was obtained by Wilcoxon rank sum test and corrected for multiple comparisons with the Bonferroni correction. *P<0.001 for all comparisons.

The nature of the pathogenesis of *C. albicans* by adherence to endothelial cells is discussed in U.S. Pat. No. 5,578,309 which is specifically incorporated herein by reference in its entirety. For a description of the ALS1 gene and characteristics thereof, including the characterization of the gene product as an adhesin, see Fu, Y., S. G. Filler, B. J. Spellberg, W. Fonzi, A. S. Ibrahim, T. Kanbe, M. A. Ghannoum, and J. E. J. Edwards. 1998. Cloning and characterization of CAD I/AAF1, a gene from *Candida albicans* that induces adherence to endothelial cells after expression in *Saccharonzyces cerevisiae*. Infect. Immun. 66:2078-2084; Fu, Y., G. Rieg, W. A. Forizi, P. H. Belanger, J. E. J. Edwards, and S. G. Filler. 1998. Expression of the *Candida albicans* gene ALS1 in *Saccharomyces cerevisiae* induces adherence to endothelial and epithelial cells. Infect. Immun. 66:1783-1786; Hoyer, L. L. 1997. The ALS gene family of *Candida albicans*. International Society for Human and Animal Mycology Salsimorge, Italy: (Abstract); Hoyer, L. L., S. Scherer, A. R. Shatzman, and G. P. Livi. 1995. *Candida albicans* ALS1: domains related to a *Saccharonzyces cerevisiae* sexual agglutinin separated by a repeating motif. Mol. Microbiol. 15:39-54. The polynucleotide sequence of the ALS1 gene and protein are SEQ ID NO:7 and NO:8, respectively. The remaining numbers of the ALS family of gene and protein ALS-2-ALS-9, are SEQ ID NO:9-SEQ ID. NO:24. Note that the form sometimes known as ALS-N is ALS-9 and ALA-1 is ALS-5.

The following Examples illustrate the immunotherapeutic utility of the class of ALS protein molecules as the basis for prevention or treatment of disseminated candidiasis. Example 1 describes the preparation of an ALS1 null mutant and a strain of *C. albicans* characterized by over-expression of ALS1 to confirm the mediation of adherence to endothelial cells. Example 2 describes the localization of Als1p and the implication of the efg filamentation regulatory pathway. Example 3 describes the purification of ALS1 adhesin protein. Example 4 describes the preparation of antibodies raised against the ALS1 surface adhesin protein to be used to demonstrate the blocking of the surface adhesin protein. Example 5, describes the blocking of adherence in vivo, using both polyclonal and monoclonal antibodies raised against the ALS1 surface adhesion protein as described herein to protect against disseminated candidiasis in a mouse model. Example 6 describes a polynucleotide vaccination strategy to cause in vivo expression of an antigenic ALS1p polypeptide to create a protective immune response.

Although any methods and materials similar or equivalent to those described herein can be used in the practice or testing of the present invention, preferred methods and materials are described. As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "gene" typically refers to a large number of polynucleotides that form a single functional unit that is translated and transcribed to express a polypeptide of sufficient length to be immunogenic.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Antibody" or "antisera" refers to a polypeptide substantially encoded by an immunoglobulin gene or immunoglobulin genes, or fragments thereof, which specifically bind and recognize an immunogen. The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'.sub.2 fragments. The term "antibody," as used herein, also includes antibody fragments either produced by the modification of whole antibodies or those synthesized de novo using recombinant DNA methodologies.

An antibody "is specific" or "specifically binds" to a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

"Substantially pure" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective" or phamaceutically effective" amount refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

A "prophylactic" treatment is a treatment administered to a subject who does not exhibit overt symptoms or signs of a disease or exhibits only early signs for the purpose of decreasing the risk of developing pathology.

A "therapeutic" treatment is a treatment administered to a subject who exhibits signs of pathology for the purpose of diminishing or eliminating those signs.

Example 1

Als1 Mediates Adherence of *C. albicans* to Endothelial Cells

The URA blaster technique was used to construct a null mutant of *C. albicans* that lacks expression of the Als1p. The als1/als1 mutant was constructed in *C. albicans* strain CAI4 using a modification of the Ura-blaster methodology [W. A. Fonzi and M. Y. Irwin, *Genetics* 134, 717 (1993)] as follows: Two separate als1-hisG-IRA3-hisG-als1 constructs were utilized to disrupt the two different alleles of the gene. A 4.9 kb ALS1 coding sequence was generated with high fidelity PCR (Boehringer Mannheim, Indianapolis, Ind.) using the primers: 5'-CCGCTCGAGATGCTTCAACAATTTACAT-TGTTA-3' (SEQ ID NO. 1) and 5'-CCGCTCGAGTCAC-TAAATGAACAAGGACAATA3' (SEQ ID NO. 2). Next, the PCR fragment was cloned into pGEM-T vector (Promega, Madison, Wis.), thus obtaining pGEM-T-ALS1. The hisG-URA3-hisG construct was released from pMG-7 by digestion with KpnI and Hind3 and used to replace the portion of ALS1 released by Kpn1 and Hind3 digestion of pGEM-T-ALS1. The final als1-hisG-URA3-hisG-als1 construct was released from the plasmid by digestion with XhoI and used to disrupt the first allele of ALS1 by transformation of strain CAI-4.

A second als1-hisG-URA3-hisG-als1 construct was generated in two steps. First, a Bgl2-Hind3 hisG-URA3-hisG fragment of pMB7 was cloned into the Bam1H-Hind3 sites of pUC19, thereby generating pYC2. PYC2 was then digested with Hind3, partially filled in with dATP and dGTP using T4 DNA polymerase, and then digested with Sma1 to produce a new hisG-URA3-hisG fragment. Second, to generate ALS1 complementary flanking regions, pGEM-T-ALS1 was digested with XbaI and then partially filled in with dCTP and dTTP. This fragment was digested with HpaI to delete the central portion of ALS1 and then ligated to the hisG-URA3-hisG fragment generating pYC3. This plasmid was then digested by XhoI to release a construct that was used to disrupt the second allele of the ALS1. Growth curves were done throughout the experiment to ensure that the generated mutations had no effect on growth rates. All integrations were confirmed by Southern blot analysis using a 0.9 kb ALS1 specific probe generated by digestion of pYF5 with XbaI and HindIII.

The null mutant was compared to *C. albicans* CAI-12 (a URA+revertant strain) for its ability to adhere in vitro to human umbilical vein endothelial cells. For adherence studies, yeast cells from YPD (2% glucose, 2% peptone, and 1% yeast extract) overnight culture, were grown in RPMI with glutamine at 25° C. for 1 hour to induce Als1p expression. $3 \times 10^2$ organisms in Hanks balanced salt solution (HBSS) (Irvine Scientific, Irvine, Calif.) were added to each well of endothelial cells, after which the plate was incubated at 37° C. for 30 minutes. The inoculum size was confirmed by quantitative culturing in YPD agar. At the end of incubation period, the nonadherent organisms were aspirated and the endothelial cell monolayers were rinsed twice with HBSS in a standardized manner. The wells were over laid with YPD agar and the number of adherent organisms were determined by colony counting. Statistical treatment was obtained by Wilcoxon rank sum test and corrected for multiple comparisons with the Bonferroni correction. $P<0.001$.

Referring to FIG. 1, a comparison of the ALS1/ALS1 and als1/als1 strain showed that the ALS1 null mutant was 35% less adherent to endothelial cells than *C. albicans* CAI-12. To reduce background adherence, the adherence of the wild-type strain grown under non-ALS1 expressing conditions was compared with a mutant autonomously expressing Als1p. This mutant was constructed by integrating a third copy of ALS1 under the control of the constitutive ADH1 promoter into the wild-type *C. albicans*. To achieve constitutive expression of the ALS1 in *C. albicans*, a blunt-ended PCR generated URA3 gene is ligated into a blunt-edged Bgl2 site of pOCUS-2 vector (Novagen, Madison, Wis.), yielding pOU-2. A 2.4 kb Not1-Stul fragment, which contained *C. albicans* alcohol dehydrogenase gene (ADH1) promoter and terminator (isolated from pLH-ADHpt, and kindly provided by A. Brown, Aberdeen, UK), was cloned into pOU-2 after digestion with Not1 and Stul. The new plasmid, named pOAU-3 had only one Bgl2 site between the ADH1 promoter and terminator. ALS1 coding sequence flanked by BamH1 restriction enzyme sites was generated by high fidelity PCR using pYF-5 as a template and the following primers: 5'-CGGGATCCAGATGCTTCA-ACAATTTACATTG-3' (SEQ ID NO.3) and 5'-CGGGATCCTCACTAAATGAA-CAAGGACAATA-3' (SEQ ID NO.4). This PCR fragment was digested with BamH1 and then cloned into the compatible Bgl2 site of pOAU-3 to generate pAU-1. Finally, pAU-1 was linearized by XbaI prior to transforming *C. albicans* CAI-4. The site-directed integration was confirmed by Southern Blot analysis.

Figure 1B:
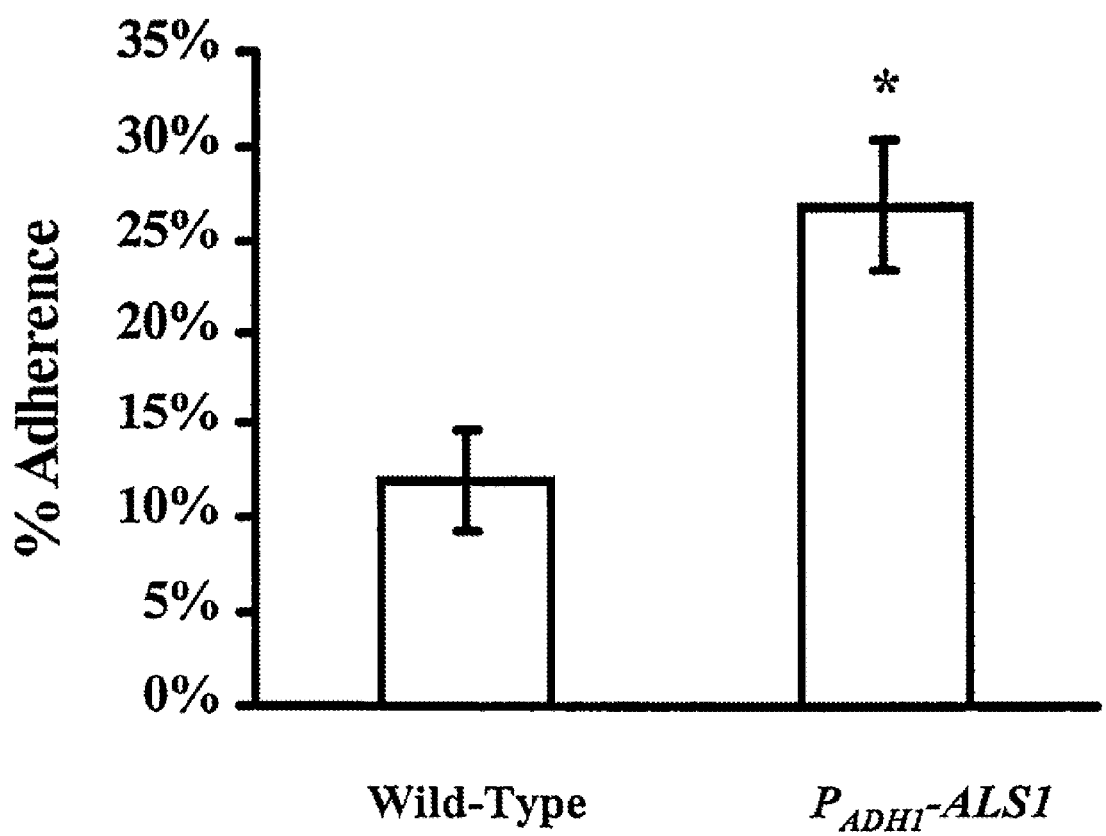

Referring to FIG. 1B, overexpressing ALS1 in this $P_{ADH1}$-ALS1 strain resulted in a 76% increase in adherence to endothelial cells, compared to the wild-type *C. albicans*. In comparing endothelial cell adherence of the wild-type to that of the overexpressing mutant, yeast cells were grown overnight in YPD at 25° C. (non-inducing condition of Als1p). Als1p expression was not induced to reduce the background adherence of the wild-type, thus magnifying the role of Als1p in adherence through $P_{ADH1}$-ALS1 hybrid gene. The adherence assay was carried out as described above. Statistical treatment was obtained by Wilcoxon rank sum test and corrected for multiple comparisons with the Bonferroni correction. $P<0.001$.

A monoclonal anti-Als1p murine IgG antibody was raised against a purified and truncated N-terminus of Als1p (amino acid #17 to #432) expressed using Clontech YEXpress™ Yeast Expression System (Palo Alto, Calif.). The adherence blocking capability of these monoclonal anti-Als1p antibodies was assessed by incubating *C. albicans*. cells with either anti-Als1 antibodies or mouse IgG (Sigma, St. Louis, Mo.) at a 1:50 dilution. After which the yeast cells were used in the adherence assay as described above. Statistical treatment was obtained by Wilcoxon rank sum test and corrected for multiple comparisons with the Bonferroni correction. $P<0.001$. The results revealed that the adherence of the $P_{ADH1}$-ALS1 strain was reduced from 26.8%±3.5% to 14.7%±5.3%. Thus, the effects of ALS1 deletion and overexpression demonstrate that Als1p mediates adherence of *C. albicans* to endothelial cells.

Example 2

Localization of Als1p

Figure 2A:
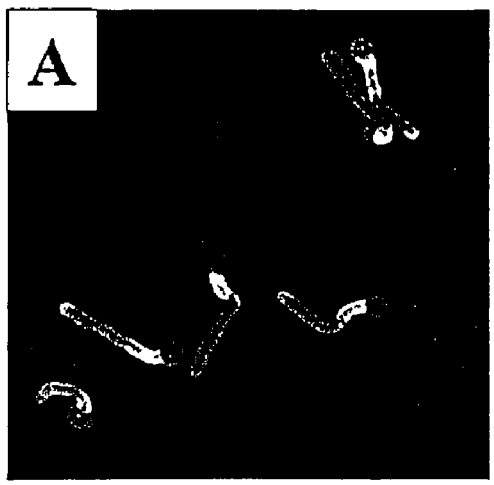
FIG. 2A-D shows the cell surface localization of Als1p on filaments of *C. albicans* by indirect immunofluorescence. Filamentation of *C. albicans* was induced by incubating yeast cells in RPMI 1640 medium with glutamine for 1.5 hours at 37° C. Als1p was detected by incubating organisms first with anti-Als1p mouse mAb followed by FITC-labeled goat anti-mouse IgG. *C. albicans* cell surface was also stained with anti-*C. albicans* polyclonal Ab conjugated with Alexa 594 (Molecular Probes, Eugene, Oreg.). Areas with yellow staining represent Als1p localization. (A) *C. albicans* wild-type. (B) als1/als1 mutant strain. (C) als1/als1 complemented with wild type ALS1 (D) $P_{ADH1}$-ALS1 overexpression mutant.
Figure 2B:
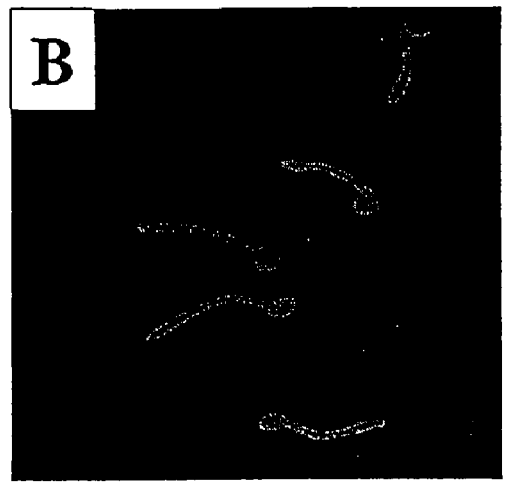
Figure 2C:
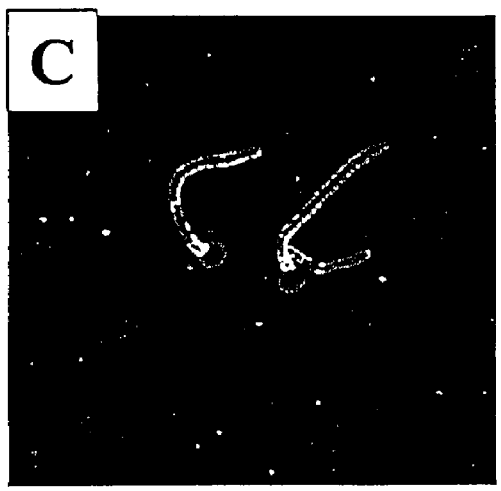
Figure 2D:
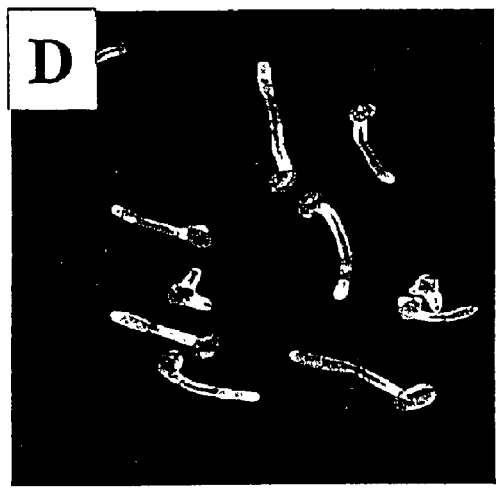

For a number of the ALS family to function as an adhesin protein, it must be located on the cell surface. The cell surface localization of Als1p, for example, was verified using indirect immunofluorescence with the anti-Als1p monoclonal antibody. Diffuse staining was detected on the surface of blastospores during exponential growth. This staining was undetectable on blastospores in the stationary phase. Referring to FIG. 2A, when blastospores were induced to produce filaments, intense staining was observed that localized exclusively to the base of the emerging filament. No immunofluorescence was observed with the als1/als1 mutant, confirming the specificity of this antibody for Als1p. See FIG. 2B. These results establish that Als1p is a cell surface protein.

Figure 3A:
FIGS. 3A, 3B show the mediation of Als1p on *C. albicans* filamentation on solid medium. *C. albicans* blastospores were spotted on Lee's agar plates and incubated at 37° C. for 4 days (A) or 3 days (B).
Figure 3B:
Figure 3B:
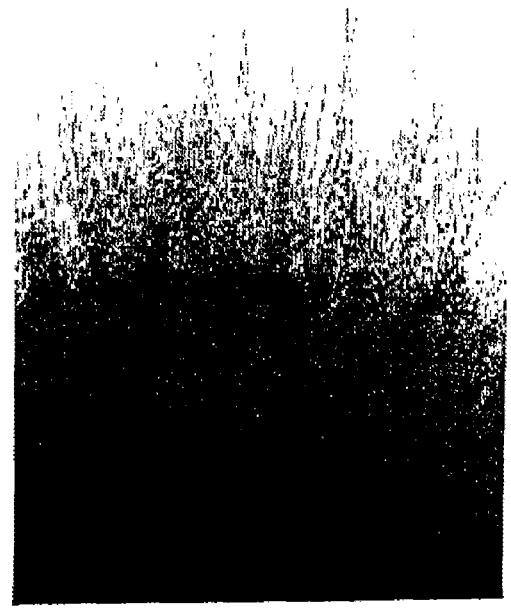
Figure 4A:
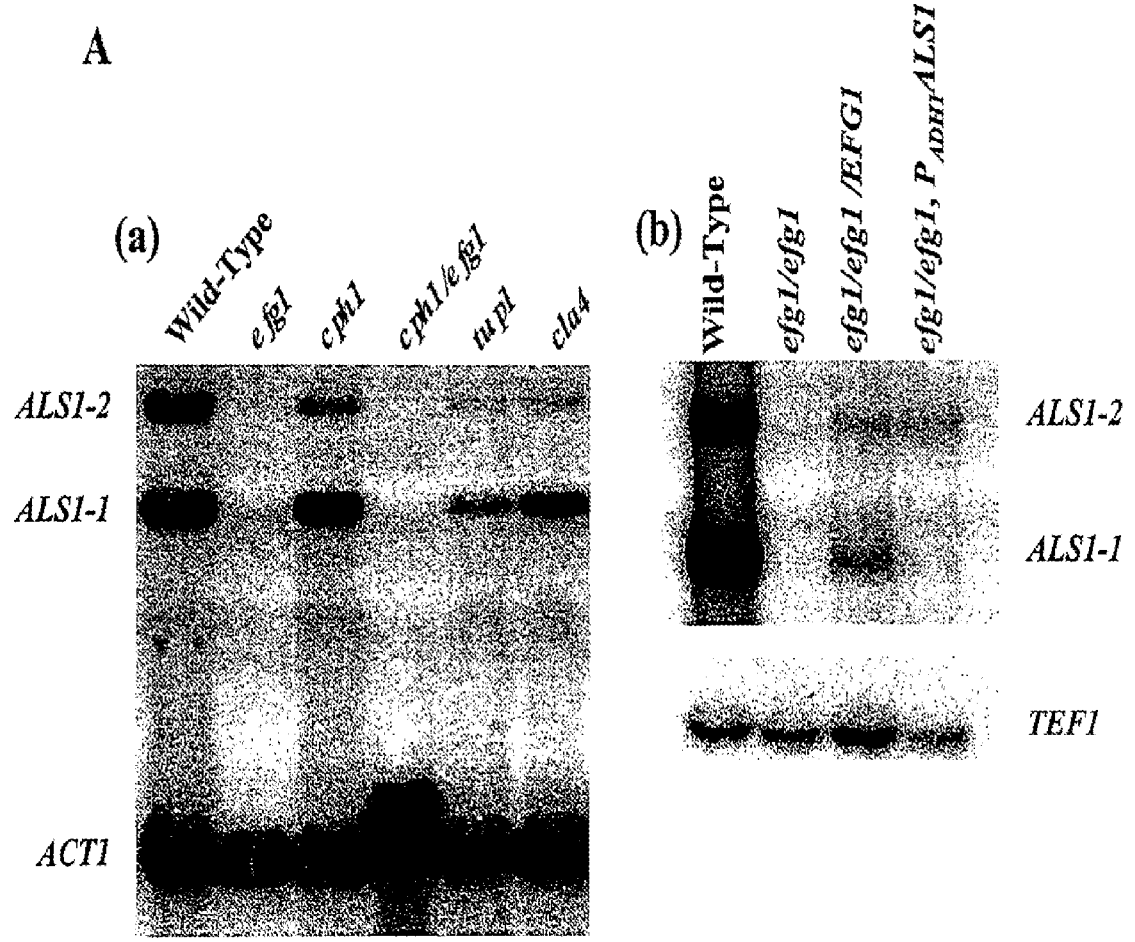
FIGS. 4A, 4B show the control of ALS1 expression and the mediation of *C. albicans* filamentation by the EFG1 filamentation regulatory pathway. (A) Northern blot analysis showing expression of ALS1 in (i) mutants deficient in different filamentation regulatory pathways. (ii) efg1/efg1 mutant complemented with either EFG1 or $P_{ADH1}$-ALS1. Total RNA was extracted from cells grown in RPM1 1640+ glutamine medium at 37° C. for 90 minutes to induce filamentation. Blots were probed with ALS1 and TEF1. (B) Photomicrographs of the efg1/efg1 mutant and efg1/efg1 mutant complemented with $P_{ADH1}$-ALS1 grown on Lee's agar plates at 37° C. for 4 days.
Figure 4B:
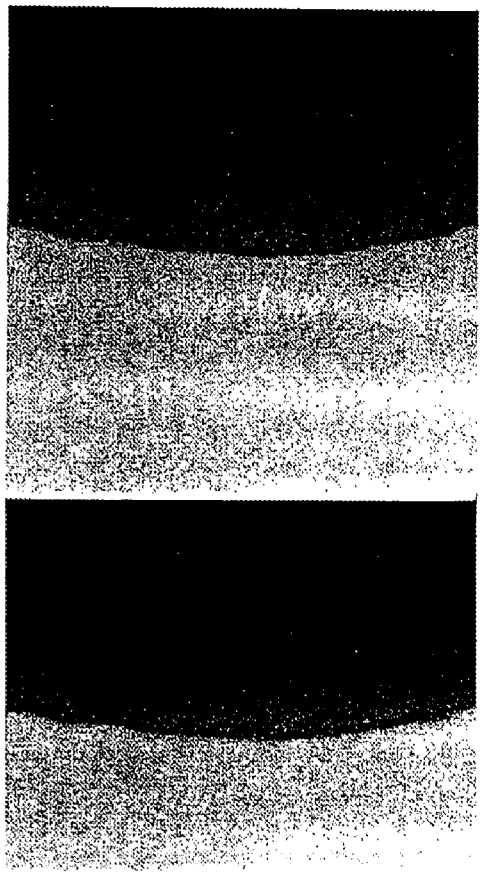
Figure 4B:
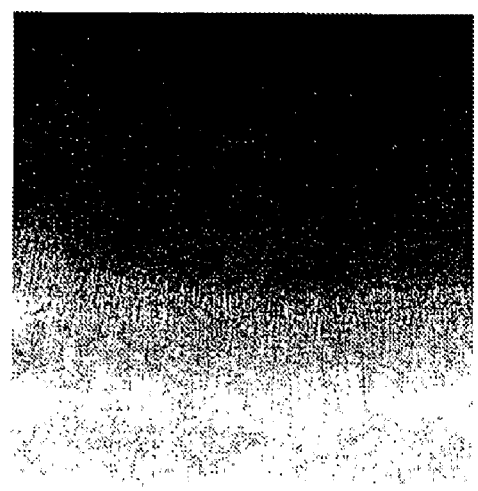

The specific localization of Als1p to the blastospore-filament junction implicates Als1p in the filamentation process. To determine the mechanism, the filamentation phenotype of the *C. albicans* ALS1 mutants was analyzed. Referring to FIG. 3A, the als1/als1 mutant failed to form filaments after a 4 day incubation on Lee's solid medium, while both the ALS1/ALS1 and ALS1/als1 strains as well as the ALS1-complemented mutant produced abundant filaments at this time point. The als1/als1 mutant was capable of forming filaments after longer periods of incubation. Furthermore, overexpressing ALS1 augmented filamentation: the $P_{ADH1}$-ALS1 strain formed profuse filaments after a 3 day incubation, whereas the wild-type strain produced scant filaments at this time point. See FIG. 3B. To further confirm the role of Als1p in filamentation, a negative control was provided using mutant similar to the ALS1 overexpression mutant, except the coding sequence of the ALS1 was inserted in the opposite orientation. The filamentation phenotype of the resulting strain was shown to be similar to that of the wild-type strain. The filament-inducing properties of Als1p are specific to cells grown on solid media, because all of the strains described above filamented comparably in liquid media. The data demonstrates that Als1p promotes filamentation and implicates ALS1 expression in the regulation of filamentation control pathways. Northern blot analysis of ALS1 expression in mutants with defects in each of these pathways, including efg1/efg1, cph1/cph1, efg1/efg cph1/cph1, tup1/tup1, and cla4/cla4 mutants were performed. Referring to FIG. 4A, mutants in which both alleles of EFG1 had been disrupted failed to express ALS1. Introduction of a copy of wild-type EFG1 into the efg1/efg1 mutant restored ALS1 expression, though at a reduced level. See FIG. 4B. Also, as seen in FIG. 4A, none of the other filamentation regulatory mutations significantly altered ALS1 expression (FIG. 4A). Thus, Efg1p is required for ALS1 expression.

If Efg1p stimulates the expression of ALS1, which in turn induces filamentation, the expression of ALS1 in the efg1/efg1 strain should restore filamentation. A functional allele of ALS1 under the control of the ADH1 promoter was integrated into the efg1/efg1 strain. To investigate the possibility that ALS1 gene product might complement the filamentation defect in efg1 null mutant, an Ura efg1 null mutant was transformed with linearized pAU-1. Ura$^+$ clones were selected and integration of the third copy of ALS1 was confirmed with PCR using the primers: 5'-CCGTTTATAC-CATCCAAATC-3'(SEQ ID NO. 5) and 5'-CTACATCCTC-CAATGATATAAC-3' (SEQ ID NO. 6). The resulting strain expressed ALS1 autonomously and regained the ability to filament on Lee's agar. See FIGS. 4B and C. Therefore, Efg1p induces filamentation through activation of ALS1 expression.

Because filamentation is a critical virulence factor in C. albicans, delineation of a pathway that regulates filamentation has important implications for pathogenicity. Prior to ALS1, no gene encoding a downstream effector of these regulatory pathways had been identified. Disruption of two other genes encoding cell surface proteins, HWP1 AND INT1, results in mutants with filamentation defects. Although HWP1 expression is also regulated by Efg1p, the autonomous expression of HWP1 in the efg1/efg1 mutant fails to restore filamentation. Therefore Hwp1p alone does not function as an effector of filamentation downstream of EFG1. Also, the regulatory elements controlling INT1 expression are not known. Thus, Als1p is the first cell-surface protein identified that functions as a downstream effector of filamentation, thereby suggesting a pivotal role for this protein in the virulence of C. albicans.

Figure 5A:
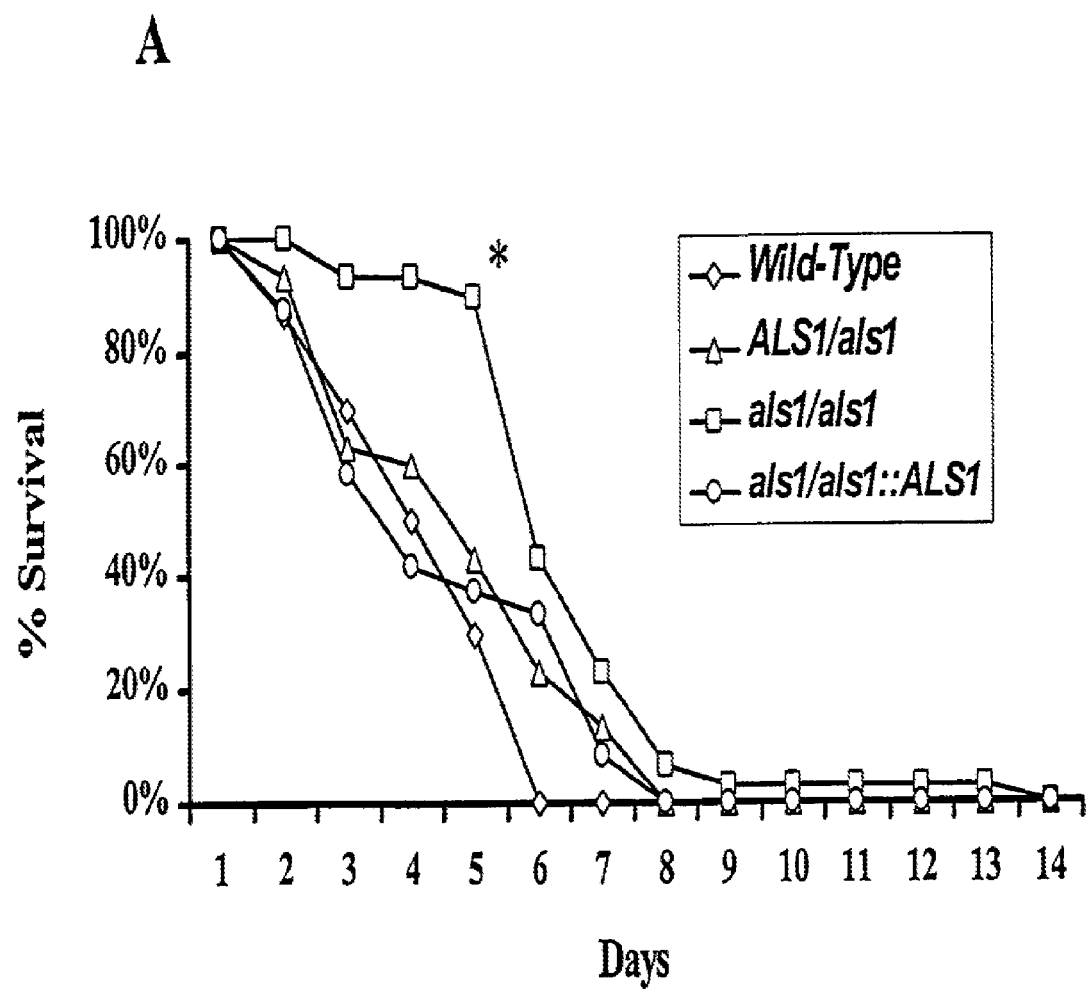
FIGS. 5A, 5B show the reduction of virulence in the mouse model of hematogenously disseminated candidiasis by (A) Male Balb/C mice (n=30 for each yeast strain) were injected with stationary phase blastospores ($10^6$ per mouse in 0.5 ml of PBS). Curves are the compiled results of three replicate experiments (n=30 mice for each strain). The doubling times of all strains, grown in YPD at 30° C., ranged between 1.29 to 1.52 hours and were not statistically different from each other. Southern blot analysis of total chromosomal DNA was used to match the identity of the genotype of *C. albicans* strains retrieved from infected organs with those of *C. albicans* strains used to infect the mice. Statistical analysis was obtained by Wilcoxon rank sum test and corrected for multiple comparisons with the Bonferroni correction. *P<0.002 for the als1/als1 mutant versus each of the other strains. (B) Histological micrographs of kidneys infected with *C. albicans* wild-type, homozygous als1 null mutant, or heterozygous ALS1 complemented mutant. Kidney samples were retrieved 28 hours (a) or 40 (b) hours post infection, fixed in paraformaldehyde and sections were stained with silver (magnification, X400). Arrows denote *C. albicans* cells.
Figure 5B:
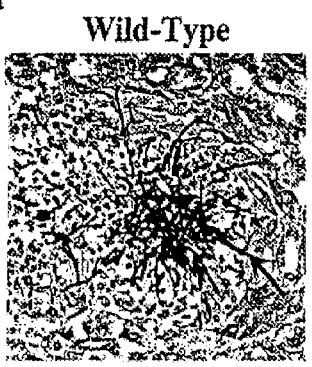
Figure 5B:
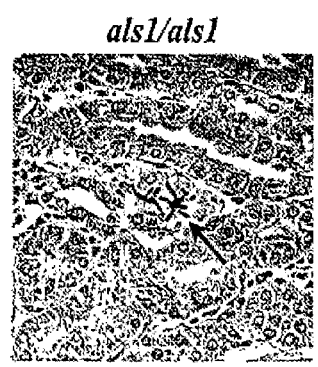
Figure 5B:
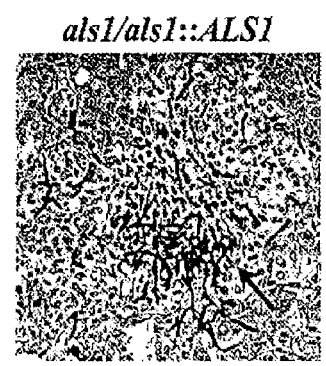
Figure 5B:
Figure 5B:
Figure 5B:

The contribution of Als1p to C. albicans virulence was tested in a model of hematogenously disseminated candidiasis, A. S. Ibrahim et al., Infect. Immun. 63, 1993 (1995). Referring to FIG. 5A, mice infected with the als1/als1 null mutant survived significantly longer than mice infected with the ALS1/ALS1 strain, the ALS1/als1 mutant or the ALS1-complemented mutant. After 28 hours of infection, the kidneys of mice infected with the als1/als1 mutant contained significantly fewer organisms (5.70±0.46 $\log_{10}$ CFU/g) (P<0.0006 for both comparisons). No difference was detected in colony counts of organisms recovered from spleen, lungs, or liver of mice infected with either of the strains at any of the tested time points. These results indicate that immunotherapeutic strategies using ALS proteins as a vaccine have a protective prophylactic effect against disseminated candidiasis. See SEQ ID NOS. 10, 12, 14, 16, 18, 20, 22, and 24. Referring to FIG. 5B, examination of the kidneys of mice after 28 hours of infection revealed that the als1/als1 mutant produced significantly shorter filaments and elicited a weaker inflammatory response than did either the wild-type of ALS1-complemented strains. However, by 40 hours of infection, the length of the filaments and the number of leukocytes surrounding them were similar for all three strains.

The filamentation defect of the als1/als1 mutant seen on histopathology paralleled the in vitro filamentation assays on solid media. This mutant showed defective filamentation at early time points both in vivo and in vitro. This defect eventually resolved with prolonged infection/incubation. These results suggest that a filamentation regulatory pathway that is independent of ALS1 may become operative at later time points. The activation of this alternative filamentation pathway by 40 hours of infection is likely the reason why mice infected with the als1/als1 mutant subsequently succumbed in the ensuing 2-3 days.

Collectively, these data demonstrate that C. albicans ALS1 encodes a cell surface protein that mediates both adherence to endothelial cells and filamentation. Als1p is the only identified downstream effector of any known filamentation regulatory pathway in C. albicans. Additionally, Als1p contributes to virulence in hematogenous candidal infection. The cell surface location and dual functionality of Als1p make it an attractive target for both drug and immune-based therapies.

Example 3

Purification of ALS1 Adhesin Protein, Truncated N-Terminal Protein

For use as an immunogen, an ALS protein synthesized by E. coli is adequate when vaccination with a traditional protocol yield an immune response generating B cells expressing measurable anti-ALS anti-sera or levels of serum Ig from which polyclonals may be obtained. However, eukaryotic proteins synthesized by E. coli may not be functional due to improper folding or lack of glycosylation. Therefore, to determine if the ALS1 protein can block the adherence of C. albicans to endothelial cells, the protein is, preferably, purified from genetically engineered C. albicans, and formulated into a substantially pure pharmaceutical composition that is pharmacologically effective for prophylactic or therapeutic treatment of disseminated candidiasis.

PCR was used to amplify a fragment of ALS1, from nucleotides 52 to 1296. This 1246 bp fragment encompassed the N-terminus of the predicted ALS1 protein from the end of the signal peptide to the beginning of the tandem repeats. This region of ALS1 was amplified because it likely encodes the binding site of the adhesin, based on its homology to the binding region of the S. cerevisiae Agα1 gene product. In addition, this portion of the predicted ALS1 protein has few glycosylation sites and its size is appropriate for efficient expression in E. coli.

The N-terminal fragment of ALS1 was ligated into pQE32 to produce pINS5. In this plasmid, the N-terminal segment of the protein is expressed under control of the lac promoter and it has a 6-hits tag fused to its N-terminus so that it can be affinity purified. We transformed E. coli with pINS5, grew it under inducing conditions (in the presence of IPTG), and then lysed the cells. The cell lysate was passed through a $Ni^{2+}$-agarose column to affinity purify the ALS1-6H is fusion protein. This procedure yielded substantial amounts of ALS1-6H is. The fusion protein was further purified by SDS-PAGE. The band containing the protein was excised from the gel so that antiserum can be raised against it as described in detail herein. It will be appreciated by one skilled in the art that the surface adhesin protein according to the invention may be prepared and purified by a variety of known processes without departing from the spirit of the present invention based on the polynucleotide and polypeptide sequences of listed in SEQ ID. NO.1-SEQ ID NO.18. As noted above, analogues and derivatives of ALS1p may be prepared by known techniques based on conserved principles of amino acid substitution and nucleotide encoding degeneracy without departing from the invention. Thus, Such compositions may exhibit at least one conservative substitution in the polypeptide sequence and exhibit the same effect in disruption of adherence and filamentation pathways as the native ALS1p and antibodies that specifically bind thereto as described herein.

Example 4

Raising Polyclonal Antisera against ALS1 Protein

To determine whether antibodies against the ALS1 protein block the adherence of *Candida albicans* to endothelial and epithelial cells, and the selected host constituent in vitro, rabbits were inoculated with *S. cerevisiae* transformed with ALS1 protein. The immunization protocol used was the dose and schedule used by Hasenclever and Mitchell for production of antisera that identified the antigenic relationship among various species of *Candida*. Hasenclever, H. F. and W. O. Mitchell. 1960. Antigenic relationships of *Torulopsis glabrata* and seven species of the genus *Candida*. J. Bacteriol. 79:677-681. Control antisera were also raised against *S. cerevisiae* transformed with the empty plasmid. All yeast cells were grown in galactose to induce expression of the ALS genes. Before being tested in the adherence experiments, the serum was heat-inactivated at 56 C to remove all complement activity.

Sera from immunized rabbits were absorbed with whole cells of *S. cerevisiae* transformed with empty plasmid to remove antibodies that are reactive with components of the yeast other than ALS1 protein. The titer of the antisera was determined by immunofluorescence using *S. cerevisiae* that express the ALS1 gene. FITC-labeled anti-rabbit antibodies were purchased from commercial sources (Southern Biotechnology, Inc). Affinity-purified secondary antibodies were essential because many commercially available sera contain antibodies reactive with yeast glucan and mannan. The secondary antibodies were pretested using *Candida albicans* as well as *S. cerevisiae* transformed with the plasmid and were absorbed as needed to remove any anti-*S. cerevisiae* or anti-*Candida* antibodies. Negative controls were 1) preimmune serum, 2) *S. cerevisiae* transformed with the empty plasmid, and 3) *S. cerevisiae* transformed with the ALS gene but grown under conditions that suppress expression of the ALS gene (glucose).

In addition to the above experiments, Western blotting was used to provide further confirmation that an antiserum binds specifically to the ALS1 protein against which it was raised. *S. cerevisiae* transformed with the ALS1 were grown under inducing conditions and their plasma membranes were isolated by standard methods. Panaretou, B. and P. Piper. 1996. Isolation of yeast plasma membranes. p. 117-121. In LH. Evans. (ed.), Yeast Protocols. Methods in Cell and Molecular Biology. Humana Press, Totowa, N.J. Plasma membranes were also prepared from *S. cerevisiae* transformed with the empty plasmid and grown under identical conditions. The membrane proteins were separated by SDS-PAGE and then transferred to PVDF membrane by electroblotting. Harlow, E. and D. Lane. 1988. Antibodies: A Laboratory Manual. Cold Spring Harbor Laboratory Press. After being blocked with nonfat milk, the blot was incubated with the ALS antiserum. The preabsorbed antiserum did not react with proteins extracted from *S. cerevisiae* containing empty plasmid. This antiserum blocked the adherence of *S. cerevisiae* pYF5 (a clone that expresses *Candida albicans* ALS1) to endothelial cells.

Example 5

Antibodies Against Specific ALS Proteins Prophylactically Protect Mice from Mucosal and Hematogenously Disseminated Candidal Infections Antisera that block the adherence of a clone of *S. cerevisiae* transformed with an ALS1 were demonstrated to protect mice from intravenous challenge with *Candida albicans*. The antisera against the ALS proteins were first tested in the murine model of hematogenously disseminated candidiasis. Affinity-purified anti-ALS antibodies are effective in preventing adhesion of yeast cells to various substrates (see Example 3). Affinity-purification is useful in this system because antibody doses can be accurately determined. Moreover, the unfractionated antisera will undoubtedly contain large amounts of antibody directed toward antigens on the *S. cerevisiae* carrier cells. Many of these anti-*Saccharomyces* antibodies would likely bind to *C. albicans* and make interpretation of the results impossible. Additionally, it is quite possible that the procedure used to elute antibodies from *S. cerevisiae* that express the ALS protein may also elute small amounts of yeast mannan or glucan that could have adjuvant-like activity. The immunoaffinity-purified antibodies are further purified before use. They may also be preabsorbed with mouse splenocytes.

Figure 6:
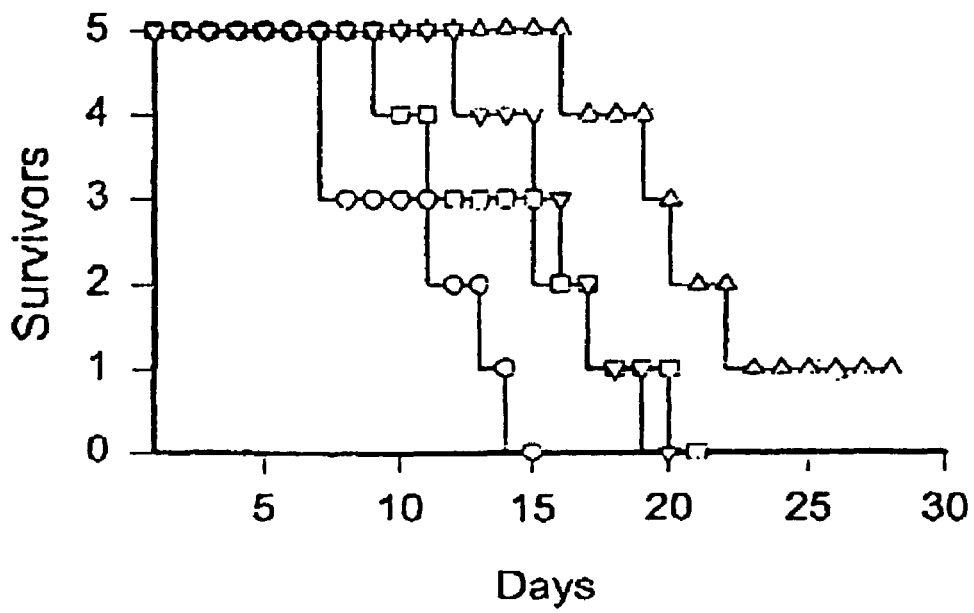
FIG. 6 shows the prophylactic effect of anti-ALS antibody against disseminated candidiasis as a function of surviving animals over a 30-day period for animals infused with anti-Als1p polyserum.

Antibody doses may be administered to cover the range that brackets the levels of serum antibody that can be expected in most active immunization protocols and to cover the range of antibody doses that are typically used for passive immunization in murine models of candidiasis. See Dromer, F., J. Charreirc, A. Contrepois, C. Carbon, and P. Yeni. 1987, *Protection, of mice against experimental cryptococcosis by anti-Cryptococcus neoformas monoclonal antibody*, Infect. Inimun. 55:749-752; Han, Y. and J. E. Cutler. 1995, *Antibody response that protects against disseminated candidiasis*, Infect. Immun. 63:2714-2719; Mukherjee, J., M. D. Scharff, and A. Casadevall. 1992, *Protective murine monoclonal antibodies to Cryptococcus neoformas*, Infect. Immun. 60:4534-4541; Sanford, J. E., D. M. Lupan, A. M. Schlageter, and T. R. Kozel. 1990, *Passive immunization against Cryptococcus neoformas with an isotype-switch family of monoclonal antibodies reactive with cryptococcal polysaccharide*, Infect. Inunun. 58:1919-1923. BALB/c mice (female, 7 week old, the NCI) were given anti-ALS that had been absorbed with mouse splenic cells by an intraperitoneal (i.p.) injection. Control mice received prebled serum that had been absorbed with mouse spenic cells, intact anti-ALS serum, or DPBS, respectively. For the pre-absorption, 2 ml of anti-ALS or prebled sera were mixed with 100µl of mouse (BALB/c, 7 weeks old female, NCI) splenic cells (app. $9\times10^6$ cells per ml) at room temperature for 20 minutes. The mixture was washed with warm sterile DPBS by centrifugation (@ 300×g) for 3 minutes. This procedure was repeated three times. The volume of i.p. injection was 0.4 ml per mouse. Four hours later, the mice were challenged with *C. albicans* (strain CA-1; $5\times10^5$ hydrophilic yeast cells per mouse) by i.v. injection. Then, their survival times were measured. See FIG. 6.

Previous studies have shown that antibodies administered via the intraperitoneal route are rapidly (within minutes) and almost completely transferred to the serum (Kozel and Casadevall, unpublished observations). As a control for effects of administering the antibody preparations, a parallel group of mice were treated with antibodies isolated from pre-immune serum that has been absorbed with *S. cerevisiae* transformed with the ALS gene. The survival time and numbers of yeast per gram of kidney were measured. Again, referring to FIG. 6, mice infected intravenously with $10^6$ blastopores of ALS1 null mutant had a longer median survival time when compared to mice infected with *Candida albicans* CAI-12 or *Candida* albicans in which one allele of the ALS1 had been deleted (p=0.003).

The N-terminal portion of Als1p was used to generate a mouse monoclonal anti-Als1p antibody using modification of the method described by Brawner and Cutler (1984). Briefly, 6-week old female BALB/c mice (NCI) were immunized by subcutaneous injection with 125 μg of the purified N-terminus of the Als1p in 0.25 ml of complete Freund's adjuvant (Gibco BRL). After 21 days, the mice received a subcutaneous booster injection of another 125 μg of the purified N-terminus of the Als1p in 0.25 ml of incomplete Freund's adjuvant. On day 28, the mice sera were assessed for anti-Als1p antibodies using enzyme-linked immunosorbent assay (ELISA) plates coated with the N-terminus of the Als1p. A final booster injection of 15 μg of the Als1p N-terminus without adjuvant was administered intravenously to mice that tested positive for anti-Als1p antibodies 31 days after the initial immunization, and splenocytes were prepared for hybridoma production as described previously (Brawner and Cutler, 1984). Hybridoma antibody production was determined using ELISA plates coated with the purified N-terminus of the Als1p. One of the hybrids obtained produced antibody that agglutinated *C. albicans* and was cloned four times by limiting dilution. A hybridoma cell line expressing antibody that binds to the same epitope was developed. This antibody reacted to *S. cerevisiae* that overexpressed Als1p, but not to *S. cerevisiae* transformed with the empty plasmid. The antibody also did not react with *S. cerevisiae* overexpressing Als5p, Als6p and was only weakly reactive against Als1p. ALS3p in *C. albicans* based upon the failure of the MAb to recognize any protein in the als1 null mutant strain upon germination. Heavy- and light chain-specific anti-mouse immunoglobulins (ICN Biomedicals) were used in ELISA to isotype this monoclonal antibody. The monoclonal antibody was isotyped to IgG1 with a kappa light chain. Mice administered monoclonal antibodies against the N-terminal domain of ALS1p exhibit a prophylactic and therapeutic effect against disseminated candidiasis.

Example 6

Polynucleotide Vaccination Produces Antibodies In Vivo to Alleviate Disseminated Candidal Infections In this embodiment, an immunogenic ALS polypeptide is introduced to a patient by delivering an effective amount of pharmaceutically acceptable polynucleotide coding for the selected immunogenic ALS polypeptide whereby the polynucleotide is expressed in vivo and the patient generates an immune response to the immunogen, thereby immunizing the patient in an equivalent manner to that demonstrated above for the protein. For example, immunogenic ALS1 polynucleotide compositions, suitable to be used as vaccines, may be prepared from the ALS genes and vectors as disclosed herein. The vaccine elicits an immune response in a subject which includes the production of anti-ALS antibodies that exhibit specificities for the selected ALS molecule, and may exhibit similar affinities and binding to similar epitopes as the polyclonal and monoclonal antibodies described herein. Immunogenic compositions, including vaccines, containing the ALS nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640) or the nucleic acid may be associated with an adjuvant. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used. Both liquid as well as lyophilized forms that are to be reconstituted will comprise agents, preferably buffers, in amounts necessary to suitably adjust the pH of the injected solution.

For any parenteral use, particularly if the formulation is to be administered intravenously, the total concentration of solutes should be controlled to make the preparation isotonic, hypotonic, or weakly hypertonic. Non-ionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The DNA sequences used in these methods can be those sequences which do not integrate into the genome of the host cell. These may be non-replicating DNA sequences, or specific-replicating sequences genetically engineered to lack the genome-integration ability. The naked ALS polynucleotide materials comprise the DNA of SEQ ID NO.:7, 9, 11, 13, 15, 17, 19, 21, or 23 or in RNA sequences coding for the ALS1p polypeptide of SEQ ID NO.:8, 10, 12, 14, 16, 18, 20, 22, or 24 including conservative substitutions and corresponding polynucleotides encoding such analogues or derivatives. With the availability of automated nucleic acid synthesis equipment, both the DNA sequences and the corresponding RNA sequences can be synthesized directly or derived from the native organism.

Where the polynucleotide is to be DNA, promoters suitable for use in various vertebrate systems are well known. For example, for use in murine systems, suitable strong promoters include RSV LTR, MPSV LTR, SV40 IEP, and metallothionein promoter. In humans, on the other hand, promoters such as CMV IEP may advantageously be used. When the polynucleotide is mRNA, it can be readily prepared from the corresponding DNA in vitro. For example, conventional techniques utilize phage RNA polymerases SP6, T3, or T7 to prepare mRNA from DNA templates in the presence of the individual ribonucleoside triphosphates. An appropriate phage promoter, such as a T7 origin of replication site is placed in the template DNA immediately upstream of the gene to be transcribed. Systems utilizing T7 in this manner are well known, and are described in the literature, e.g., in Current Protocols in Molecular Biology, §3.8 (vol. 1 1988).

To produce the composition for injection, any convenient plasmid vector may be used, preferably comprising a selectable expression vector and promoter. Suitable plasmids include pc DNA3 (Invitrogen), pCI (Promega), pCMV-beta galactosidase (Clontech) or pRc/CMV-HBs (S) Davis et al. Human Molecular Genetics 2:1847-1851. The ALS gene is inserted in the vector in any convenient manner. The gene may be obtained from *Candida* genomic DNA and amplified using PCR and the PCR product cloned into the vector. The ALS gene plasmid may be transferred, such as by electroporation, into *E. coli* for replication therein. Plasmids may be extracted from the *E. coli* in any convenient manner.

The plasmid containing the ALS gene or specified N-terminal fragment may be administered in any convenient manner to the host, such as intramuscularly, intranasally, intramusonally, intraperitoneally, transdermally or any selected route that elicits the immune response. DNA immunization with the ALS gene or fragment may elicit both cellular and humoral immune responses and produces significant protective immunity and therapeutic effect to *Candida albicans*.

As noted above, the ALS gene, gene product or specific antibodies may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and passive vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the ALS polypeptide or fragment thereof, and antibodies thereto, and if needed, to produce a humoral or cell-mediated immune response. Suitable dosage ranges are readily determinable by one skilled in the art and may be of the order of about 1 microgram to about 1 mg. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if immunogens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the immunogen locally near the site of administration to produce a depot effect facilitating a slow, sustained release of antigen to cells of the immune system. Adjuvants can also attract cells of the immune system to the immunogen and stimulate such cells to elicit immune responses.

Immunostimulatory agents or adjuvants have been used for many years to improve the host immune responses to vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

We claim:

1. A method of vaccinating a mammalian host against *Candida albicans* comprising administering to said host a pharmacologically effective amount of an immunogenic composition comprising an isolated polypeptide consisting of the N-terminal domain of the *Candida albicans* agglutinin like sequence (ALS) polypeptide, Als3p, in a pharmacologically acceptable excipient, wherein the N-terminal domain extends from the end of the signal peptide for the beginning of the tandem repeat of said *Candida albicans* Als3p, and wherein the method inhibits adhesion of the *Candida albicans* to endothelial cells in said host.

2. The method of claim 1, wherein said method comprises administering the immunogenic composition subcutaneously to said mammalian host.

3. The method of claim 1, wherein the polypeptide is substantially pure.

4. The method of claim 1, wherein the immunogenic composition comprises an immunostimulating adjuvant.

5. The method of claim 4, wherein the immunostimulating adjuvant is alum.

6. The method of any one of claims 2, 4 and 5, wherein said immunogenic composition is administered to the mammalian host as a booster dose.

7. The method of claim 1, wherein the polypeptide is produced in *Saccharomyces cerevisiae*.

8. The method of claim 1, wherein the mammalian host is a human and said polypeptide is purified.

9. The method of claim 1, wherein the Als3p has the amino acid sequence set forth in SEQ ID NO: 12.

* * * * *

SEQUENCE LISTING

<160> NUMBER OF SEQ ID NOS: 43

<210> SEQ ID NO 1
<211> LENGTH: 33
<212> TYPE: DNA
<213> ORGANISM: Candida albicans

<400> SEQUENCE: 1
ccgctcgaga tgcttcaaca atttacattg tta                                 33

<210> SEQ ID NO 2
<211> LENGTH: 32
<212> TYPE: DNA

<213> ORGANISM: Candida albicans

<400> SEQUENCE: 2
ccgctcgagt cactaaatga acaaggacaa ta                                    32

<210> SEQ ID NO 3
<211> LENGTH: 31
<212> TYPE: DNA
<213> ORGANISM: Candida albicans

<400> SEQUENCE: 3
cgggatccag atgcttcaac aatttacatt g                                     31

<210> SEQ ID NO 4
<211> LENGTH: 31
<212> TYPE: DNA
<213> ORGANISM: Candida albicans

<400> SEQUENCE: 4
cgggatcctc actaaatgaa caaggacaat a                                     31

<210> SEQ ID NO 5
<211> LENGTH: 20
<212> TYPE: DNA
<213> ORGANISM: Candida albicans

<400> SEQUENCE: 5
ccgtttatac catccaaatc                                                  20

<210> SEQ ID NO 6
<211> LENGTH: 22
<212> TYPE: DNA
<213> ORGANISM: Candida albicans

<400> SEQUENCE: 6
ctacatcctc caatgatata ac                                               22

<210> SEQ ID NO 7
<211> LENGTH: 3786
<212> TYPE: DNA
<213> ORGANISM: Candida albicans

<400> SEQUENCE: 7
atgcttcaac aatttacatt gttattccta tatttgtcaa ttgcaagtgc aaagacaatc      60
actggtgttt ttgatagttt taattcatta acttggtcca atgctgctaa ttatgctttc     120
aaagggccag atacccaac ttggaatgct gttttgggtt ggtccttaga tggtaccagt      180
gccaatccag gggatacatt cacattgaat atgccatgtg tgtttaaata tactacttca    240
caaacatctg ttgatttaac tgccgatggt gttaaatatg ctacttgtca attttattct    300
ggtgaagaat tcacaacttt ttctacatta acatgtactg tgaacgacgc tttgaaatca    360
tccattaagg catttggtac agttactta ccaattgcat tcaatgttgg tggaacaggt     420
tcatcaactg atttggaaga ttctaaatgt tttactgctg gtaccaatac agtcacattt    480
aatgatggtg ataagatat ctcaattgat gttgagtttg aaaagtcaac cgttgatcca    540
agtgcatatt tgtatgcttc cagagttatg ccaagtctca ataaggtcac aactctttt     600 gtggcaccac aatgtgaaaa tggttacaca tctggtacaa tggggttctc cagtagtaac    660
ggtgacgttg ctattgattg ctcaaatatt catattggta tcacaaaagg attaaatgat    720
tggaattatc cggtttcatc tgaatcattt agttacacta aacttgtac atctaatgga    780

```
attcagatta aatatcaaaa tgtacctgct ggttatcgtc catttattga tgcttatatt      840
tctgctacag atgttaacca atatacttta gcatatacca atgattatac ttgtgctggc      900
agtcgtctgc aaagtaaacc tttcacttta agatggactg gatacaagaa tagtgatgcc      960
ggatctaacg gtattgtcat tgttgctaca actagaacag ttacagacag taccactgct     1020
gtcactactt taccattcaa tccaagtgtt gataaaacca aaacaatcga aattttgcaa     1080
cctattccaa ccactaccat cacaacttca tatgttggtg tgactacttc ctatctgact     1140
aagactgcac caattggtga acagctact gttattgttg atgtgccata tcatactacc      1200
acaactgtta ccagtgaatg gacaggaaca atcactacca ccacaactcg taccaatcca     1260
actgattcaa ttgacacagt ggtggtacaa gttccactgc caaatccaac tgttagtact     1320
actgaatatt ggtctcagtc ctttgctaca accactacag ttactgctcc tccaggtggt     1380
accgatactg tgattatcag agagccacca aaccatactg tcactactac tgaatattgg     1440
tcacaatcct ttgctactac tactactgtt actgctcctc caggtggtac tgactcagta     1500
attatcagag aaccaccaaa tccaactgtc actacaaccg agtattggtc tcaatccttt     1560
gctactacta ctacagttac tgctcctcca ggtggtactg actcagtaat tatcagagaa     1620
cctccaaacc caactgtcac caccactgaa tattggtccc aatcttacgc aaccacaact     1680
actgtgactc tcctccagg aggcactgac tcagtaatta tcagagaacc accaaaccac     1740
actgtcacta ctactgaata ctggtcacaa tcatatgcca ccactaccac tgtaactgca     1800
ccaccaggtg gtactgacac tgttatcatt agagagccac caaaccacac tgtcactact     1860
actgagtatt ggtctcaatc gtttgctact accacaactg taactggtcc accaagtggc     1920
actgatactg ttatcattag ggaaccacca aacccaactg tcaccactac tgaatactgg     1980
tctcaatcat atgcaaccac tactaccatt accgctccac ctggtgaaac tgataccgtt     2040
cttatcagag agccaccaaa ccatactgtc actactactg aatactggtc tcaatcatat     2100
gctacaacca ccactgttac tgcaccacct ggtgaaaccg ataccgttct tatcagagag     2160
ccaccaaacc atactgtcac tactactgaa tactggtctc aatcatatgc tacaaccacc     2220
actgttactg caccaccagg tggtaccgat actgttatca ttagagagcc accaaatcca     2280
acagttacta ctactgaata ttggtcacaa tcatttgcca caaccaccac agttactgct     2340
cctccaggtg gtactgacac tgtgattatc tatgaaagca tgtcaagttc aaagatttct     2400
acatcctcca atgatataac cagtatcatt ccatcatttt cccgtcctca ttatgtcaac     2460
agcacaacct ccgatttgtc aacatttgaa tcttcatcca tgaatactcc tacttctatc     2520
agtagtgatg gtatgttgtt gtcttctaca actttggtta ctgaatcaga aacaactaca     2580
gaactgattt gcagtgatgg taaagagtgt tctagattgt ccagttcttc tggtattgtc     2640
acaaatccag atagcaatga atcctcaatc gtaactagta ctgttcctac tgcaagtaca     2700
atgtctgatt cactttcttc aactgatggt attagtgcta catcttctga taatgtttca     2760
aaatcaggag tatcagttac aaccgaaact tctgttacaa ctattcaaac tactccaaac     2820
ccattatcat cttcagtgac atcattgact cagttgtctt caattccaag tgtttcagaa     2880
agtgaaagta agttacatt tacaagcaat ggagacaacc aaagtggtac tcatgattca     2940
caatctactt ccactgaaat tgaaattgta acaaccagtt ctactaaagt tttaccacct     3000
gtcgtttctt ctaatactga tttgactagt gaaccaacaa ataccagaga caaccaact     3060 acattatcaa ctacttcaaa ctccatcact gaagatatca ccacatctca acctacaggt     3120
```

-continued

```
gataatggag acaatacttc atcaaccaat ccagttccaa ctgtggcaac aagtactta   3180
gcatctgcaa gtgaagaaga caacaaaagc ggttctcatg aatcagcatc cacaagtttg   3240
aaaccaagta tgggtgaaaa ttctggatta actacttcta ctgaaattga agctacaaca   3300
accagtccta cagaagctcc atcacctgct gtttcttctg gtactgatgt aactactgaa   3360
ccaactgata ctagagaaca acctactaca ttatcaacta cttcaaaaac aaacagtgaa   3420
ctggttgcta ctacacaagc tactaatgaa aatggtggta atctccatc aactgattta    3480
acatcaagct tgacaacagg cacctcagca tctacaagtg ctaatagcga acttgttact   3540
agtggatctg ttactggtgg agctgttgcc agtgcttcaa atgatcaatc acattctact   3600
tctgttacca acagcaacag cattgtatct aatacccac aaactacatt gagtcaacaa    3660
gttacctcat cctcaccttc aaccaacaca ttcattgctt ctacatacga tggctctggt   3720
tctattatcc aacattctac ttggttgtac ggtttgatca cattattgtc cttgttcatt   3780
tagtga                                                               3786
```

<210> SEQ ID NO 8
<211> LENGTH: 1260
<212> TYPE: PRT
<213> ORGANISM: Candida albicans

<400> SEQUENCE: 8

```
Met Leu Gln Gln Phe Thr Leu Leu Phe Leu Tyr Leu Ser Ile Ala Ser
1               5                   10                  15

Ala Lys Thr Ile Thr Gly Val Phe Asp Ser Phe Asn Ser Leu Thr Trp
            20                  25                  30

Ser Asn Ala Ala Asn Tyr Ala Phe Lys Gly Pro Gly Tyr Pro Thr Trp
        35                  40                  45

Asn Ala Val Leu Gly Trp Ser Leu Asp Gly Thr Ser Ala Asn Pro Gly
    50                  55                  60

Asp Thr Phe Thr Leu Asn Met Pro Cys Val Phe Lys Tyr Thr Thr Ser
65                  70                  75                  80

Gln Thr Ser Val Asp Leu Thr Ala Asp Gly Val Lys Tyr Ala Thr Cys
                85                  90                  95

Gln Phe Tyr Ser Gly Glu Glu Phe Thr Thr Phe Ser Thr Leu Thr Cys
            100                 105                 110

Thr Val Asn Asp Ala Leu Lys Ser Ser Ile Lys Ala Phe Gly Thr Val
        115                 120                 125

Thr Leu Pro Ile Ala Phe Asn Val Gly Gly Thr Gly Ser Ser Thr Asp
    130                 135                 140

Leu Glu Asp Ser Lys Cys Phe Thr Ala Gly Thr Asn Thr Val Thr Phe
145                 150                 155                 160

Asn Asp Gly Asp Lys Asp Ile Ser Ile Asp Val Glu Phe Glu Lys Ser
                165                 170                 175

Thr Val Asp Pro Ser Ala Tyr Leu Tyr Ala Ser Arg Val Met Pro Ser
            180                 185                 190

Leu Asn Lys Val Thr Thr Leu Phe Val Ala Pro Gln Cys Glu Asn Gly
        195                 200                 205

Tyr Thr Ser Gly Thr Met Gly Phe Ser Ser Asn Gly Asp Val Ala
    210                 215                 220

Ile Asp Cys Ser Asn Ile His Ile Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255
```

```
Thr Ser Asn Gly Ile Gln Ile Lys Tyr Gln Asn Val Pro Ala Gly Tyr
            260                 265                 270

Arg Pro Phe Ile Asp Ala Tyr Ile Ser Ala Thr Asp Val Asn Gln Tyr
            275                 280                 285

Thr Leu Ala Tyr Thr Asn Asp Tyr Thr Cys Ala Gly Ser Arg Ser Gln
            290                 295                 300

Ser Lys Pro Phe Thr Leu Arg Trp Thr Gly Tyr Lys Asn Ser Asp Ala
305                 310                 315                 320

Gly Ser Asn Gly Ile Val Ile Ala Thr Thr Arg Thr Val Thr Asp
                325                 330                 335

Ser Thr Thr Ala Val Thr Thr Leu Pro Phe Asn Pro Ser Val Asp Lys
            340                 345                 350

Thr Lys Thr Ile Glu Ile Leu Gln Pro Ile Pro Thr Thr Thr Ile Thr
            355                 360                 365

Thr Ser Tyr Val Gly Val Thr Thr Ser Tyr Ser Thr Lys Thr Ala Pro
            370                 375                 380

Ile Gly Glu Thr Ala Thr Val Ile Val Asp Val Pro Tyr His Thr Thr
385                 390                 395                 400

Thr Thr Val Thr Ser Glu Trp Thr Gly Thr Ile Thr Thr Thr Thr
            405                 410                 415

Arg Thr Asn Pro Thr Asp Ser Ile Asp Thr Val Val Gln Val Pro
            420                 425                 430

Ser Pro Asn Pro Thr Val Ser Thr Glu Tyr Trp Ser Gln Ser Phe
            435                 440                 445

Ala Thr Thr Thr Val Thr Ala Pro Pro Gly Gly Thr Asp Thr Val
            450                 455                 460

Ile Ile Arg Glu Pro Pro Asn His Thr Val Thr Thr Thr Glu Tyr Trp
465                 470                 475                 480

Ser Gln Ser Phe Ala Thr Thr Thr Val Thr Ala Pro Pro Gly Gly
                485                 490                 495

Thr Asp Ser Val Ile Ile Arg Glu Pro Pro Asn Pro Thr Val Thr Thr
            500                 505                 510

Thr Glu Tyr Trp Ser Gln Ser Phe Ala Thr Thr Thr Val Thr Ala
            515                 520                 525

Pro Pro Gly Gly Thr Asp Ser Val Ile Ile Arg Glu Pro Pro Asn Pro
            530                 535                 540

Thr Val Thr Thr Thr Glu Tyr Trp Ser Gln Ser Tyr Ala Thr Thr Thr
545                 550                 555                 560

Thr Val Thr Ala Pro Pro Gly Gly Thr Asp Ser Val Ile Ile Arg Glu
                565                 570                 575

Pro Pro Asn His Thr Val Thr Thr Thr Glu Tyr Trp Ser Gln Ser Tyr
            580                 585                 590

Ala Thr Thr Thr Thr Val Thr Ala Pro Pro Gly Gly Thr Asp Thr Val
            595                 600                 605

Ile Ile Arg Glu Pro Pro Asn His Thr Val Thr Thr Thr Glu Tyr Trp
            610                 615                 620

Ser Gln Ser Phe Ala Thr Thr Thr Val Thr Gly Pro Ser Gly
625                 630                 635                 640

Thr Asp Thr Val Ile Ile Arg Glu Pro Pro Asn Pro Thr Val Thr Thr
            645                 650                 655

Thr Glu Tyr Trp Ser Gln Ser Tyr Ala Thr Thr Thr Ile Thr Ala
            660                 665                 670
```

```
Pro Pro Gly Glu Thr Asp Thr Val Leu Ile Arg Glu Pro Asn His
            675                 680                 685

Thr Val Thr Thr Thr Glu Tyr Trp Ser Gln Ser Tyr Ala Thr Thr Thr
690                 695                 700

Thr Val Thr Ala Pro Pro Gly Glu Thr Asp Thr Val Leu Ile Arg Glu
705                 710                 715                 720

Pro Pro Asn His Thr Val Thr Thr Thr Glu Tyr Trp Ser Gln Ser Tyr
                725                 730                 735

Ala Thr Thr Thr Thr Val Thr Ala Pro Pro Gly Gly Thr Asp Thr Val
            740                 745                 750

Ile Ile Arg Glu Pro Pro Asn Pro Thr Val Thr Thr Thr Glu Tyr Trp
            755                 760                 765

Ser Gln Ser Phe Ala Thr Thr Thr Val Thr Ala Pro Pro Gly Gly
            770                 775                 780

Thr Asp Thr Val Ile Ile Tyr Glu Ser Met Ser Ser Lys Ile Ser
785                 790                 795                 800

Thr Ser Ser Asn Asp Ile Thr Ser Ile Ile Pro Ser Phe Ser Arg Pro
                805                 810                 815

His Tyr Val Asn Ser Thr Thr Ser Asp Leu Ser Thr Phe Glu Ser Ser
            820                 825                 830

Ser Met Asn Thr Pro Thr Ser Ile Ser Ser Asp Gly Met Leu Leu Ser
            835                 840                 845

Ser Thr Thr Leu Val Thr Glu Ser Glu Thr Thr Thr Glu Ser Ile Cys
            850                 855                 860

Ser Asp Gly Lys Glu Cys Ser Arg Leu Ser Ser Ser Gly Ile Val
865                 870                 875                 880

Thr Asn Pro Asp Ser Asn Glu Ser Ser Ile Val Thr Ser Thr Val Pro
                885                 890                 895

Thr Ala Ser Thr Met Ser Asp Ser Leu Ser Ser Thr Asp Gly Ile Ser
            900                 905                 910

Ala Thr Ser Ser Asp Asn Val Ser Lys Ser Gly Val Ser Val Thr Thr
            915                 920                 925

Glu Thr Ser Val Thr Thr Ile Gln Thr Thr Pro Asn Pro Leu Ser Ser
930                 935                 940

Ser Val Thr Ser Leu Thr Gln Leu Ser Ser Ile Pro Ser Val Ser Glu
945                 950                 955                 960

Ser Glu Ser Lys Val Thr Phe Thr Ser Asn Gly Asp Asn Gln Ser Gly
                965                 970                 975

Thr His Asp Ser Gln Ser Thr Ser Thr Glu Ile Glu Ile Val Thr Thr
            980                 985                 990

Ser Ser Thr Lys Val Leu Pro Pro Val Val Ser Ser Asn Thr Asp Leu
            995                 1000                1005

Thr Ser Glu Pro Thr Asn Thr Arg Glu Gln Pro Thr Thr Leu Ser
      1010                1015                1020

Thr Thr Ser Asn Ser Ile Thr Glu Asp Ile Thr Thr Ser Gln Pro
      1025                1030                1035

Thr Gly Asp Asn Gly Asp Asn Thr Ser Ser Thr Asn Pro Val Pro
      1040                1045                1050

Thr Val Ala Thr Ser Thr Leu Ala Ser Ala Ser Glu Glu Asp Asn
      1055                1060                1065

Lys Ser Gly Ser His Glu Ser Ala Ser Thr Ser Leu Lys Pro Ser
      1070                1075                1080

Met Gly Glu Asn Ser Gly Leu Thr Thr Ser Thr Glu Ile Glu Ala
```

```
                    1085                1090                1095
Thr Thr Thr Ser Pro Thr Glu Ala Pro Ser Pro Ala Val Ser Ser
            1100                1105                1110
Gly Thr Asp Val Thr Thr Glu Pro Thr Asp Thr Arg Glu Gln Pro
        1115                1120                1125
Thr Thr Leu Ser Thr Thr Ser Lys Thr Asn Ser Glu Ser Val Ala
        1130                1135                1140
Thr Thr Gln Ala Thr Asn Glu Asn Gly Gly Lys Ser Pro Ser Thr
        1145                1150                1155
Asp Leu Thr Ser Ser Leu Thr Thr Gly Thr Ser Ala Ser Thr Ser
        1160                1165                1170
Ala Asn Ser Glu Leu Val Thr Ser Gly Ser Val Thr Gly Gly Ala
        1175                1180                1185
Val Ala Ser Ala Ser Asn Asp Gln Ser His Ser Thr Ser Val Thr
        1190                1195                1200
Asn Ser Asn Ser Ile Val Ser Asn Thr Pro Gln Thr Thr Leu Ser
        1205                1210                1215
Gln Gln Val Thr Ser Ser Ser Pro Ser Thr Asn Thr Phe Ile Ala
        1220                1225                1230
Ser Thr Tyr Asp Gly Ser Gly Ser Ile Ile Gln His Ser Thr Trp
        1235                1240                1245
Leu Tyr Gly Leu Ile Thr Leu Leu Ser Leu Phe Ile
        1250                1255                1260

<210> SEQ ID NO 9
<211> LENGTH: 1404
<212> TYPE: DNA
<213> ORGANISM: Candida albicans

<400> SEQUENCE: 9
atgcttttac aatttttgtt gctaagcctc tgtgtatcag ttgctactgc aaaagttatt      60
acgggtgttt tcaatagttt tgattcgttg acatggacaa gagctggtaa ttatgcttat     120
aagggcccaa atagaccaac ttggaatgct gttttgggct ggtctttaga tggtactagt     180
gcaaatccag gagacacatt cacattgaat atgccatgtg tttttaaatt tattaccgat     240
caaacatctg ttgatttgac tgctgaaggt gttaaatatg ctacatgtca gttttattca     300
ggtgaagaat ttcaaacatt tcttcatta aaatgtactg tgagcaatac tttaacatca     360
tctattaagg ctttgggtac ggttacttta ccaatttcat ttaatgttgg tggaacaggt     420
tcatcggttg atttggaaag ttctcaatgt tttaaggctg caccaacac agttactttt     480
aatgatggtg ataaaaaaat ctcaattgac gttgattttg agaaaacaaa cgaagatgca     540
agtggatatt tcatagcgtc aagacttatt ccaagtatta caaagtttc aatcacttat     600
gtggcaccac aatgtgcaaa tggctacaca tctggtgcaa tggggttcat agttctcact     660
ggtgacacta ctattgactg ttcaaatgtt catgttggta ttacaaaggg attaaatgat     720
tggaattttc cggtatcgtc tgattcatta agttacaata aaacttgttc atctacaggt     780
atttctatca catatgaaaa tgtccccgct ggttatcgtc catttttga cgtatatact     840
ctggtgtcag gccagaacag acaattaaga tatactaatg attatgcctg tgttggtagt     900
tccttacaaa gtaagccgtt caatttaaga ttgagaggat acaataatag tgaagctaat     960
tctaacggtt ttgtcattgt tgctacaacc cgaacagtta ctgacagtac tactgctgtc    1020
actactttac cttttaatcc aagtgttgac aaaaccaaaa caatcgaaat tttgcaacct    1080
```

-continued

```
attccaacaa ccaccatcac aacttcatat gttggtgtga ctacttccta cctgactaaa    1140
actgcaccaa ttggtgaaac agctactgtt attgttgatg tgccatatca tactaccaca    1200
actgttacca gtgaatggac aggaacaatc actaccacta caactcgtac caatccaact    1260
gattctatag atactgtcgt tgtgcaagtt ccactgccaa atccaactgt cactacaacc    1320
gagtattggt ctcagtcata tgctactact actactgtta ctgctcctcc aggtggtact    1380
gactcagtaa ttatcagaga acct                                           1404
```

<210> SEQ ID NO 10
<211> LENGTH: 468
<212> TYPE: PRT
<213> ORGANISM: Candida albicans

<400> SEQUENCE: 10

```
Met Leu Leu Gln Phe Leu Leu Leu Ser Leu Cys Val Ser Val Ala Thr
 1               5                  10                  15

Ala Lys Val Ile Thr Gly Val Phe Asn Ser Phe Asp Ser Leu Thr Trp
                20                  25                  30

Thr Arg Ala Gly Asn Tyr Ala Tyr Lys Gly Pro Asn Arg Pro Thr Trp
            35                  40                  45

Asn Ala Val Leu Gly Trp Ser Leu Asp Gly Thr Ser Ala Asn Pro Gly
        50                  55                  60

Asp Thr Phe Thr Leu Asn Met Pro Cys Val Phe Lys Phe Ile Thr Asp
 65                  70                  75                  80

Gln Thr Ser Val Asp Leu Thr Ala Glu Gly Val Lys Tyr Ala Thr Cys
                 85                  90                  95

Gln Phe Tyr Ser Gly Glu Glu Phe Thr Thr Phe Ser Ser Leu Lys Cys
            100                 105                 110

Thr Val Ser Asn Thr Leu Thr Ser Ser Ile Lys Ala Leu Gly Thr Val
        115                 120                 125

Thr Leu Pro Ile Ser Phe Asn Val Gly Gly Thr Gly Ser Ser Val Asp
130                 135                 140

Leu Glu Ser Ser Gln Cys Phe Lys Ala Gly Thr Asn Thr Val Thr Phe
145                 150                 155                 160

Asn Asp Gly Asp Lys Lys Ile Ser Ile Asp Val Asp Phe Glu Lys Thr
                165                 170                 175

Asn Glu Asp Ala Ser Gly Tyr Phe Ile Ala Ser Arg Leu Ile Pro Ser
            180                 185                 190

Ile Asn Lys Val Ser Ile Thr Tyr Val Ala Pro Gln Cys Ala Asn Gly
        195                 200                 205

Tyr Thr Ser Gly Ala Met Gly Phe Ile Val Leu Thr Gly Asp Thr Thr
    210                 215                 220

Ile Asp Cys Ser Asn Val His Val Gly Ile Thr Lys Gly Leu Asn Asp
225                 230                 235                 240

Trp Asn Phe Pro Val Ser Ser Asp Ser Leu Ser Tyr Asn Lys Thr Cys
                245                 250                 255

Ser Ser Thr Gly Ile Ser Ile Thr Tyr Glu Asn Val Pro Ala Gly Tyr
            260                 265                 270

Arg Pro Phe Phe Asp Val Tyr Thr Ser Val Ser Gly Gln Asn Arg Gln
        275                 280                 285

Leu Arg Tyr Thr Asn Asp Tyr Ala Cys Val Gly Ser Ser Leu Gln Ser
    290                 295                 300

Lys Pro Phe Asn Leu Arg Leu Arg Gly Tyr Asn Asn Ser Glu Ala Asn
305                 310                 315                 320
```

```
Ser Asn Gly Phe Val Ile Val Ala Thr Thr Arg Thr Val Thr Asp Ser
                325                 330                 335

Thr Thr Ala Val Thr Thr Leu Pro Phe Asn Pro Ser Val Asp Lys Thr
            340                 345                 350

Lys Thr Ile Glu Ile Leu Gln Pro Ile Pro Thr Thr Thr Ile Thr Thr
        355                 360                 365

Ser Tyr Val Gly Val Thr Thr Ser Tyr Ser Thr Lys Thr Ala Pro Ile
    370                 375                 380

Gly Glu Thr Ala Thr Val Ile Val Asp Val Pro Tyr His Thr Thr Thr
385                 390                 395                 400

Thr Val Thr Ser Glu Trp Thr Gly Thr Ile Thr Thr Thr Thr Thr Arg
                405                 410                 415

Thr Asn Pro Thr Asp Ser Ile Asp Thr Val Val Gln Val Pro Ser
            420                 425                 430

Pro Asn Pro Thr Val Thr Thr Glu Tyr Trp Ser Gln Ser Tyr Ala
        435                 440                 445

Thr Thr Thr Thr Val Thr Ala Pro Pro Gly Gly Thr Asp Ser Val Ile
    450                 455                 460

Ile Arg Glu Pro
465

<210> SEQ ID NO 11
<211> LENGTH: 3360
<212> TYPE: DNA
<213> ORGANISM: Candida albicans

<400> SEQUENCE: 11
atgctacaac aatatacatt gttactcata tatttgtcgg ttgcgactgc aaagacaatc      60
actggtgttt tcaacagttt taattcattg acttggtcta atgctgctac ttataattat     120
aagggaccag gaaccccaac ttggaatgct gttttgggtt ggtctttaga tggtactagt     180
gcaagtccgg gagatacatt cacattgaat atgccatgtg tgtttaaatt tactacttct     240
caaacatctg ttgatttgac tgctcatggt gttaaatatg ctacatgtca atttcaggca     300
ggtgaagaat ttatgacctt ttctacatta acatgtactg tgagcaatac tttgactcca     360
tctattaagg ctttgggtac tgtcacctta ccacttgcat tcaatgtagg tggaactggt     420
tcttctgttg atttggaaga ttctaaatgt tttactgctg tactaacac agttacattt      480 aatgatggtg gcaagaaaat ctctattaat gttgattttg aaaggtcaaa tgtcgatcca     540
aaagggtact taactgattc cagagttata ccaagtctca acaaagtgtc aactctttt      600 gttgcaccac aatgtgcaaa tggttacaca tctggtacaa tgggattcgc taacacttat     660
ggtgatgttc aaattgactg ttcaaatatt catgttggta ttcaaaagg attgaatgat      720 tggaattatc cggtttcatc tgaatcattt agttacacca aacttgttc atctaatggt      780 atctttatca catataaaaa tgttcctgcc ggttatcgtc catttgttga cgcttatatt     840
tctgctacag atgttaattc gtacaccttg tcgtatgcta atgaatatac ttgtgctggt     900
ggttattggc aacgtgcacc tttcacatta agatggactg gatacagaaa tagtgatgct     960
ggatctaacg gtattgttat tgtggctact accagaacag ttacagacag tactaccgct    1020
gtgaccacct taccattcga tcctaaccgc gacaaaacta agacaattga aattttgaaa    1080
cctattccaa caactacaat cacaacatca tatgttggtg tgactacttc ctacctgacc    1140
aaaactgcac caattgggga aactgctact gttattgttg atattccata tcacactacc    1200
```

```
actactgtta ccagtaaatg gacaggaaca attacttcca ccacaacaca tactaatcca    1260
actgactcaa tagacactgt cattgtacaa gttccactgc caaacccaac tgttactacc    1320
actgaatatt ggtctcaatc atttgctacc accaccacca ttactggacc accaggaaac    1380
actgatactg ttttaatcag agaaccaccg aaccatactg tcactacaac cgagtactgg    1440
tcagaatctt acactactac tagtactttc actgctcctc caggtggaac tgattcagtt    1500
attatcaagg aacctccaaa tccaactgtc acaactaccg agtactggtc agaatcttac    1560
actaccacta gtaccttcac tgctcctcca ggtggaactg attcagttat tatcaaggaa    1620
ccaccaaacc atactgtaac cacaactgaa tattggtcac aatcttacac taccactact    1680
actgtcaccg ctccaccagg aggtactgat actgtcttag tcagagaacc accaaaccat    1740
actgttacaa ctaccgagta ctggtcacaa tcttacacta caaccaccac tgttattgcc    1800
ccaccaggtg gcactgattc ggttatcatt agagaacctc caaatccaac tgtcacaacc    1860
actgagtact ggtctcaatc ttacgcaact accactacca ttaccgctcc tccaggtgag    1920
accgatactg tccttattag agaaccacca accatactg taaccacaac tgagtattgg    1980
tctcaatctt atgcaactac tactacaatc actgctcctc aggtgaaac cgataccgtt    2040
cttattaggg aaccaccaaa tcacactgtc actactactg aatactggtc acaatcattt    2100
gctacaacca aactgtaac tgcaccacca ggtggtactg acactgttat cattagagaa    2160
ccaccaaacc acactgtcac tactactgag tattggtctc aatcttacgc aaccactact    2220
accattaccg ctccacctgg tgagaccgat accgttctta ttagggaacc accaaatcac    2280
acagttacta ctactgaata ctggtcacaa tcatatgcaa ctactaccac tatcatcgca    2340
ccaccaggtg aaactgatac tgtttaatc agagagccac caaacccaac tgttaccacc    2400
accgaatact ggtctcaatc ctataccact gctactaccg ttactgcacc accaggtgga    2460
actgatactg tgattattta tgacaccatg tcaagttcag aaatttcttc attttctcgt    2520
cctcattaca ccaaccatac aactttgtgg tctacaactt gggttattga acaaaaaca    2580
attacagaaa ctagctgtga aggtgataaa ggttgttctt gggtttctgt ttctactcgt    2640
attgtcacaa ttcctaataa tatcgaaact cctatggtta ctaatactgt tgattctaca    2700
accacagaat ccacttcaca atccccatct ggtatttttt cagagtcagg agtatctgtt    2760
gaaacagaat cttctactgt tactactgct caaacaaatc caagtgttcc aacaactgaa    2820
agtgaggttg tatttactac taaaggaaac aacgaaaatg gtccttatga atcaccatct    2880
actaatgtga aatcaagtat ggatgaaaac tctgaattta ctacttccac agctgcttcc    2940
acttctactg atattgaaaa tgaaaccata gcaacaaccg gttccgtgga agcttcatcg    3000
cctatcattt cttctagtgc tgatgaaact actactgtta ctactactgc tgaatcaacc    3060
agtgtcattg aacaaccaac caataataat ggtggtggta agcccccatc tgcaacttca    3120
tctccatcta caactacaac tgctaataat gactctgtta ttactggtac aacatcaacc    3180
aaccaatctc aatctcaatc tcaatataat tctgataccc aacaaactac attgagtcaa    3240
caaatgactt catctttagt tagtttacat atgcttacta catttgacgg atctggttct    3300
gttattcaac attctacttg gttatgtggt ttgatcacat tattatcctt gtttatttaa    3360
```

<210> SEQ ID NO 12
<211> LENGTH: 1119
<212> TYPE: PRT
<213> ORGANISM: Candida albicans

<400> SEQUENCE: 12

```
Met Leu Gln Gln Tyr Thr Leu Leu Ile Tyr Leu Ser Val Ala Thr
1               5                   10                  15

Ala Lys Thr Ile Thr Gly Val Phe Asn Ser Phe Asn Ser Leu Thr Trp
            20                  25                  30

Ser Asn Ala Ala Thr Tyr Asn Tyr Lys Gly Pro Gly Thr Pro Thr Trp
        35                  40                  45

Asn Ala Val Leu Gly Trp Ser Leu Asp Gly Thr Ser Ala Ser Pro Gly
    50                  55                  60

Asp Thr Phe Thr Leu Asn Met Pro Cys Val Phe Lys Phe Thr Thr Ser
65                  70                  75                  80

Gln Thr Ser Val Asp Leu Thr Ala His Gly Val Lys Tyr Ala Thr Cys
                85                  90                  95

Gln Phe Gln Ala Gly Glu Glu Phe Met Thr Phe Ser Thr Leu Thr Cys
            100                 105                 110

Thr Val Ser Asn Thr Leu Thr Pro Ser Ile Lys Ala Leu Gly Thr Val
        115                 120                 125

Thr Leu Pro Leu Ala Phe Asn Val Gly Gly Thr Gly Ser Ser Val Asp
    130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                165                 170                 175

Asn Val Asp Pro Lys Gly Tyr Leu Thr Asp Ser Arg Val Ile Pro Ser
            180                 185                 190

Leu Asn Lys Val Ser Thr Leu Phe Val Ala Pro Gln Cys Ala Asn Gly
        195                 200                 205

Tyr Thr Ser Gly Thr Met Gly Phe Ala Asn Thr Tyr Gly Asp Val Gln
    210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Ser Ser Asn Gly Ile Phe Ile Thr Tyr Lys Asn Val Pro Ala Gly Tyr
            260                 265                 270

Arg Pro Phe Val Asp Ala Tyr Ile Ser Ala Thr Asp Val Asn Ser Tyr
        275                 280                 285

Thr Leu Ser Tyr Ala Asn Glu Tyr Thr Cys Ala Gly Gly Tyr Trp Gln
    290                 295                 300

Arg Ala Pro Phe Thr Leu Arg Trp Thr Gly Tyr Arg Asn Ser Asp Ala
305                 310                 315                 320

Gly Ser Asn Gly Ile Val Ile Val Ala Thr Thr Arg Thr Val Thr Asp
                325                 330                 335

Ser Thr Thr Ala Val Thr Thr Leu Pro Phe Asp Pro Asn Arg Asp Lys
            340                 345                 350

Thr Lys Thr Ile Glu Ile Leu Lys Pro Ile Pro Thr Thr Thr Ile Thr
        355                 360                 365

Thr Ser Tyr Val Gly Val Thr Thr Ser Tyr Ser Thr Lys Thr Ala Pro
    370                 375                 380

Ile Gly Glu Thr Ala Thr Val Ile Val Asp Ile Pro Tyr His Thr Thr
385                 390                 395                 400

Thr Thr Val Thr Ser Lys Trp Thr Gly Thr Ile Thr Ser Thr Thr Thr
                405                 410                 415
```

```
His Thr Asn Pro Thr Asp Ser Ile Asp Thr Val Ile Val Gln Val Pro
                420                 425                 430

Ser Pro Asn Pro Thr Val Thr Thr Thr Glu Tyr Trp Ser Gln Ser Phe
        435                 440                 445

Ala Thr Thr Thr Thr Ile Thr Gly Pro Pro Gly Asn Thr Asp Thr Val
            450                 455                 460

Leu Ile Arg Glu Pro Pro Asn His Thr Val Thr Thr Glu Tyr Trp
465                 470                 475                 480

Ser Glu Ser Tyr Thr Thr Ser Thr Phe Thr Ala Pro Pro Gly Gly
                485                 490                 495

Thr Asp Ser Val Ile Ile Lys Glu Pro Pro Asn Pro Thr Val Thr Thr
                500                 505                 510

Thr Glu Tyr Trp Ser Glu Ser Tyr Thr Thr Thr Ser Thr Phe Thr Ala
        515                 520                 525

Pro Pro Gly Gly Thr Asp Ser Val Ile Ile Lys Glu Pro Pro Asn His
        530                 535                 540

Thr Val Thr Thr Thr Glu Tyr Trp Ser Gln Ser Tyr Thr Thr Thr Thr
545                 550                 555                 560

Thr Val Thr Ala Pro Pro Gly Gly Thr Asp Thr Val Leu Val Arg Glu
                565                 570                 575

Pro Pro Asn His Thr Val Thr Thr Thr Glu Tyr Trp Ser Gln Ser Tyr
            580                 585                 590

Thr Thr Thr Thr Thr Val Ile Ala Pro Pro Gly Gly Thr Asp Ser Val
                595                 600                 605

Ile Ile Arg Glu Pro Pro Asn Pro Thr Val Thr Thr Glu Tyr Trp
610                 615                 620

Ser Gln Ser Tyr Ala Thr Thr Thr Ile Thr Ala Pro Pro Gly Glu
625                 630                 635                 640

Thr Asp Thr Val Leu Ile Arg Glu Pro Pro Asn His Thr Val Thr Thr
                645                 650                 655

Thr Glu Tyr Trp Ser Gln Ser Tyr Ala Thr Thr Thr Ile Thr Ala
            660                 665                 670

Pro Pro Gly Glu Thr Asp Thr Val Leu Ile Arg Glu Pro Pro Asn His
        675                 680                 685

Thr Val Thr Thr Thr Glu Tyr Trp Ser Gln Ser Phe Ala Thr Thr Thr
690                 695                 700

Thr Val Thr Ala Pro Pro Gly Gly Thr Asp Thr Val Ile Ile Arg Glu
705                 710                 715                 720

Pro Pro Asn His Thr Val Thr Thr Thr Glu Tyr Trp Ser Gln Ser Tyr
            725                 730                 735

Ala Thr Thr Thr Thr Ile Thr Ala Pro Pro Gly Glu Thr Asp Thr Val
            740                 745                 750

Leu Ile Arg Glu Pro Pro Asn His Thr Val Thr Thr Glu Tyr Trp
        755                 760                 765

Ser Gln Ser Tyr Ala Thr Thr Thr Ile Ile Ala Pro Pro Gly Glu
770                 775                 780

Thr Asp Thr Val Leu Ile Arg Glu Pro Pro Asn Pro Thr Val Thr Thr
785                 790                 795                 800

Thr Glu Tyr Trp Ser Gln Ser Tyr Thr Thr Ala Thr Thr Val Thr Ala
        805                 810                 815

Pro Pro Gly Gly Thr Asp Thr Val Ile Ile Tyr Asp Thr Met Ser Ser
        820                 825                 830

Ser Glu Ile Ser Ser Phe Ser Arg Pro His Tyr Thr Asn His Thr Thr
```

```
                835                840                845
Leu Trp Ser Thr Thr Trp Val Ile Glu Thr Lys Thr Ile Thr Glu Thr
    850                855                860

Ser Cys Glu Gly Asp Lys Gly Cys Ser Trp Val Ser Val Ser Thr Arg
865                870                875                880

Ile Val Thr Ile Pro Asn Asn Ile Glu Thr Pro Met Val Thr Asn Thr
                885                890                895

Val Asp Ser Thr Thr Thr Glu Ser Thr Ser Gln Ser Pro Ser Gly Ile
            900                905                910

Phe Ser Glu Ser Gly Val Ser Val Glu Thr Glu Ser Ser Thr Val Thr
            915                920                925

Thr Ala Gln Thr Asn Pro Ser Val Pro Thr Thr Glu Ser Glu Val Val
    930                935                940

Phe Thr Thr Lys Gly Asn Asn Glu Asn Gly Pro Tyr Glu Ser Pro Ser
945                950                955                960

Thr Asn Val Lys Ser Ser Met Asp Glu Asn Ser Glu Phe Thr Thr Ser
                965                970                975

Thr Ala Ala Ser Thr Ser Thr Asp Ile Glu Asn Glu Thr Ile Ala Thr
            980                985                990

Thr Gly Ser Val Glu Ala Ser Ser Pro Ile Ile Ser Ser Ser Ala Asp
            995                1000                1005

Glu Thr Thr Thr Val Thr Thr Thr Ala Glu Ser Thr Ser Val Ile
    1010                1015                1020

Glu Gln Pro Thr Asn Asn Asn Gly Gly Gly Lys Ala Pro Ser Ala
    1025                1030                1035

Thr Ser Ser Pro Ser Thr Thr Thr Ala Asn Asn Asp Ser Val
    1040                1045                1050

Ile Thr Gly Thr Thr Ser Thr Asn Gln Ser Gln Ser Gln Ser Gln
    1055                1060                1065

Tyr Asn Ser Asp Thr Gln Gln Thr Thr Leu Ser Gln Gln Met Thr
    1070                1075                1080

Ser Ser Leu Val Ser Leu His Met Leu Thr Thr Phe Asp Gly Ser
    1085                1090                1095

Gly Ser Val Ile Gln His Ser Thr Trp Leu Cys Gly Leu Ile Thr
    1100                1105                1110

Leu Leu Ser Leu Phe Ile
    1115

<210> SEQ ID NO 13
<211> LENGTH: 1407
<212> TYPE: DNA
<213> ORGANISM: Candida albicans

<400> SEQUENCE: 13 atgctttac aattttgtt gctaagcctc tgtgtatcag ttgctacggc aaaagttatt      60
acaggtgttt tcaatagttt taattcgtta acttgggcca atgctgcttc ttatccatat    120
agaggtccag ctactcctac ttggaccgct gtaataggat ggtctttaga tggagctact    180
gctagtgctg gtgacacatt cacgttagac atgccttgtg ttttcaaatt tattactgat    240
caaacgtcaa ttgatttagt tgctgatggt cgtacttatg ctacttgtaa tttgaattct    300
gccgaagagt ttactacttt ttctagtgtg tcatgtactg tgactactac aatgactgct    360
gacaccaaag ccataggaac tgtaacatta ccttttctcat tcagtgtggg gggatcaggt   420
tcagatgttg atttggcaaa ttctcaatgt tttactgcag gaatcaatac agttactttt   480
```

```
aatgatggtg acactagcat ttccacaaca gttgattttg aaaaatcaac cgtggcctcc    540
agcgatcgta tcttgttgtc aagaattta cccagtcttt cacaagcagt aaatctttt    600
cttccccaag aatgtgcaaa tggttatact tctggtacaa tgggattttc gactgctggt    660
actggtgcta ctatagattg ttccacagtt catgtcggga tatcaaatgg ttgaatgat    720
tggaattatc caatttcact ggaatctttt tcttacacaa agacctgtac atcaacaagt    780
gttttagtaa cttttcaaaa tgttcctgcc ggatatcgtc catttgttga tgcttatatt    840
tctgcaacac gagtcagctc ataccatg caatacacta atatatgc ttgtgttggc    900
gcggcttctg ttgatgactc atttactcat acttggcggg gatatagtaa tagtcaagct    960
ggttctaatg gtattaccat tgtggtaaca actagaacag ttacagacag taccactgct   1020
gtgactactt taccattcaa ttccgatact gacaaaacca aaacaatcga aattttacaa   1080
cctattccaa caactaccat tacaacttca tatgttggtg tgacaacttc ctacctgact   1140
aaaactgcac caattggtga aacagctact gttattgttg atgtgccata tcatactact   1200
acaactgtta ccagtgaatg gacaggaaca attactacca ctacaactcg taccaatcca   1260
actgattcta tagatactgt cgttgttcaa gttccactgc caaatccaac tgtcactaca   1320
accgagtatt ggtctcagtc atatgctact actactactg ttactgctcc tccaggtggt   1380
actgactcag taattatcag agaacct                                       1407

<210> SEQ ID NO 14
<211> LENGTH: 469
<212> TYPE: PRT
<213> ORGANISM: Candida albicans

<400> SEQUENCE: 14

Met Leu Leu Gln Phe Leu Leu Leu Ser Leu Cys Val Ser Val Ala Thr
1               5                   10                  15

Ala Lys Val Ile Thr Gly Val Phe Asn Ser Phe Asn Ser Leu Thr Trp
            20                  25                  30

Ala Asn Ala Ala Ser Tyr Pro Tyr Arg Gly Pro Ala Thr Pro Thr Trp
        35                  40                  45

Thr Ala Val Ile Gly Trp Ser Leu Asp Gly Ala Thr Ala Ser Ala Gly
    50                  55                  60

Asp Thr Phe Thr Leu Asp Met Pro Cys Val Phe Lys Phe Ile Thr Asp
65                  70                  75                  80

Gln Thr Ser Ile Asp Leu Val Ala Asp Gly Arg Thr Tyr Ala Thr Cys
                85                  90                  95

Asn Leu Asn Ser Ala Glu Glu Phe Thr Thr Phe Ser Ser Val Ser Cys
            100                 105                 110

Thr Val Thr Thr Thr Met Thr Ala Asp Thr Lys Ala Ile Gly Thr Val
        115                 120                 125

Thr Leu Pro Phe Ser Phe Ser Val Gly Gly Ser Gly Ser Asp Val Asp
    130                 135                 140

Leu Ala Asn Ser Gln Cys Phe Thr Ala Gly Ile Asn Thr Val Thr Phe
145                 150                 155                 160

Asn Asp Gly Asp Thr Ser Ile Ser Thr Thr Val Asp Phe Glu Lys Ser
                165                 170                 175

Thr Val Ala Ser Ser Asp Arg Ile Leu Leu Ser Arg Ile Leu Pro Ser
            180                 185                 190

Leu Ser Gln Ala Val Asn Leu Phe Leu Pro Gln Glu Cys Ala Asn Gly
        195                 200                 205
```

-continued

Tyr Thr Ser Gly Thr Met Gly Phe Ser Thr Ala Gly Thr Gly Ala Thr
       210                 215                 220

Ile Asp Cys Ser Thr Val His Val Gly Ile Ser Asn Gly Leu Asn Asp
225                 230                 235                 240

Trp Asn Tyr Pro Ile Ser Ser Glu Ser Phe Ser Tyr Thr Lys Thr Cys
                245                 250                 255

Thr Ser Thr Ser Val Leu Val Thr Phe Gln Asn Val Pro Ala Gly Tyr
                260                 265                 270

Arg Pro Phe Val Asp Ala Tyr Ile Ser Ala Thr Arg Val Ser Ser Tyr
            275                 280                 285

Thr Met Gln Tyr Thr Asn Ile Tyr Ala Cys Val Gly Ala Ala Ser Val
        290                 295                 300

Asp Asp Ser Phe Thr His Thr Trp Arg Gly Tyr Ser Asn Ser Gln Ala
305                 310                 315                 320

Gly Ser Asn Gly Ile Thr Ile Val Val Thr Thr Arg Thr Val Thr Asp
                325                 330                 335

Ser Thr Thr Ala Val Thr Thr Leu Pro Phe Asn Ser Asp Thr Asp Lys
                340                 345                 350

Thr Lys Thr Ile Glu Ile Leu Gln Pro Ile Pro Thr Thr Thr Ile Thr
            355                 360                 365

Thr Ser Tyr Val Gly Val Thr Thr Ser Tyr Ser Thr Lys Thr Ala Pro
        370                 375                 380

Ile Gly Glu Thr Ala Thr Val Ile Val Asp Val Pro Tyr His Thr Thr
385                 390                 395                 400

Thr Thr Val Thr Ser Glu Trp Thr Gly Thr Ile Thr Thr Thr Thr Thr
                405                 410                 415

Arg Thr Asn Pro Thr Asp Ser Ile Asp Thr Val Val Gln Val Pro
            420                 425                 430

Ser Pro Asn Pro Thr Val Thr Thr Glu Tyr Trp Ser Gln Ser Tyr
        435                 440                 445

Ala Thr Thr Thr Thr Val Thr Ala Pro Pro Gly Gly Thr Asp Ser Val
    450                 455                 460

Ile Ile Arg Glu Pro
465

<210> SEQ ID NO 15
<211> LENGTH: 3813
<212> TYPE: DNA
<213> ORGANISM: Candida albicans

<400> SEQUENCE: 15
atgattcaac aatttacatt gttattccta tatttgtcgt ttgcgactgc aaaggcgatc    60
actggtattt tcaatagtat tgactcatta acttggtcca atgctggcaa ttacgctttc   120
aaaggaccag ataccccaac ttggaatgct gtgttgggtt ggtcattaga tggtaccagt   180
gccaatccag gagatacatt catattaaac atgccatgtg tgtttaaatt cactgcttcc   240
caaaaatctg ttgatttgac tgccgatggt gttaaatatg ctacttgtca attttattct   300
ggtgaagagt ttacaacttt ttctacatta acatgtactg tgaacgacgc tttgaaatca   360
tccattaagg catttggtac agttactttta ccaattgcat tcaatgttgg tggaacaggt   420
tcatcaactg atttggaaga ttctaaatgt tttactgctg gtatcaatac ggtaacattt   480
aatgatggca gtaaaaagct ctcaattgct gttaattttg aaaagtcaac agttgatcga   540
agtgggtatt tgactacttc cagatttatg ccgagtctca ataaaattgc tactctttat   600

```
gtggcaccac aatgtgaaaa cggttacaca tctggtacaa tgggattctc cactagttat     660
ggggatgttg ctattgactg ttcaaatgta catattggta tttcaaaagg agtaaatgat     720
tggaatcatc cagttacgtc tgaatcattt agttacacta aaagctgttc atcttttggt     780
atctctatca catatcaaaa tgttcctgcc ggttatcgtc catttattga cgcttatatt     840
tctccctcag ataataacca gtatcaattg tcgtataaaa atgactatac ttgtgttgat     900
gattattggc aacatgcacc tttcacttta aaatggactg gatataagaa tagtgatgcc     960
ggatctaacg gtattgtcat tgttgctaca actagaacag ttacagacag taccactgct    1020
gtcactactt taccattcaa tccaagtgtt gataaaacca aaacaatcga aattttgcaa    1080
cctattccaa ccactaccat cacaacttca tatgttggtg tgactacttc ctatctgact    1140
aagactgcac caattggtga acagctact  cttattgttg atgtgccata tcatactacc    1200
acaactgtta caagtaaatg gacaggaaca attacgatga ctacaactcg taccaatcca    1260
actgattcaa ttgacacagt ggtggtacaa gttccacttc caaatccaac tacaactaca    1320
acccagtttt ggtcagagtc atttactagt actactacaa tcaccaacaa gccagaaggc    1380
acagactcag tcattgtcaa ggaaccacac aatcctactg ttaccaccac agagttttgg    1440
tcagaatcat atgccactac tgaaacaatt actacagggc cacttggtac tgatagtatc    1500
gttatacatg atccattgga agaactgtct tctactactg ctattgagtc gagtgattct    1560
aatatttcaa gctcagctca agaatcatcc agtctggttg agcagtcatc aagtatagtt    1620
ggattgtcat caagttcaga tataccatta agttcagaca tgccatcatc gagctcaact    1680
gggttaacat ctagtgagtc gtctactgtc tcaagttatg atagcgattc atcaagtagt    1740
agtgagttat ctacattttc tagttctgag agctactcgt caagtatctc tgataccaca    1800 aactttggg attcttcaag ttccgattta gagtccaccc tgatcacttg gagttcctcc     1860
atcgatgcac aatctagtca gtcggtacag tcagtatcaa actccattag cacaagtcag    1920
gagacaacat caagctcagg tgaggaatcc aatacgtcag tcaccgatat tttagtgtca    1980
agtgatgcaa gttctatttt gaactctgat atttccagtt attacccatc tagcacaatt    2040
ctgctaagtg acgattttcc acacactata gcaggggagc cagatagccg atcaagctca    2100
tcaatagcat ctactgttga gatttctagt gatttggtct ctcttacaag tgacccaaca    2160
agcagttttg attcatcttc tagtttgaat tctgactcat catctctgcc attcagtgac    2220
gaaagtgata tttcggcttc atctagtttt tctacattag ttgccccatc ttttcattg    2280 agttcaagca gttcattatc tttgatatat ccacattatg tcaactcaac aacatatcat    2340
gcatcggaat ccgaaagctc atctgtcgct tcaccatcag tggcaagtga gtcagctaat    2400
gatgacacac atactttgct ggaatctact gacactacat ccattattgg cacagattct    2460
tctactgtga catttgtcg tcgtgataac ggagatggct gtattgtaac agggataaca    2520
tcgtctagta tagacagtga acagactagt gatgtgacga caacttctag ctttgttgct    2580
tccagcacac caacctcggc agaacagtct attactgaca atccaaatat tgactcactg    2640
caaacaagtg ctagttcttc aactaaatca tcagtttctg tgtcagatac agtagtaaat    2700
tcaattttat tatctgaaac gtcaaccta tcatctgatg acggtacttc ttcggatacc     2760
agcattagct caacaacaaa ctctgatact ggtaatatta atgctgggtc gctgcacaaa    2820
agtactgctt ccatcaaaga actgtcaatt cagaaaacgg gagtaacgtt aagttctagt    2880
tatttgtcga caaaattgag ttctacatca gatattacta ttgaacttat tactactgaa    2940
```

-continued

```
cttactacta tcgaagataa cgaaccaaac actttactt caactccgtc aagtcattct  3000
gaaatatttt ctagtgataa tagtgtttta tcaaaacaag ttgatagaga aagtactatt  3060
aaaacttctc ctacaacgga cgtcactaca gtatcatctt tatcagtaca ttcaacagaa  3120
gcttctactg caacactcgg agaaaattca tttagcaatg ttgccagtac tccattgaat  3180
actgcaacat ctttaagatc aacaagttca tcatcaaatc atgctaccga atcaagtgga  3240
acggttaaaa gtgaagcaag tgtagaagca attccttctc cacctacttc aactgacaac  3300
agactaagct attcaactga agaagccgaa ggtattacat atgctaattc aggttctaca  3360
aataacctca taaccgaatc tcaagtggcc gctccaacag attctacttc agtgttgatt  3420
gaaaacctag tggtaacttc gacctttgat gataactcgt cagcagctgt ggatcaacca  3480
agtaaaacta gtcgattga agaatctatt atgaatcctg attcaaccaa tgaaactaac  3540
aatggattta tcgctacttt atcacaagct caagtaccaa gttcctcgat tcattcagag  3600
ttaatactga ctacgacggc taaaacaact gatgcttcga tgaatggaga cagtgctgct  3660
tcaaactcac agccaaccac attaattcaa caagtagcaa cttcctccta caatcaaccc  3720
cttattacca cttatgccgg atcttcatcc gccactaaac atccttcctg gttgcttaaa  3780
tttattagcg ttgcattatt cttctttcta tga  3813
```

<210> SEQ ID NO 16
<211> LENGTH: 1270
<212> TYPE: PRT
<213> ORGANISM: Candida albicans

<400> SEQUENCE: 16

```
Met Ile Gln Gln Phe Thr Leu Leu Phe Leu Tyr Leu Ser Phe Ala Thr
 1               5                  10                  15

Ala Lys Ala Ile Thr Gly Ile Phe Asn Ser Ile Asp Ser Leu Thr Tyr
            20                  25                  30

Ser Asn Ala Gly Asn Tyr Ala Phe Lys Gly Pro Gly Tyr Pro Thr Tyr
        35                  40                  45

Asn Ala Val Leu Gly Tyr Ser Leu Asp Gly Thr Ser Ala Asn Pro Gly
    50                  55                  60

Asp Thr Phe Ile Leu Asn Met Pro Cys Val Phe Lys Phe Thr Ala Ser
65                  70                  75                  80

Gln Lys Ser Val Asp Leu Thr Ala Asp Gly Val Lys Tyr Ala Thr Cys
                85                  90                  95

Gln Phe Tyr Ser Gly Glu Glu Phe Thr Thr Phe Ser Thr Leu Thr Cys
            100                 105                 110

Thr Val Asn Asp Ala Leu Lys Ser Ser Ile Lys Ala Phe Gly Thr Val
        115                 120                 125

Thr Leu Pro Ile Ala Phe Asn Val Gly Thr Gly Ser Ser Thr Asp
    130                 135                 140

Leu Glu Asp Ser Lys Cys Phe Thr Ala Gly Ile Asn Thr Val Thr Phe
145                 150                 155                 160

Asn Asp Gly Ser Lys Lys Leu Ser Ile Ala Val Asn Phe Glu Lys Ser
                165                 170                 175

Thr Val Asp Arg Ser Gly Tyr Leu Thr Thr Ser Arg Phe Met Pro Ser
            180                 185                 190

Leu Asn Lys Ile Ala Thr Leu Tyr Val Ala Pro Gln Cys Glu Asn Gly
        195                 200                 205

Tyr Thr Ser Gly Thr Met Gly Phe Ser Thr Ser Tyr Gly Asp Val Ala
    210                 215                 220
```

```
Ile Asp Cys Ser Asn Val His Ile Gly Ile Ser Lys Gly Val Asn Asp
225                 230                 235                 240

Tyr Asn His Pro Val Thr Ser Glu Ser Phe Ser Tyr Thr Lys Ser Cys
            245                 250                 255

Ser Ser Phe Gly Ile Ser Ile Thr Tyr Gln Asn Val Pro Ala Gly Tyr
            260                 265                 270

Arg Pro Phe Ile Asp Ala Tyr Ile Ser Pro Ser Asp Asn Asn Gln Tyr
            275                 280                 285

Gln Leu Ser Tyr Lys Asn Asp Tyr Thr Cys Val Asp Asp Tyr Tyr Gln
            290                 295                 300

His Ala Pro Phe Thr Leu Lys Tyr Thr Gly Tyr Lys Asn Ser Asp Ala
305                 310                 315                 320

Gly Ser Asn Gly Ile Val Ile Ala Thr Thr Arg Thr Val Thr Asp
                325                 330                 335

Ser Thr Thr Ala Val Thr Thr Leu Pro Phe Asn Pro Ser Val Asp Lys
            340                 345                 350

Thr Lys Thr Ile Glu Ile Leu Gln Pro Ile Pro Thr Thr Thr Ile Thr
            355                 360                 365

Thr Ser Tyr Val Gly Val Thr Thr Ser Tyr Ser Thr Lys Thr Ala Pro
            370                 375                 380

Ile Gly Glu Thr Ala Thr Leu Ile Val Asp Val Pro Tyr His Thr Thr
385                 390                 395                 400

Thr Thr Val Thr Ser Lys Tyr Thr Gly Thr Ile Thr Met Thr Thr Thr
            405                 410                 415

Arg Thr Asn Pro Thr Asp Ser Ile Asp Thr Val Val Gln Val Pro
            420                 425                 430

Leu Pro Asn Pro Thr Thr Thr Thr Gln Phe Tyr Ser Glu Ser Phe
            435                 440                 445

Thr Ser Thr Thr Thr Ile Thr Asn Lys Pro Glu Gly Thr Asp Ser Val
450                 455                 460

Ile Val Lys Glu Pro His Asn Pro Thr Val Thr Thr Thr Glu Phe Tyr
465                 470                 475                 480

Ser Glu Ser Tyr Ala Thr Thr Glu Thr Ile Thr Thr Gly Pro Leu Gly
            485                 490                 495

Thr Asp Ser Ile Val Ile His Asp Pro Leu Glu Glu Ser Ser Ser Thr
            500                 505                 510

Thr Ala Ile Glu Ser Ser Asp Ser Asn Ile Ser Ser Ser Ala Gln Glu
            515                 520                 525

Ser Ser Ser Val Glu Gln Ser Ser Ser Ile Val Gly Leu Ser Ser
            530                 535                 540

Ser Ser Asp Ile Pro Leu Ser Ser Asp Met Pro Ser Ser Ser Ser Thr
545                 550                 555                 560

Gly Leu Thr Ser Ser Glu Ser Ser Thr Val Ser Ser Tyr Asp Ser Asp
            565                 570                 575

Ser Ser Ser Ser Ser Glu Leu Ser Thr Phe Ser Ser Ser Glu Ser Tyr
            580                 585                 590

Ser Ser Ser Ile Ser Asp Thr Thr Asn Phe Tyr Asp Ser Ser Ser Ser
            595                 600                 605

Asp Leu Glu Ser Thr Ser Ile Thr Tyr Ser Ser Ser Ile Asp Ala Gln
            610                 615                 620

Ser Ser Gln Ser Val Gln Ser Val Ser Asn Ser Ile Ser Thr Ser Gln
625                 630                 635                 640
```

-continued

```
Glu Thr Thr Ser Ser Ser Gly Glu Glu Ser Asn Thr Ser Val Thr Asp
                645                 650                 655

Ile Leu Val Ser Ser Asp Ala Ser Ser Ile Leu Asn Ser Asp Ile Ser
            660                 665                 670

Ser Tyr Tyr Pro Ser Ser Thr Ile Ser Leu Ser Asp Asp Phe Pro His
        675                 680                 685

Thr Ile Ala Gly Glu Pro Asp Ser Arg Ser Ser Ser Ile Ala Ser
    690                 695                 700

Thr Val Glu Ile Ser Ser Asp Leu Val Ser Leu Thr Ser Asp Pro Thr
705                 710                 715                 720

Ser Ser Phe Asp Ser Ser Ser Leu Asn Ser Asp Ser Ser Ser
            725                 730                 735

Pro Phe Ser Asp Glu Ser Asp Ile Ser Ala Ser Ser Ser Phe Ser Thr
            740                 745                 750

Leu Val Ala Pro Ser Phe Ser Leu Ser Ser Ser Ser Leu Ser Leu
            755                 760                 765

Ile Tyr Pro His Tyr Val Asn Ser Thr Thr Tyr His Ala Ser Glu Ser
    770                 775                 780

Glu Ser Ser Ser Val Ala Ser Pro Ser Val Ala Ser Glu Ser Ala Asn
785                 790                 795                 800

Asp Asp Thr His Thr Leu Ser Glu Ser Thr Asp Thr Ser Ile Ile
            805                 810                 815

Gly Thr Asp Ser Ser Thr Val Thr Phe Cys Arg Arg Asp Asn Gly Asp
            820                 825                 830

Gly Cys Ile Val Thr Gly Ile Thr Ser Ser Ser Ile Asp Ser Glu Gln
        835                 840                 845

Thr Ser Asp Val Thr Thr Thr Ser Ser Phe Val Ala Ser Ser Thr Pro
850                 855                 860

Thr Ser Ala Glu Gln Ser Ile Thr Asp Asn Pro Asn Ile Asp Ser Ser
865                 870                 875                 880

Gln Thr Ser Ala Ser Ser Ser Thr Lys Ser Ser Val Ser Val Ser Asp
            885                 890                 895

Thr Val Val Asn Ser Ile Leu Leu Ser Glu Thr Ser Thr Leu Ser Ser
            900                 905                 910

Asp Asp Gly Thr Ser Ser Asp Thr Ser Ile Ser Ser Thr Asn Ser
        915                 920                 925

Asp Thr Gly Asn Ile Asn Ala Gly Ser Ser His Lys Ser Thr Ala Ser
    930                 935                 940

Ile Lys Glu Ser Ser Ile Gln Lys Thr Gly Val Thr Leu Ser Ser Ser
945                 950                 955                 960

Tyr Leu Ser Thr Lys Leu Ser Ser Thr Ser Asp Ile Thr Ile Glu Leu
            965                 970                 975

Ile Thr Thr Glu Leu Thr Thr Ile Glu Asp Asn Glu Pro Asn Thr Phe
            980                 985                 990

Thr Ser Thr Pro Ser Ser His Ser  Glu Ile Phe Ser Ser  Asp Asn Ser
            995                 1000                1005

Val Leu  Ser Lys Gln Val Asp  Arg Glu Ser Thr Ile  Lys Thr Ser
    1010                1015                1020

Pro Thr  Thr Asp Val Thr Thr  Val Ser Ser Leu Ser  Val His Ser
    1025                1030                1035

Thr Glu  Ala Ser Thr Ala Thr  Leu Gly Glu Asn Ser  Phe Ser Asn
    1040                1045                1050

Val Ala  Ser Thr Pro Leu Asn  Thr Ala Thr Ser Leu  Arg Ser Thr
```

```
                        1055                1060                1065
Ser  Ser  Ser  Ser  Asn  His  Ala  Thr  Glu  Ser  Ser  Gly  Thr  Val  Lys
           1070                1075                1080

Ser  Glu  Ala  Ser  Val  Glu  Ala  Ile  Pro  Ser  Pro  Pro  Thr  Ser  Thr
      1085                1090                1095

Asp  Asn  Arg  Leu  Ser  Tyr  Ser  Thr  Glu  Glu  Ala  Glu  Gly  Ile  Thr
 1100                1105                1110

Tyr  Ala  Asn  Ser  Gly  Ser  Thr  Asn  Asn  Leu  Ile  Thr  Glu  Ser  Gln
      1115                1120                1125

Val  Ala  Ala  Pro  Thr  Asp  Ser  Thr  Ser  Val  Leu  Ile  Glu  Asn  Leu
 1130                1135                1140

Val  Val  Thr  Ser  Thr  Phe  Asp  Asp  Asn  Ser  Ser  Ala  Ala  Val  Asp
      1145                1150                1155

Gln  Pro  Ser  Lys  Thr  Lys  Ser  Ile  Glu  Glu  Ser  Ile  Met  Asn  Pro
 1160                1165                1170

Asp  Ser  Thr  Asn  Glu  Thr  Asn  Asn  Gly  Phe  Ile  Ala  Thr  Leu  Ser
      1175                1180                1185

Gln  Ala  Gln  Val  Pro  Ser  Ser  Ile  His  Ser  Glu  Leu  Ile  Ser
 1190                1195                1200

Thr  Thr  Thr  Ala  Lys  Thr  Thr  Asp  Ala  Ser  Met  Asn  Gly  Asp  Ser
      1205                1210                1215

Ala  Ala  Ser  Asn  Ser  Gln  Pro  Thr  Thr  Leu  Ile  Gln  Gln  Val  Ala
 1220                1225                1230

Thr  Ser  Ser  Tyr  Asn  Gln  Pro  Leu  Ile  Thr  Thr  Tyr  Ala  Gly  Ser
      1235                1240                1245

Ser  Ser  Ala  Thr  Lys  His  Pro  Ser  Tyr  Leu  Leu  Lys  Phe  Ile  Ser
 1250                1255                1260

Val  Ala  Leu  Phe  Phe  Phe  Leu
      1265                1270

<210> SEQ ID NO 17
<211> LENGTH: 4332
<212> TYPE: DNA
<213> ORGANISM: Candida albicans

<400> SEQUENCE: 17
atgaagaaag taatactatt acatcttttc ttctattgca cgatagcaat ggcaaaaact    60
atatcgggag ttttcacgag tttcaactca ttgacctata ctaatactgg taactaccca   120
tatgggggtc ctggttatcc aacatggact gctgttttag gttggagctt ggacggaaca   180
ctagctagtc caggtgatac atttacattg gtcatgccct gcgttttcaa atttattacc   240
acacaaactt cagtagactt aactgctaat ggtgtcaagt atgcaacatg tactttccat   300
gcaggggaag actttactac ttttcaagt atgagttgtg tagtaaataa tgggctatct   360
tcaaatatca gagcgtttgg taccgtcagg ctaccaattt cattcaatgt gggtggaact   420
ggttcatctg tcaacattca agattcaaag tgtttcactg ctggaacgaa cactgtaaca   480
tttacagacg gcgatcacaa aatttctact acagtcaatt ccctaagac tccacaatca   540 tctagtagct tggtttattt cgcaagggtt attccaagtc ttgataaatt atctagtctt   600
gttgttgctt ctcagtgtac tgctggatat gcatccggtg tgctcggatt ttcagcaaca   660
aaagatgatg tgacaattga ttgttctact atacatgtgg gaataacaaa tggtttgaat   720
agttggaata tgccagtatc atcagaatca ttttcttaca ccaaaacttg tacaccaaac   780
agttttatta ttacttatga aaatgttcct gcaggttatc gtccatttat tgattcttac   840
```

```
gtgaaaaaat cagcaacagc aacgaatgga tttaatttga attacacgaa tatatacaat      900
tgtatggatg gcaaaaaggg aaatgatcct cttatatact tttggacatc atacacaaat      960
agtgatgcag gatccaatgg agctgccgta gttgttacta cgagaacagt cactgattct     1020
acaacagcaa ttaccacatt accgtttgat cccacagttg ataaaaccaa aaccattgaa     1080
gtaatagaac ccatccctac taccactatt actacttcat atgttgggat ttctacttca     1140
ctttctacga agactgcaac tattggagga acagcaactg ttgttgttga tgttccctat     1200
catacaacta ccactatcac tagtatatgg actggatcag ctaccacatc aagtacttat     1260
acaaatccca ctgactcgat tgatacagtt gttgtacaag ttccactgcc aaatccaaca     1320
gttacaacta ctcagttttg gtcaggaagt gtgcccacaa ccgaaactgt gaccactgga     1380
ccacaaggaa cggatagtgt gatcatcaag gagccacaca ccctactgt gactaccact     1440 gagttttggt cagaatcatt tgctactact gagacagtca ccaacaatcc cgaaggcact     1500
gatagtgtga tcatcaagga accacacaat cctactgtta ccaccaccga gttttggtca     1560
gaatcatttg ctactactga cagtcacc aactatccag agggaactga ctcagtcatt     1620
gttagagaac cacacaatcc aactgtaaca acaaccgagt tttggtcaga atcatttgct     1680
actactgaga cagtcaccaa ctatccagag ggaactgact cagtcattgt tagggaacca     1740
cacaatccta ctgttaccac caccgagttt tggtcagagt catttgctac tactgagacc     1800
atcaccaact atccagaggg aactgactca gtcattgtta gggaaccaca caatccaact     1860
gtaacaacaa ccgagttttg gtcagaatca tttgtcacta ctgaaacgat aactacaggg     1920
ccacttggca ctgatagtat cgttatacat gatccattgg aagaactgtc ttctagtact     1980
gctattgagt caagtgattc taatatttca agctcagctc aagaatcatc cagtctggtt     2040
gaacagtcat tgacttctgc tgacgagact tcaagtatag ttgaattgtc atcaagatca     2100
gacattccat caagctcaat gggttaaca tctagtgagt cgtctactgt ctcaagttat     2160
gatagctact cttcaagtac tagcgaatca tctattgctt caagttatga tagctattcg     2220
tcaagtagta ttgagtcgtc tacattatct agttccgata gatgctcgtc aagtatctct     2280
gataccacaa gcttttggga ttcttcaagt tccgatttag agtccaccct gattacttgg     2340
agttcctcca tcgatgcaca atctagtcat ttggtacaat cggtatcaaa ctccatcagc     2400
acaagtcaag agttatcatc aagctcaagt gaggagtcca gtacgtttgc caccgatgct     2460
ttagtttcaa gtgatgcaag ttctattttg agctctgata cttccagtta ttacccatct     2520
agcaccattc tgtcgagtga cgattttcca cacactatag ctggggagtc agatagccta     2580
tcaatctcat ttataacatc tactgttgag atttctagtg attcggtgtc tcttacaagt     2640
gacccagcaa gcagttttga ttcatcttct agtttgaatt ctgattcatc atctctgcca     2700
tccagtgacc aaagtgatat tttgacttca tctagttttt ctacattagt tgtcccatct     2760 tttttcattga gttcaagcag ttcattatct ttgacatatc cacattatgt caactcaaca     2820
acatatcatg catcggaatc cgaaagctca tctgtcgctt caccatcaat ggcaagtgag     2880
tcagctaatg atgacacata ctttgctg gaatcactg acactacatc cagtattggc     2940
acagattctt ctactgtgac attttgtcgt cgtgataacg gagatggctg tattgtaaca     3000
gggatgccat cgtctagtat agacagtgaa cagactagtg atgtgacgac aacttctagc     3060
tttgttgctt ccagcacccc aacctcagca gaacagtcta ttactgacaa tccaaatatc     3120
gactcactgc aaacaagtgc tagttcttca actaaaattat cagtttctgt gtcagataca     3180
```

-continued

```
gtagtaaatt caatttcatt atctgaaacg tcaaccttat catctgatga cagtacttct    3240
tcggatacca gcattagctc aacaacaaac tcagatactg caatgttaa tgctgggtcg     3300 ctgcacacaa gtactgcttc catcaaagaa ctgtcaattc agaaaacggg agtaacgtta    3360
agttccagtt atttgtcgac aaaattgagt tctacgtcag atattactac tgaacttatt    3420
actactgaac ttattactac tgaacttact actactgaac ttactactat cgaagataac    3480
gaaccaaaca cttttacttc aacaccgtca agtcattctg aaatattttc tagtgataat    3540
agtgttttat caaaacaagt tgatggagaa agtactgttg aaatccctcc tgtgactgac    3600
accaccacag tatcatctgt atcagtacat tcaacagaag cttctacggc aacacttgga    3660
gaaaattcat tcagcaaagt tgccagcgct ccagtgaata ctgaaacatc tttaagatca    3720
acaagttcat catcaaatca tgctaccgaa tcagtggaa cagttaaaag tgaagcaagt     3780
gcagaagcaa ttccttctcc acctacttca actgacaaca gactaagcta ttcaactgaa    3840
gaagccaaag gtagtacata ccctaattca ggttctacaa ataacctcat gaccgaatct    3900
caagtggctg ctccaacaga ttctacttca gtgttgactg caaacccagt ggtaacttcg    3960
acgtttgatg ataagtcgtc ggcagctgtg aatcaaccaa gcaaaactaa gtcgattgaa    4020
gaatctattg gaagtcttga ttcagtcaat gaaaccaata atggatttat cgctactta    4080 tcacaatcgg aagctccaaa ttccttgatt cattcagagt caatactgac tacgatggct    4140
aaaacaactg atgcttcgat aaatggagac agtgctgctt caaactcaca gccaaccaca    4200
ttaattcaac aagtagcaac ttcctcctac aatcaacccc ttattactac ttatgccgga    4260
tcttcatccg ccactaaaca tccttcctgg ttgcttaaat ttattagcgt tgcattattc    4320
ttcttcttat ga                                                       4332
```

<210> SEQ ID NO 18
<211> LENGTH: 1443
<212> TYPE: PRT
<213> ORGANISM: Candida albicans

<400> SEQUENCE: 18

```
Met Lys Lys Val Ile Leu Leu His Leu Phe Phe Tyr Cys Thr Ile Ala
1               5                   10                  15

Met Ala Lys Thr Ile Ser Gly Val Phe Thr Ser Phe Asn Ser Leu Thr
            20                  25                  30

Tyr Thr Asn Thr Gly Asn Tyr Pro Tyr Gly Gly Pro Gly Tyr Pro Thr
        35                  40                  45

Tyr Thr Ala Val Leu Gly Tyr Ser Leu Asp Gly Thr Leu Ala Ser Pro
    50                  55                  60

Gly Asp Thr Phe Thr Leu Val Met Pro Cys Val Phe Lys Phe Ile Thr
65                  70                  75                  80

Thr Gln Thr Ser Val Asp Leu Thr Ala Asn Gly Val Lys Tyr Ala Thr
                85                  90                  95

Cys Thr Phe His Ala Gly Glu Asp Phe Thr Thr Phe Ser Ser Met Ser
            100                 105                 110

Cys Val Val Asn Asn Gly Leu Ser Ser Asn Ile Arg Ala Phe Gly Thr
        115                 120                 125

Val Arg Leu Pro Ile Ser Phe Asn Val Gly Gly Thr Gly Ser Ser Val
    130                 135                 140

Asn Ile Gln Asp Ser Lys Cys Phe Thr Ala Gly Thr Asn Thr Val Thr
145                 150                 155                 160

Phe Thr Asp Gly Asp His Lys Ile Ser Thr Thr Val Asn Phe Pro Lys
```

```
                165                 170                 175
Thr Pro Gln Ser Ser Ser Ser Leu Val Tyr Phe Ala Arg Val Ile Pro
            180                 185                 190
Ser Leu Asp Lys Leu Ser Ser Leu Val Val Ala Ser Gln Cys Thr Ala
            195                 200                 205
Gly Tyr Ala Ser Gly Val Leu Gly Phe Ser Ala Thr Lys Asp Asp Val
            210                 215                 220
Thr Ile Asp Cys Ser Thr Ile His Val Gly Ile Thr Asn Gly Leu Asn
225                 230                 235                 240
Ser Tyr Asn Met Pro Val Ser Ser Glu Ser Phe Ser Tyr Thr Lys Thr
            245                 250                 255
Cys Thr Pro Asn Ser Phe Ile Ile Thr Tyr Glu Asn Val Pro Ala Gly
            260                 265                 270
Tyr Arg Pro Phe Ile Asp Ser Tyr Val Lys Lys Ser Ala Thr Ala Thr
            275                 280                 285
Asn Gly Phe Asn Leu Asn Tyr Thr Asn Ile Tyr Asn Cys Met Asp Gly
            290                 295                 300
Lys Lys Gly Asn Asp Pro Leu Ile Tyr Phe Tyr Thr Ser Tyr Thr Asn
305                 310                 315                 320
Ser Asp Ala Gly Ser Asn Gly Ala Ala Val Val Thr Thr Arg Thr
            325                 330                 335
Val Thr Asp Ser Thr Thr Ala Ile Thr Thr Leu Pro Phe Asp Pro Thr
            340                 345                 350
Val Asp Lys Thr Lys Thr Ile Glu Val Ile Glu Pro Ile Pro Thr Thr
            355                 360                 365
Thr Ile Thr Thr Ser Tyr Val Gly Ile Ser Thr Ser Leu Ser Thr Lys
            370                 375                 380
Thr Ala Thr Ile Gly Gly Thr Ala Thr Val Val Val Asp Val Pro Tyr
385                 390                 395                 400
His Thr Thr Thr Ile Thr Ser Ile Tyr Thr Gly Ser Ala Thr Thr
            405                 410                 415
Ser Ser Thr Tyr Thr Asn Pro Thr Asp Ser Ile Asp Thr Val Val Val
            420                 425                 430
Gln Val Pro Ser Pro Asn Pro Thr Val Thr Thr Gln Phe Tyr Ser
            435                 440                 445
Gly Ser Val Pro Thr Thr Glu Thr Val Thr Thr Gly Pro Gln Gly Thr
            450                 455                 460
Asp Ser Val Ile Ile Lys Glu Pro His Asn Pro Thr Val Thr Thr Thr
465                 470                 475                 480
Glu Phe Tyr Ser Glu Ser Phe Ala Thr Thr Glu Thr Val Thr Asn Asn
            485                 490                 495
Pro Glu Gly Thr Asp Ser Val Ile Ile Lys Glu Pro His Asn Pro Thr
            500                 505                 510
Val Thr Thr Thr Glu Phe Tyr Ser Glu Ser Phe Ala Thr Thr Glu Thr
            515                 520                 525
Val Thr Asn Tyr Pro Glu Gly Thr Asp Ser Val Ile Val Arg Glu Pro
            530                 535                 540
His Asn Pro Thr Val Thr Thr Thr Glu Phe Tyr Ser Glu Ser Phe Ala
545                 550                 555                 560
Thr Thr Glu Thr Val Thr Asn Tyr Pro Glu Gly Thr Asp Ser Val Ile
            565                 570                 575
Val Arg Glu Pro His Asn Pro Thr Val Thr Thr Thr Glu Phe Tyr Ser
            580                 585                 590
```

```
Glu Ser Phe Ala Thr Thr Glu Thr Ile Thr Asn Tyr Pro Glu Gly Thr
            595                 600                 605

Asp Ser Val Ile Val Arg Glu Pro His Asn Pro Thr Val Thr Thr Thr
    610                 615                 620

Glu Phe Tyr Ser Glu Ser Phe Val Thr Thr Glu Thr Ile Thr Thr Gly
625                 630                 635                 640

Pro Leu Gly Thr Asp Ser Ile Val Ile His Asp Pro Leu Glu Ser
                645                 650                 655

Ser Ser Ser Thr Ala Ile Glu Ser Ser Asp Ser Asn Ile Ser Ser Ser
            660                 665                 670

Ala Gln Glu Ser Ser Ser Val Glu Gln Ser Leu Thr Ser Ala Asp
            675                 680                 685

Glu Thr Ser Ser Ile Val Glu Leu Ser Ser Arg Ser Asp Ile Pro Ser
    690                 695                 700

Ser Ser Ile Gly Leu Thr Ser Ser Glu Ser Ser Thr Val Ser Ser Tyr
705                 710                 715                 720

Asp Ser Tyr Ser Ser Ser Thr Ser Glu Ser Ser Ile Ala Ser Ser Tyr
                725                 730                 735

Asp Ser Tyr Ser Ser Ser Ile Glu Ser Ser Thr Leu Ser Ser Ser
                740                 745                 750

Asp Arg Cys Ser Ser Ser Ile Ser Asp Thr Thr Ser Phe Tyr Asp Ser
            755                 760                 765

Ser Ser Ser Asp Leu Glu Ser Thr Ser Ile Thr Tyr Ser Ser Ser Ile
770                 775                 780

Asp Ala Gln Ser Ser His Leu Val Gln Ser Val Ser Asn Ser Ile Ser
785                 790                 795                 800

Thr Ser Gln Glu Leu Ser Ser Ser Ser Glu Glu Ser Ser Thr Phe
            805                 810                 815

Ala Thr Asp Ala Leu Val Ser Ser Asp Ala Ser Ser Ile Leu Ser Ser
            820                 825                 830

Asp Thr Ser Ser Tyr Tyr Pro Ser Ser Thr Ile Ser Ser Ser Asp Asp
            835                 840                 845

Phe Pro His Thr Ile Ala Gly Glu Ser Asp Ser Leu Ser Ile Ser Phe
            850                 855                 860

Ile Thr Ser Thr Val Glu Ile Ser Ser Asp Ser Val Ser Leu Thr Ser
865                 870                 875                 880

Asp Pro Ala Ser Ser Phe Asp Ser Ser Ser Ser Leu Asn Ser Asp Ser
                885                 890                 895

Ser Ser Ser Pro Ser Ser Asp Gln Ser Asp Ile Leu Thr Ser Ser Ser
            900                 905                 910

Phe Ser Thr Leu Val Val Pro Ser Phe Ser Leu Ser Ser Ser Ser
            915                 920                 925

Leu Ser Leu Thr Tyr Pro His Tyr Val Asn Ser Thr Thr Tyr His Ala
    930                 935                 940

Ser Glu Ser Glu Ser Ser Ser Val Ala Ser Pro Ser Met Ala Ser Glu
945                 950                 955                 960

Ser Ala Asn Asp Asp Thr Tyr Thr Leu Ser Glu Ser Thr Asp Thr Thr
                965                 970                 975

Ser Ser Ile Gly Thr Asp Ser Ser Thr Val Thr Phe Cys Arg Arg Asp
            980                 985                 990

Asn Gly Asp Gly Cys Ile Val Thr  Gly Met Pro Ser Ser  Ser Ile Asp
            995                 1000                1005
```

```
Ser Glu Gln Thr Ser Asp Val Thr Thr Thr Ser Ser Phe Val Ala
    1010                1015                1020

Ser Ser Thr Pro Thr Ser Ala Glu Gln Ser Ile Thr Asp Asn Pro
    1025                1030                1035

Asn Ile Asp Ser Ser Gln Thr Ser Ala Ser Ser Ser Thr Lys Leu
    1040                1045                1050

Ser Val Ser Val Ser Asp Thr Val Val Asn Ser Ile Ser Leu Ser
    1055                1060                1065

Glu Thr Ser Thr Leu Ser Ser Asp Asp Ser Thr Ser Ser Asp Thr
    1070                1075                1080

Ser Ile Ser Ser Thr Thr Asn Ser Asp Thr Gly Asn Val Asn Ala
    1085                1090                1095

Gly Ser Ser His Thr Ser Thr Ala Ser Ile Lys Glu Ser Ser Ile
    1100                1105                1110

Gln Lys Thr Gly Val Thr Leu Ser Ser Ser Tyr Leu Ser Thr Lys
    1115                1120                1125

Leu Ser Ser Thr Ser Asp Ile Thr Thr Glu Leu Ile Thr Thr Glu
    1130                1135                1140

Leu Ile Thr Thr Glu Leu Thr Thr Thr Glu Leu Thr Thr Ile Glu
    1145                1150                1155

Asp Asn Glu Pro Asn Thr Phe Thr Ser Thr Pro Ser Ser His Ser
    1160                1165                1170

Glu Ile Phe Ser Ser Asp Asn Ser Val Leu Ser Lys Gln Val Asp
    1175                1180                1185

Gly Glu Ser Thr Val Glu Ile Pro Pro Val Thr Asp Thr Thr Thr
    1190                1195                1200

Val Ser Ser Val Ser Val His Ser Thr Glu Ala Ser Thr Ala Thr
    1205                1210                1215

Leu Gly Glu Asn Ser Phe Ser Lys Val Ala Ser Ala Pro Val Asn
    1220                1225                1230

Thr Glu Thr Ser Leu Arg Ser Thr Ser Ser Ser Ser Asn His Ala
    1235                1240                1245

Thr Glu Ser Ser Gly Thr Val Lys Ser Glu Ala Ser Ala Glu Ala
    1250                1255                1260

Ile Pro Ser Pro Pro Thr Ser Thr Asp Asn Arg Leu Ser Tyr Ser
    1265                1270                1275

Thr Glu Glu Ala Lys Gly Ser Thr Tyr Pro Asn Ser Gly Ser Thr
    1280                1285                1290

Asn Asn Leu Met Thr Glu Ser Gln Val Ala Ala Pro Thr Asp Ser
    1295                1300                1305

Thr Ser Val Leu Thr Ala Asn Pro Val Val Thr Ser Thr Phe Asp
    1310                1315                1320

Asp Lys Ser Ser Ala Ala Val Asn Gln Pro Ser Lys Thr Lys Ser
    1325                1330                1335

Ile Glu Glu Ser Ile Gly Ser Leu Asp Ser Val Asn Glu Thr Asn
    1340                1345                1350

Asn Gly Phe Ile Ala Thr Leu Ser Gln Ser Glu Ala Pro Asn Ser
    1355                1360                1365

Leu Ile His Ser Glu Ser Ile Ser Thr Thr Met Ala Lys Thr Thr
    1370                1375                1380

Asp Ala Ser Ile Asn Gly Asp Ser Ala Ala Ser Asn Ser Gln Pro
    1385                1390                1395

Thr Thr Leu Ile Gln Gln Val Ala Thr Ser Ser Tyr Asn Gln Pro
```

|  | 1400 | 1405 | | 1410 | |
|---|---|---|---|---|---|

Leu Ile Thr Thr Tyr Ala Gly Ser Ser Ala Thr Lys His Pro
    1415                1420                    1425

Ser Tyr Leu Leu Lys Phe Ile Ser Val Ala Leu Phe Phe Phe Leu
    1430                1435                    1440

<210> SEQ ID NO 19
<211> LENGTH: 6897
<212> TYPE: DNA
<213> ORGANISM: Candida albicans

<400> SEQUENCE: 19

```
atgaagaaac tatatctttt atatttgttg gccctgttta caacggtcat atccaaagaa      60
gttactggtg ttttcaacca attcaattca ttgatatggt cttacacata cagagctcga     120
tacgaagaaa tatctactct taccgctaat gctcaattgg aatgggcttt ggatggtact     180
attgccagtc ccggtgatac atttacatta gtcatgccct gtgtatataa attcatgacg     240
tacgaaacct cagtgcaatt aactgccaac tctattgcat atgccacatg tgactttgat     300
gctggtgaag acactaaaag tttttcaagt ttgaagtgta cggtgactga tgagttgaca     360
gaagatacca gcgttttggg aagtgttatt ttgcctattg ctttcaatgt ggaggttcc      420
ggatctaaat ctacgataac agactccaaa tgttttttca agtgggtacaa cactgtcacg     480
tttttttgacg aaacaatca actttctaca actgcaaatt ttcttcccg aagaaacta      540
gcgtttggtc tagttgttag tcaaagactt tccatgtcgc tcgatacaat gactaatttt     600
gttatgtcta caccttgttt catgggttat cagctgggta agttaggttt tacatctaat     660
gatgatgatt ttgaaattga ttgttcttct atacatgttg gtataactaa tgaaataaat     720
gattggagta tgccagtatc ttctgttccc ttcgatcata ctataagatg tacatcacgt     780
gcactttaca ttgagtttaa acaattcct gcaggttatc gaccttttgt ggatgcgatt      840
gttcaaatac caacgacaga acctttttt gtaaaatata caaatgagtt tgcctgtgtg      900
aatggcatat acacgtccat acctttcaca gtttctttt ctcagccaat tttatatgac     960
gaggctttag ctattggtgc agacctagtt cgtaccacat ccacagtgat aggttccatt    1020
accagaacta ccacattacc cttcatttcc cgactccaga aaaccaaaac aattctagtc    1080
ttagagccca tacccaccac tacggtaaca acttcacacc atggctttga acttggtat     1140
tatactaaga aagccaccat tggtgacaca gctactgttt tcattgatgt tccacaacat    1200
acagctacta ctttgaccac atattggcaa gaatcaagta cagcgacaac cacttacttc    1260
gatgacatag acttggtcga tactgtcatt gtgaaaattc catatcccaa tccgactatt    1320
ataacaacac aattttggtc aggtaaatat ttaactactg agacacacaa agaaccacct    1380
ctcggtactg atagtgtgat catcaaggaa ccacacaacc ctactgtgac aacgaccgag    1440
ttttggtcag aatcatttgc cactactgag accatcacca actatccaga aggcactgac    1500
tcagtcattg ttagggaacc acacaaccct actgtgacaa cgaccgagtt ttggtcagaa    1560
tcatttgcca ctactgagac catcaccaac ggtccagaag gcactgactc agtcattgtt    1620
agggaaccac ataatccaac tgtgacaaca ccgagttttt ggtcagaatc atttgccact    1680
actgagacca tcaccaacgg tccagaaggc actgactcag tcattgttag ggaaccacac    1740
aatccaactg tgcaacaac cgagtttttg tcagaatcat tgccactac tgagaccatc     1800
accaacggtc cagaaggcac tgactcagtc attgttaggg aaccacataa tccaactgtg    1860
acaacaaccg agttttggtc agaatcattt gccactactg agaccatcac caacggtcca    1920
```

```
gaaggcactg atagtgtgat catcaaggaa ccacacaacc ctactgtgac taccaccaag    1980
ttttggtcag aatcatttgc cactactgag acaatcacca actatccaga aggcactgac    2040
tcagtcattg ttagggaacc acataatcca actgtgacaa caaccgagtt ttggtcagaa    2100
tcatttgcca ctactgagac catcaccaac ggtccagaag gcactgactc agtcattgtt    2160
agggaaccac acaatccaac tgtgacaaca accgagtttt ggtcagaatc atttgctact    2220
actgagacca tcaccaacta tccagaggga actgactcag tcattgttag agaaccacac    2280
aatccaactg taacaacaac cgagttttgg tcagagtcat tgctactac tgagacagtc    2340 accaactatc agaaggcac tgactcagtc attgttaggg aaccacacaa tccaactgtg    2400
acaacaaccg agttttggtc agaatcattt gtcactactg aaacgataac tacagggcca    2460
cttggcactg atagtatcgt tatacatgat ccattggaag aactgtcttc tagtactgct    2520
attgagtcaa gtgattctaa tatttcaagc tcagctcaag aatcatccag tctggttgaa    2580
cagtcattta cttctgctga cgagacttca agtatagttg aattgtcatc aagatcagac    2640
attccatcaa gctcaattgg gttaacatct agtgagtcgt ctactgtctc aagttatgat    2700
agctactctt caagtactag cgaatcatct attgcttcaa gttatgatag ctattcgtca    2760
agtagtattg agtcgtctac tttatctagt tccgatagat actcgtcaag tatctctgat    2820
accacaagct tttgggattc ttcaagttcc gatttagagt ccaccctgat tacttggagt    2880
tcctccatcg atgcacaatc tagtcatttg gtacaatcgg tatcaaactc catcagcaca    2940
agtcaagaga tatcatcaag ctcaagtgag gagtccagta cgtctgccac cgatgcttta    3000
gtttcaagtg atgcaagttc tattttgagc tctgatactt ccagttatta cccatctagc    3060
accattctgc cgagtgacga ttttccacac actatagctg gggagtcaga tagccaatca    3120
atctcattta taacatctac tgttgagatt tctagtgatt cggtgtctct tacaagtgac    3180
ccagaaagca gttttgattc atcttctcgt ttgaattctg attcatcatc tctgccatcc    3240
actgaccaaa gggatatttt gacttcatct agttttttcta cattaattaa atcaagtggg    3300
tcacgtgaat ccagtattgg tacaattttg agtgaagaaa gcagtgactc gattccaacg    3360
acgttctcaa caagatattg gtcgccatcg ggaatgagtt ccagacatta taccaattcg    3420
acagagacgc tggtctcaga tgttgttctg tcgtcggttg ctggagacga aactagtgaa    3480
tcgagtgttt cggttattag tgaatcgagt gaatcagtta ccagtgaatc agttgccagt    3540
gaatcagttg ccagtgaatc agttgccagt gaatcagttg ccagtgaatc agttactgct    3600
gtgagtgata tttcagattt gtacactacg tcagaagagg tatccactag tgacagcaac    3660
tctggtatga gctctcctat accatcgagt gaacagagat ccagtattcc gataatgtcg    3720
agctccgacg aatcaagtga gtcacgtgag tccagtagtg gtacaatttt gagtgaagaa    3780
aacagtgact cgattccaac gacgttctca acaagatatt ggtcgccatc gggaatgagt    3840
tccagacatt ataccaattc gacagagacg ctggtctcag atgttgttct gtcgtcggtt    3900
gctggagacg aaactagtga atcgagtgtt tcggttatta gtgaatcgag tgaatcagtt    3960
accagtgaat cagttgccag tgaatcagtt gccagtgaat cagttgccag tgaatcagtt    4020
actgctgtga gtgatatttc agatttgtac actacgtcag aagtggtatc cactagtgac    4080
agcaactctg gtatgagctc tcctatacca tcgagtgaac agagatccag tattccggta    4140
atgtcaagct ccgacgaatc aagtgagtca cgtgagtcca gtagtggtac aattttgagt    4200
gaagaaaaca gtgactcgat cccaacgacg ttctcaacaa gatatttgtc accatcggga    4260
```

```
atgagttcca gacattatac caattcgaca gagacgctgg tctcagatgt tgttctgtcg    4320
tcggttgctg gagacgaaac tagtgaatcg agtgtttcgg ttattagtga atcgagtgaa    4380
tcagttacca gtgaatcagt tgccagtgaa tcagttgcca gtgaatcagt tgccagtgaa    4440
tcagttactg ctgtgagtga tatttcagat ttgtacacta cgtcagaagt ggtatccact    4500
agtgacagta aaatagttgc aagtacttct gtaccatcga gtgaacagag atccagtatt    4560
ccgataatgt cgagctccga cgaatcaagt gagtcacgtg agtccagtag tggtacaatt    4620
ttgagtgaag aaaacagtga ctcgattcca acgacgttct caacaagata ttggtcgcca    4680
tcgggaatga gttccagaca ttataccaat tcgacagaga cgctggtctc agatgttgtt    4740
ctgtcgtcgg ttgctggaga cgaaactagt gaatcgagtg tttcggttat tagtgaatcg    4800
agtgaatcag ttaccagtga atcagttgcc agtgaatcag ttgccagtga atcagttact    4860
gctgtgagtg atatttcaga tttgtacact acgtcagaag tggtatccac tagtgacagt    4920
aaaatagttc caagtacttc tgtaccatcg agtgaacaga gatccagtat tccgataatg    4980
tcgagctccg acgaatcaag tgagtcacgt gagtccagta gtggtacaat tttgagtgaa    5040
gaaaacagtg actcgatccc aacgacgttc tcaacaagat attggtcgcc atcgggaatg    5100
agttccagac attataccaa ttcgacagag acgctggtct cagatgttgt tctgtcgtcg    5160
gttgctggag acgaaactag tgaatcaagt gtttcggtta ctagtgaatc gagtgaatca    5220
gttaccagtg aatcagttgc cagtgaatca gttgccagtg aatcagttgc cagtgaatca    5280
gttactgctg tgagtgatat ttcagatttg tacactacgt cagaagtggt atccactagt    5340
gacagcaact ctggtatgag ccctcctata ccatcgagtg aacagagatc cagtattccg    5400
gtaatgtcaa gctccaacga atcaagtgag tcacgtgagt ccagtagtgg tacaattttg    5460
agtgaagaaa acagtgactc gatcccaacg acgttctcaa caagatatgt gtcggtttct    5520
cttaccgtgg gggaactttc ggcattacct agtttgcctg gaaaattatc tcatttacca    5580
tccagtttgt ctgaaacgtc catcggaatg acaaaaagtg ctaatttgct gccacagttt    5640
ttttcaacat cagttgattc agctttactg tattgggctc tgggctctag cagtgctgat    5700
caccagagtt ctgctacgtg tgatgttagt gaatcatctg tggaaggtaa tttgtctgca    5760
atggcaccag ggatgtcgaa ttcagatgat ggtttgtcag aggatacaag atcatcttcg    5820
gttgccggta agaggagat agagttaact ctgacgaatt ctgttggtga aatcacccctt    5880 ataagctata gttcttcctc gcctacgacc catgaccacg ggcgtgtgtc aaagagcatg    5940
ggggcggcac cacttagtag tttattctca gtatcagtac atactccact agttactggg    6000
ctactgggtt ctgatacttt tccaagtgaa aattcaaatc ggagtcgttc atttaaggag    6060
tctacagaca atactatttc catatcgaga gaatctttgg gaaatccata ttcatcaata    6120
tcctcacctt ccgattatga cgtgaaactg ttcacgacgt ccagagagct agtatcttca    6180
gaatctatac taccattttc agatgtaatg gatgcaaatg atatgccgac atctggaagt    6240
aatttgcact ctatggtgtt ttcaatatct gtgctaggcg aaaaatttaa tgctaatata    6300
gagaagcata aaaacactaa tgggcattat tcatcaatgg tatttactta tcaaagtgca    6360
ggtttggaag agtcagacca gaggatagct gttactaata ctaaattcga ccaaaataaa    6420
attgacacaa caattgacag caatactttt gttacgagtt tgccattcgc cactacttca    6480
aacgaccaaa ttgatcaagc tgtaccaatt aagattccgg catcttctac agcaggattt    6540
gtctctgatg tactcaagcc agattattcg aaatctgtcc aggctgaatc tgtccaaact    6600
gattcaacaa cttattcaga aatgatgtca agtaaaagaa acaagaattc aggctttggg    6660
```

```
acaagctcac tcattttgaa gcctaccatt actgtcgtca ctaagtctat tgatactaaa    6720
gttaatacta tgaaagaggg tggggtttcc aaacaagttt caacgactgt gactgaacaa    6780
tatgacacct ctacctacac tccagcaagt ttgcttgtgt ctgataatct ggggtcagtt    6840
tccaaatatt ctctttggat gatggcattt tatatgttat ttggattgtt ttaataa       6897
```

<210> SEQ ID NO 20
<211> LENGTH: 2297
<212> TYPE: PRT
<213> ORGANISM: Candida albicans

<400> SEQUENCE: 20

```
Met Lys Lys Leu Tyr Leu Leu Tyr Leu Leu Ala Ser Phe Thr Thr Val
1               5                   10                  15

Ile Ser Lys Glu Val Thr Gly Val Phe Asn Gln Phe Asn Ser Leu Ile
            20                  25                  30

Tyr Ser Tyr Thr Tyr Arg Ala Arg Tyr Glu Glu Ile Ser Thr Leu Thr
        35                  40                  45

Ala Asn Ala Gln Leu Glu Tyr Ala Leu Asp Gly Thr Ile Ala Ser Pro
    50                  55                  60

Gly Asp Thr Phe Thr Leu Val Met Pro Cys Val Tyr Lys Phe Met Thr
65                  70                  75                  80

Tyr Glu Thr Ser Val Gln Leu Thr Ala Asn Ser Ile Ala Tyr Ala Thr
                85                  90                  95

Cys Asp Phe Asp Ala Gly Glu Asp Thr Lys Ser Phe Ser Ser Leu Lys
            100                 105                 110

Cys Thr Val Thr Asp Glu Leu Thr Glu Asp Thr Ser Val Phe Gly Ser
        115                 120                 125

Val Ile Leu Pro Ile Ala Phe Asn Val Gly Gly Ser Gly Ser Lys Ser
    130                 135                 140

Thr Ile Thr Asp Ser Lys Cys Phe Ser Ser Gly Tyr Asn Thr Val Thr
145                 150                 155                 160

Phe Phe Asp Gly Asn Asn Gln Leu Ser Thr Thr Ala Asn Phe Leu Pro
                165                 170                 175

Arg Arg Glu Leu Ala Phe Gly Leu Val Val Ser Gln Arg Leu Ser Met
            180                 185                 190

Ser Leu Asp Thr Met Thr Asn Phe Val Met Ser Thr Pro Cys Phe Met
        195                 200                 205

Gly Tyr Gln Ser Gly Lys Leu Gly Phe Thr Ser Asn Asp Asp Asp Phe
    210                 215                 220

Glu Ile Asp Cys Ser Ser Ile His Val Gly Ile Thr Asn Glu Ile Asn
225                 230                 235                 240

Asp Tyr Ser Met Pro Val Ser Ser Val Pro Phe Asp His Thr Ile Arg
                245                 250                 255

Cys Thr Ser Arg Ala Leu Tyr Ile Glu Phe Lys Thr Ile Pro Ala Gly
            260                 265                 270

Tyr Arg Pro Phe Val Asp Ala Ile Val Gln Ile Pro Thr Thr Glu Pro
        275                 280                 285

Phe Phe Val Lys Tyr Thr Asn Glu Phe Ala Cys Val Asn Gly Ile Tyr
    290                 295                 300

Thr Ser Ile Pro Phe Ser Phe Phe Ser Gln Pro Ile Leu Tyr Asp
305                 310                 315                 320

Glu Ala Leu Ala Ile Gly Ala Asp Leu Val Arg Thr Thr Ser Thr Val
                325                 330                 335
```

-continued

```
Ile Gly Ser Ile Thr Arg Thr Thr Leu Pro Phe Ile Ser Arg Leu
            340                 345                 350

Gln Lys Thr Lys Thr Ile Leu Val Leu Glu Pro Ile Pro Thr Thr Thr
                355                 360                 365

Val Thr Thr Ser His His Gly Phe Asp Thr Tyr Tyr Tyr Thr Lys Lys
370                 375                 380

Ala Thr Ile Gly Asp Thr Ala Thr Val Phe Ile Asp Val Pro Gln His
385                 390                 395                 400

Thr Ala Thr Thr Leu Thr Thr Tyr Tyr Gln Glu Ser Ser Thr Ala Thr
                405                 410                 415

Thr Thr Tyr Phe Asp Asp Ile Asp Leu Val Asp Thr Val Ile Val Lys
            420                 425                 430

Ile Pro Tyr Pro Asn Pro Thr Ile Ile Thr Thr Gln Phe Tyr Ser Gly
        435                 440                 445

Lys Tyr Leu Thr Thr Glu Thr His Lys Glu Pro Pro Leu Gly Thr Asp
    450                 455                 460

Ser Val Ile Ile Lys Glu Pro His Asn Pro Thr Val Thr Thr Thr Glu
465                 470                 475                 480

Phe Tyr Ser Glu Ser Phe Ala Thr Thr Glu Thr Ile Thr Asn Tyr Pro
                485                 490                 495

Glu Gly Thr Asp Ser Val Ile Val Arg Glu Pro His Asn Pro Thr Val
            500                 505                 510

Thr Thr Thr Glu Phe Tyr Ser Glu Ser Phe Ala Thr Thr Glu Thr Ile
        515                 520                 525

Thr Asn Gly Pro Glu Gly Thr Asp Ser Val Ile Val Arg Glu Pro His
    530                 535                 540

Asn Pro Thr Val Thr Thr Thr Glu Phe Tyr Ser Glu Ser Phe Ala Thr
545                 550                 555                 560

Thr Glu Thr Ile Thr Asn Gly Pro Glu Gly Thr Asp Ser Val Ile Val
                565                 570                 575

Arg Glu Pro His Asn Pro Thr Val Thr Thr Thr Glu Phe Tyr Ser Glu
            580                 585                 590

Ser Phe Ala Thr Thr Glu Thr Ile Thr Asn Gly Pro Glu Gly Thr Asp
        595                 600                 605

Ser Val Ile Val Arg Glu Pro His Asn Pro Thr Val Thr Thr Thr Glu
    610                 615                 620

Phe Tyr Ser Glu Ser Phe Ala Thr Thr Glu Thr Ile Thr Asn Gly Pro
625                 630                 635                 640

Glu Gly Thr Asp Ser Val Ile Ile Lys Glu Pro His Asn Pro Thr Val
                645                 650                 655

Thr Thr Thr Lys Phe Tyr Ser Glu Ser Phe Ala Thr Thr Glu Thr Ile
            660                 665                 670

Thr Asn Tyr Pro Glu Gly Thr Asp Ser Val Ile Val Arg Glu Pro His
        675                 680                 685

Asn Pro Thr Val Thr Thr Thr Glu Phe Tyr Ser Glu Ser Phe Ala Thr
    690                 695                 700

Thr Glu Thr Ile Thr Asn Gly Pro Glu Gly Thr Asp Ser Val Ile Val
705                 710                 715                 720

Arg Glu Pro His Asn Pro Thr Val Thr Thr Thr Glu Phe Tyr Ser Glu
                725                 730                 735

Ser Phe Ala Thr Thr Glu Thr Ile Thr Asn Tyr Pro Glu Gly Thr Asp
            740                 745                 750
```

```
Ser Val Ile Val Arg Glu Pro His Asn Pro Thr Val Thr Thr Glu
        755                 760                 765

Phe Tyr Ser Glu Ser Phe Ala Thr Thr Glu Thr Val Thr Asn Tyr Pro
        770                 775                 780

Glu Gly Thr Asp Ser Val Ile Val Arg Glu Pro His Asn Pro Thr Val
785                 790                 795                 800

Thr Thr Thr Glu Phe Tyr Ser Glu Ser Phe Val Thr Glu Thr Ile
                805                 810                 815

Thr Thr Gly Pro Leu Gly Thr Asp Ser Ile Val Ile His Asp Pro Leu
            820                 825                 830

Glu Glu Ser Ser Ser Ser Thr Ala Ile Glu Ser Ser Asp Ser Asn Ile
        835                 840                 845

Ser Ser Ser Ala Gln Glu Ser Ser Ser Val Glu Gln Ser Phe Thr
        850                 855                 860

Ser Ala Asp Glu Thr Ser Ser Ile Val Glu Leu Ser Ser Arg Ser Asp
865                 870                 875                 880

Ile Pro Ser Ser Ser Ile Gly Leu Thr Ser Ser Glu Ser Ser Thr Val
            885                 890                 895

Ser Ser Tyr Asp Ser Tyr Ser Ser Thr Ser Glu Ser Ser Ile Ala
        900                 905                 910

Ser Ser Tyr Asp Ser Tyr Ser Ser Ser Ile Glu Ser Ser Thr Leu
        915                 920                 925

Ser Ser Ser Asp Arg Tyr Ser Ser Ile Ser Asp Thr Thr Ser Phe
930                 935                 940

Tyr Asp Ser Ser Ser Asp Leu Glu Ser Thr Ser Ile Thr Tyr Ser
945                 950                 955                 960

Ser Ser Ile Asp Ala Gln Ser Ser His Leu Val Gln Ser Val Ser Asn
            965                 970                 975

Ser Ile Ser Thr Ser Gln Glu Ile Ser Ser Ser Ser Glu Glu Ser
            980                 985                 990

Ser Thr Ser Ala Thr Asp Ala Leu Val Ser Ser Asp Ala Ser Ser Ile
        995                 1000                1005

Leu Ser Ser Asp Thr Ser Ser Tyr Tyr Pro Ser Ser Thr Ile Ser
    1010                1015                1020

Pro Ser Asp Asp Phe Pro His Thr Ile Ala Gly Glu Ser Asp Ser
    1025                1030                1035

Gln Ser Ile Ser Phe Ile Thr Ser Thr Val Glu Ile Ser Ser Asp
    1040                1045                1050

Ser Val Ser Leu Thr Ser Asp Pro Glu Ser Ser Phe Asp Ser Ser
    1055                1060                1065

Ser Arg Leu Asn Ser Asp Ser Ser Ser Ser Pro Ser Thr Asp Gln
    1070                1075                1080

Arg Asp Ile Leu Thr Ser Ser Phe Ser Thr Leu Ile Lys Ser
    1085                1090                1095

Ser Gly Ser Arg Glu Ser Ser Ile Gly Thr Ile Leu Ser Glu Glu
    1100                1105                1110

Ser Ser Asp Ser Ile Pro Thr Thr Phe Ser Thr Arg Tyr Tyr Ser
    1115                1120                1125

Pro Ser Gly Met Ser Ser Arg His Tyr Thr Asn Ser Thr Glu Thr
    1130                1135                1140

Ser Val Ser Asp Val Val Ser Ser Ser Val Ala Gly Asp Glu Thr
    1145                1150                1155

Ser Glu Ser Ser Val Ser Val Ile Ser Glu Ser Ser Glu Ser Val
```

```
                1160                1165                1170
Thr Ser Glu Ser Val Ala Ser Glu Ser Val Ala Ser Glu Ser Val
    1175                1180                1185
Ala Ser Glu Ser Val Ala Ser Glu Ser Val Thr Ala Val Ser Asp
    1190                1195                1200
Ile Ser Asp Leu Tyr Thr Thr Ser Glu Glu Val Ser Thr Ser Asp
    1205                1210                1215
Ser Asn Ser Gly Met Ser Ser Pro Ile Pro Ser Ser Glu Gln Arg
    1220                1225                1230
Ser Ser Ile Pro Ile Met Ser Ser Ser Asp Glu Ser Ser Glu Ser
    1235                1240                1245
Arg Glu Ser Ser Ser Gly Thr Ile Leu Ser Glu Glu Asn Ser Asp
    1250                1255                1260
Ser Ile Pro Thr Thr Phe Ser Thr Arg Tyr Tyr Ser Pro Ser Gly
    1265                1270                1275
Met Ser Ser Arg His Tyr Thr Asn Ser Thr Glu Thr Ser Val Ser
    1280                1285                1290
Asp Val Val Ser Ser Ser Val Ala Gly Asp Glu Thr Ser Glu Ser
    1295                1300                1305
Ser Val Ser Val Ile Ser Glu Ser Ser Glu Ser Val Thr Ser Glu
    1310                1315                1320
Ser Val Ala Ser Glu Ser Val Ala Ser Glu Ser Val Ala Ser Glu
    1325                1330                1335
Ser Val Thr Ala Val Ser Asp Ile Ser Asp Leu Tyr Thr Thr Ser
    1340                1345                1350
Glu Val Val Ser Thr Ser Asp Ser Asn Ser Gly Met Ser Ser Pro
    1355                1360                1365
Ile Pro Ser Ser Glu Gln Arg Ser Ser Ile Pro Val Met Ser Ser
    1370                1375                1380
Ser Asp Glu Ser Ser Glu Ser Arg Glu Ser Ser Ser Gly Thr Ile
    1385                1390                1395
Leu Ser Glu Glu Asn Ser Asp Ser Ile Pro Thr Thr Phe Ser Thr
    1400                1405                1410
Arg Tyr Leu Ser Pro Ser Gly Met Ser Ser Arg His Tyr Thr Asn
    1415                1420                1425
Ser Thr Glu Thr Ser Val Ser Asp Val Val Ser Ser Ser Val Ala
    1430                1435                1440
Gly Asp Glu Thr Ser Glu Ser Ser Val Ser Val Ile Ser Glu Ser
    1445                1450                1455
Ser Glu Ser Val Thr Ser Glu Ser Val Ala Ser Glu Ser Val Ala
    1460                1465                1470
Ser Glu Ser Val Ala Ser Glu Ser Val Thr Ala Val Ser Asp Ile
    1475                1480                1485
Ser Asp Leu Tyr Thr Thr Ser Glu Val Val Ser Thr Ser Asp Ser
    1490                1495                1500
Lys Ile Val Ala Ser Thr Ser Val Pro Ser Ser Glu Gln Arg Ser
    1505                1510                1515
Ser Ile Pro Ile Met Ser Ser Ser Asp Glu Ser Ser Glu Ser Arg
    1520                1525                1530
Glu Ser Ser Ser Gly Thr Ile Leu Ser Glu Glu Asn Ser Asp Ser
    1535                1540                1545
Ile Pro Thr Thr Phe Ser Thr Arg Tyr Tyr Ser Pro Ser Gly Met
    1550                1555                1560
```

-continued

Ser Ser Arg His Tyr Thr Asn Ser Thr Glu Thr Ser Val Ser Asp
    1565                1570                1575

Val Val Ser Ser Ser Val Ala Gly Asp Glu Thr Ser Glu Ser Ser
    1580                1585                1590

Val Ser Val Ile Ser Glu Ser Ser Glu Ser Val Thr Ser Glu Ser
    1595                1600                1605

Val Ala Ser Glu Ser Val Ala Ser Glu Ser Val Thr Ala Val Ser
    1610                1615                1620

Asp Ile Ser Asp Leu Tyr Thr Thr Ser Glu Val Val Ser Thr Ser
    1625                1630                1635

Asp Ser Lys Ile Val Pro Ser Thr Ser Val Pro Ser Ser Glu Gln
    1640                1645                1650

Arg Ser Ser Ile Pro Ile Met Ser Ser Ser Asp Glu Ser Ser Glu
    1655                1660                1665

Ser Arg Glu Ser Ser Ser Gly Thr Ile Leu Ser Glu Glu Asn Ser
    1670                1675                1680

Asp Ser Ile Pro Thr Thr Phe Ser Thr Arg Tyr Tyr Ser Pro Ser
    1685                1690                1695

Gly Met Ser Ser Arg His Tyr Thr Asn Ser Thr Glu Thr Ser Val
    1700                1705                1710

Ser Asp Val Val Ser Ser Ser Val Ala Gly Asp Glu Thr Ser Glu
    1715                1720                1725

Ser Ser Val Ser Val Thr Ser Glu Ser Ser Glu Ser Val Thr Ser
    1730                1735                1740

Glu Ser Val Ala Ser Glu Ser Val Ala Ser Glu Ser Val Ala Ser
    1745                1750                1755

Glu Ser Val Thr Ala Val Ser Asp Ile Ser Asp Leu Tyr Thr Thr
    1760                1765                1770

Ser Glu Val Val Ser Thr Ser Asp Ser Asn Ser Gly Met Ser Pro
    1775                1780                1785

Pro Ile Pro Ser Ser Glu Gln Arg Ser Ser Ile Pro Val Met Ser
    1790                1795                1800

Ser Ser Asn Glu Ser Ser Glu Ser Arg Glu Ser Ser Ser Gly Thr
    1805                1810                1815

Ile Leu Ser Glu Glu Asn Ser Asp Ser Ile Pro Thr Thr Phe Ser
    1820                1825                1830

Thr Arg Tyr Val Ser Val Ser Leu Thr Val Gly Glu Leu Ser Ala
    1835                1840                1845

Leu Pro Ser Leu Pro Gly Lys Leu Ser His Leu Pro Ser Ser Leu
    1850                1855                1860

Ser Glu Thr Ser Ile Gly Met Thr Lys Ser Ala Asn Leu Ser Pro
    1865                1870                1875

Gln Phe Phe Ser Thr Ser Val Asp Ser Ala Leu Ser Tyr Tyr Ala
    1880                1885                1890

Ser Gly Ser Ser Ser Ala Asp His Gln Ser Ser Ala Thr Cys Asp
    1895                1900                1905

Val Ser Glu Ser Ser Val Glu Gly Asn Leu Ser Ala Met Ala Pro
    1910                1915                1920

Gly Met Ser Asn Ser Asp Asp Gly Leu Ser Glu Asp Thr Arg Ser
    1925                1930                1935

Ser Ser Val Ala Gly Lys Glu Glu Ile Glu Leu Thr Ser Thr Asn
    1940                1945                1950

```
Ser Val Gly Glu Ile Thr Leu Ile Ser Tyr Ser Ser Ser Ser Pro
    1955            1960            1965

Thr Thr His Asp His Gly Arg Val Ser Lys Ser Met Gly Ala Ala
    1970            1975            1980

Pro Leu Ser Ser Leu Phe Ser Val Ser Val His Thr Pro Leu Val
    1985            1990            1995

Thr Gly Leu Ser Gly Ser Asp Thr Phe Pro Ser Glu Asn Ser Asn
    2000            2005            2010

Arg Ser Arg Ser Phe Lys Glu Ser Thr Asp Asn Thr Ile Ser Ile
    2015            2020            2025

Ser Arg Glu Ser Leu Gly Asn Pro Tyr Ser Ser Ile Ser Ser Pro
    2030            2035            2040

Ser Asp Tyr Asp Val Lys Ser Phe Thr Thr Ser Arg Glu Leu Val
    2045            2050            2055

Ser Ser Glu Ser Ile Leu Pro Phe Ser Asp Val Met Asp Ala Asn
    2060            2065            2070

Asp Met Pro Thr Ser Gly Ser Asn Leu His Ser Met Val Phe Ser
    2075            2080            2085

Ile Ser Val Leu Gly Glu Lys Phe Asn Ala Asn Ile Glu Lys His
    2090            2095            2100

Lys Asn Thr Asn Gly His Tyr Ser Ser Met Val Phe Thr Tyr Gln
    2105            2110            2115

Ser Ala Gly Leu Glu Glu Ser Asp Gln Arg Ile Ala Val Thr Asn
    2120            2125            2130

Thr Lys Phe Asp Gln Asn Lys Ile Asp Thr Thr Ile Asp Ser Asn
    2135            2140            2145

Thr Phe Val Thr Ser Leu Pro Phe Ala Thr Thr Ser Asn Asp Gln
    2150            2155            2160

Ile Asp Gln Ala Val Pro Ile Lys Ile Pro Ala Ser Ser Thr Ala
    2165            2170            2175

Gly Phe Val Ser Asp Val Leu Lys Pro Asp Tyr Ser Lys Ser Val
    2180            2185            2190

Gln Ala Glu Ser Val Gln Thr Asp Ser Thr Thr Tyr Ser Glu Met
    2195            2200            2205

Met Ser Ser Lys Arg Asn Lys Asn Ser Gly Phe Gly Thr Ser Ser
    2210            2215            2220

Leu Ile Leu Lys Pro Thr Ile Thr Val Val Thr Lys Ser Ile Asp
    2225            2230            2235

Thr Lys Val Asn Thr Met Lys Glu Gly Gly Val Ser Lys Gln Val
    2240            2245            2250

Ser Thr Thr Val Thr Glu Gln Tyr Asp Thr Ser Thr Tyr Thr Pro
    2255            2260            2265

Ala Ser Leu Leu Val Ser Asp Asn Ser Gly Ser Val Ser Lys Tyr
    2270            2275            2280

Ser Leu Tyr Met Met Ala Phe Tyr Met Leu Phe Gly Leu Phe
    2285            2290            2295
```

<210> SEQ ID NO 21
<211> LENGTH: 4383
<212> TYPE: DNA
<213> ORGANISM: Candida albicans

<400> SEQUENCE: 21
ataataagac aaaataaaa agaacaacaa aattatgagc caaacaatcc gaagcaacgt    60

```
aaagtacgat atcaaagaat cataactttg ctttctattt gataacccgc ctcaaatcaa    120
gattgggagt gttaacacat tggaatactt tataagaatt gactttaaat ttacgatgaa    180
ttgcaaatcc ttatggagct attggcaaca acatcttccg cttaggtcgc tggttgcccg    240
ctttttgatg ttagtaacgt caattatgca aatattgggg agcatcatta agaattagac    300
gacggaagaa agaaagtaca aagtcattgt gacttgtgtt tttcggttta acttgcattt    360
tacaaaccct gagtccgcca ttttcgtat tcgaagcaag gtctaaattt tgaacatata    420
tttccttgaa tattgatatt ttgaatatgg aaataaatcg tgcataagaa agttttgcta    480
tgcacgttca tacttccaaa aattcaaaga cttgatatta ttaatttagg attttactaa    540
ttcttgtcaa aagcacgggc gacgaaagag atgcatttgc tagactttca tgaatgtata    600
taaaagaggc ttcccccctc ccttgaattg aggtctgata gttttaatt tcattttatt    660 ataattgtat aaacaactac caactgctaa tattagatgc tacaacaata tacattgtta    720
ctcatatatt tgtcggttgc gactgcaaag acaatcactg gtgttttcaa cagtttaat    780 tcattgactt ggtctaatgc tgctactat cattataagg gaccaggaac cccaacttgg    840
aatgctgttt tgggttggtc tttagatggt actagtgcaa gtccgggaga tacattcaca    900
ttgaatatgc catgtgtgtt taaattact acttctcaaa catctgttga tttgactgct    960
catggtgtta aatatgctac atgtcaattt caggcaggtg aagaatttat gacctttct   1020 acattaacat gtactgtgag caatactttg actccatcta ttaaggcttt gggtactgtc   1080
accttaccac ttgcattcaa tgtaggtgga actggttctt ctgttgattt ggaagattct   1140 aaatgttta ctgctggtac taacacagtt acatttaatg atggtggcaa gaaaatctct   1200
attaatgttg attttgaaag gtcaaatgtc gatccaaaag ggtacttaac tgattccaga   1260
gttataccaa gtctcaacaa agtgtcaact cttttgttg caccacaatg tgcaaatggt   1320
tacacatctg gtacaatggg attcgctaac acttatggtg atgttcaaat tgactgttca   1380
aatattcatg ttggtattac aaaaggattg aatgattgga attatccggt tcatctgaa   1440 tcatttagtt acactaaaac ttgttcatct aatggtatct ttatcacata taaaaatgtt   1500
cctgccggtt atcgtccatt tgttgacgct tatatttctg ctacagatgt taactcgtac   1560
accttgtcgt atgctaatga atatacttgt gctggtggtt attggcaacg tgcaccttc   1620 acattaagat ggactggata cagaaatagt gatgctggat ctaacggtat tgttattgtg   1680
gctactacca gaacagttac agacagtact accgccgtga ccaccttacc attcgatcct   1740
aaccgcgaca aaactaagac aattgaaatt ttgaaaccta ttccaacaac tacaatcaca   1800
acatcatatg ttggtgtgac tacttcctac ctgaccaaaa ctgcaccaat tggggaaact   1860
gctactgtta ttgttgatat tccatatcac actaccacta ctgttaccag taaatggaca   1920
ggaacaatta cttccaccac aacacatact aatccaactg actcaataga cactgtcatt   1980
gtacaagttc cactgccaaa cccaactgtt actaccactg aatattggtc tcaatcattt   2040
gctaccacca ccaccattac tggaccacca gggaacactg tatctgtttt aatcagagaa   2100
ccaccaaacc atactgtcac tacaaccgag tattggtcag aatcttacac taccactagt   2160
actttcactg ctcctccagg tggaactgac tcggtcatca tcaaggaacc tccaaatcca   2220
actgttacaa ctaccgagta ctggtcagaa tcttacacta ccactagtac cttcactgct   2280
cctccaggtg gaactgactc ggtcatcatc aaggaaccac caaatccaac tgtcactaca   2340
acagagtact ggtcacaatc ttacactacc actactactg tcaccgctcc accaggaggt   2400
actgatactg tcttagtcag agagccacca aaccatactg ttacaactac cgagtactgg   2460
```

```
tcacaatctt acactacaac caccactgtt attgccccac caggtggtac tgacactgtt    2520
atcattagag aaccaccaaa ccacactgtc actactactg agtattggtc tcaatcttac    2580
gcaaccacta ctaccattac cgctccacct ggtgagaccg atactgtcct tattagagaa    2640
ccaccaaacc atactgtaac cacaactgag tattggtctc aatcctatgc aactactact    2700
acaatcactg ctcctccagg tgaaaccgat accgttctta ttagggaacc accaaatcac    2760
actgtcacta ctactgaata ctggtcacaa tcatatgcta ccactaccac tgtaactgca    2820
ccaccaggtg gtactgacac tgttcttatc agagagccac caaaccacac tgtcactact    2880
actgaatact ggtctcaatc atatgctaca accaccactg ttactgcacc accaggaggt    2940
accgatactg tgattattta tgacaccatg tcaagttcag aaatttcttc attttctcgt    3000
cctcattaca ccaaccatac aactttgtgg tctacaactt gggttattga acaaaaaaca    3060
attacagaaa ctagctgtga aggtgataaa ggttgttctt gggtttctgt ttctactcgt    3120
attgtcacaa ttcctaataa tatcgaaact cctatggtta ctaatactgt tgattctaca    3180
accacagaat ccacttcaca atccccatct ggtatttttt cagagtcagg agtatctgtt    3240
gaaacagaat cttctactgt tactactgct caaacaaatc caagtgttcc aacaactgaa    3300
agtgaggttg aatttactac taaaggaaac aacggaaatg gtccttatga atcaccatct    3360
actcatgtga aatcaagtat ggatgaaaat tctgaattta ctacttccac agctgcttcc    3420
acttctactg atattgaaaa tgcaaccata gcaacaaccg gttccgtgga agcttcatcg    3480
cctatcattt cttctagtgc tgatgaaact actactatta ctactactgc tgaatcaacc    3540
agtgtcattg aacaaccaac caataataat ggtggtggta agcccccatc tgcaacttca    3600
tctccatcta caactacaac tgctaataat gactctgtta ttactggtac aacatcaacc    3660
aaccaatctc aatctcaatc tcaatctaat tctgataccc aacaaactac attgagtcaa    3720
caaatgactt catctttggt tagtttacat atgcttacta catttgatgg atctggttct    3780
gttattcaac attctacttg gttatgtggt ttgatcacat tattatcctt atttatttaa    3840
ggatgatacc atcatagtcg cctttttaga tttttgttat ttgtttgttt tttgtttttt    3900
tggctccaaa aaaaaattaa tatatttttt ggttttttctt cgtgtttatt gatatttgc    3960 tattttcggt ataattaatc acctccaatt tggtgtgttg ttaatttgat tagtttgttt    4020
ctatagtttt tataattata agtatttttt attatttgaa ttttaaaaaa agagcctgcg    4080
actatgaatt gttcagtatg attcatgtag aacagaaatc tgtctactct tttatttata    4140
gaaggactga ctctggaatt tattgtaata taatctttac ttgaggttat gcatcgcttg    4200
tcagtttcag ggttttaaga ttggaaggtt tgctagataa gatacaatgc taaggaagaa    4260
tactataaag tagtaggtcc aagaaaaatg ttgctgatta taaacacttc caaaatata    4320 gtgttggcta ctaagttgag gtgttagaaa taattaagat gcaccaaagt tagaccaaac    4380
ccg                                                                 4383
```

<210> SEQ ID NO 22
<211> LENGTH: 1047
<212> TYPE: PRT
<213> ORGANISM: Candida albicans

<400> SEQUENCE: 22

```
Met Leu Gln Gln Tyr Thr Leu Leu Leu Ile Tyr Leu Ser Val Ala Thr
1               5                   10                  15

Ala Lys Thr Ile Thr Gly Val Phe Asn Ser Phe Asn Ser Leu Thr Tyr
```

```
              20                  25                  30
Ser Asn Ala Ala Thr Tyr His Tyr Lys Gly Pro Gly Thr Pro Thr Tyr
             35                  40                  45
Asn Ala Val Leu Gly Tyr Ser Leu Asp Gly Thr Ser Ala Ser Pro Gly
             50                  55                  60
Asp Thr Phe Thr Leu Asn Met Pro Cys Val Phe Lys Phe Thr Thr Ser
 65                  70                  75                  80
Gln Thr Ser Val Asp Leu Thr Ala His Gly Val Lys Tyr Ala Thr Cys
                 85                  90                  95
Gln Phe Gln Ala Gly Glu Glu Phe Met Thr Phe Ser Thr Leu Thr Cys
                100                 105                 110
Thr Val Ser Asn Thr Leu Thr Pro Ser Ile Lys Ala Leu Gly Thr Val
                115                 120                 125
Thr Leu Pro Leu Ala Phe Asn Val Gly Thr Gly Ser Ser Val Asp
                130                 135                 140
Leu Glu Asp Ser Lys Cys Phe Thr Ala Gly Thr Asn Thr Val Thr Phe
145                 150                 155                 160
Asn Asp Gly Gly Lys Lys Ile Ser Ile Asn Val Asp Phe Glu Arg Ser
                165                 170                 175
Asn Val Asp Pro Lys Gly Tyr Leu Thr Asp Ser Arg Val Ile Pro Ser
                180                 185                 190
Leu Asn Lys Val Ser Thr Leu Phe Val Ala Pro Gln Cys Ala Asn Gly
                195                 200                 205
Tyr Thr Ser Gly Thr Met Gly Phe Ala Asn Thr Tyr Gly Asp Val Gln
                210                 215                 220
Ile Asp Cys Ser Asn Ile His Val Gly Ile Thr Lys Gly Leu Asn Asp
225                 230                 235                 240
Tyr Asn Tyr Pro Val Ser Ser Glu Ser Phe Ser Tyr Thr Lys Thr Cys
                245                 250                 255
Ser Ser Asn Gly Ile Phe Ile Thr Tyr Lys Asn Val Pro Ala Gly Tyr
                260                 265                 270
Arg Pro Phe Val Asp Ala Tyr Ile Ser Ala Thr Asp Val Asn Ser Tyr
                275                 280                 285
Thr Leu Ser Tyr Ala Asn Glu Tyr Thr Cys Ala Gly Gly Tyr Tyr Gln
                290                 295                 300
Arg Ala Pro Phe Thr Leu Arg Tyr Thr Gly Tyr Arg Asn Ser Asp Ala
305                 310                 315                 320
Gly Ser Asn Gly Ile Val Ile Val Ala Thr Thr Arg Thr Val Thr Asp
                325                 330                 335
Ser Thr Thr Ala Val Thr Thr Leu Pro Phe Asp Pro Asn Arg Asp Lys
                340                 345                 350
Thr Lys Thr Ile Glu Ile Leu Lys Pro Ile Pro Thr Thr Thr Ile Thr
                355                 360                 365
Thr Ser Tyr Val Gly Val Thr Thr Ser Tyr Ser Thr Lys Thr Ala Pro
                370                 375                 380
Ile Gly Glu Thr Ala Thr Val Ile Val Asp Ile Pro Tyr His Thr Thr
385                 390                 395                 400
Thr Thr Val Thr Ser Lys Tyr Thr Gly Thr Ile Thr Ser Thr Thr Thr
                405                 410                 415
His Thr Asn Pro Thr Asp Ser Ile Asp Thr Val Ile Val Gln Val Pro
                420                 425                 430
Ser Pro Asn Pro Thr Val Thr Thr Glu Tyr Tyr Ser Gln Ser Phe
                435                 440                 445
```

```
Ala Thr Thr Thr Thr Ile Thr Gly Pro Pro Gly Asn Thr Asp Thr Val
        450                 455                 460

Leu Ile Arg Glu Pro Pro Asn His Thr Val Thr Thr Glu Tyr Tyr
465                 470                 475                 480

Ser Glu Ser Tyr Thr Thr Thr Ser Thr Phe Thr Ala Pro Pro Gly Gly
                    485                 490                 495

Thr Asp Ser Val Ile Ile Lys Glu Pro Pro Asn Pro Thr Val Thr Thr
                500                 505                 510

Thr Glu Tyr Tyr Ser Glu Ser Tyr Thr Thr Thr Ser Thr Phe Thr Ala
            515                 520                 525

Pro Pro Gly Gly Thr Asp Ser Val Ile Ile Lys Glu Pro Pro Asn Pro
        530                 535                 540

Thr Val Thr Thr Thr Glu Tyr Tyr Ser Gln Ser Tyr Thr Thr Thr Thr
545                 550                 555                 560

Thr Val Thr Ala Pro Pro Gly Gly Thr Asp Thr Val Leu Val Arg Glu
                565                 570                 575

Pro Pro Asn His Thr Val Thr Thr Thr Glu Tyr Tyr Ser Gln Ser Tyr
                580                 585                 590

Thr Thr Thr Thr Thr Val Ile Ala Pro Pro Gly Gly Thr Asp Thr Val
            595                 600                 605

Ile Ile Arg Glu Pro Pro Asn His Thr Val Thr Thr Thr Glu Tyr Tyr
        610                 615                 620

Ser Gln Ser Tyr Ala Thr Thr Thr Ile Thr Ala Pro Pro Gly Glu
625                 630                 635                 640

Thr Asp Thr Val Leu Ile Arg Glu Pro Pro Asn His Thr Val Thr Thr
                645                 650                 655

Thr Glu Tyr Tyr Ser Gln Ser Tyr Ala Thr Thr Thr Ile Thr Ala
            660                 665                 670

Pro Pro Gly Glu Thr Asp Thr Val Leu Ile Arg Glu Pro Pro Asn His
        675                 680                 685

Thr Val Thr Thr Thr Glu Tyr Tyr Ser Gln Ser Tyr Ala Thr Thr Thr
690                 695                 700

Thr Val Thr Ala Pro Pro Gly Gly Thr Asp Thr Val Leu Ile Arg Glu
705                 710                 715                 720

Pro Pro Asn His Thr Val Thr Thr Thr Glu Tyr Tyr Ser Gln Ser Tyr
                725                 730                 735

Ala Thr Thr Thr Thr Val Thr Ala Pro Pro Gly Gly Thr Asp Thr Val
            740                 745                 750

Ile Ile Tyr Asp Thr Met Ser Ser Glu Ile Ser Ser Phe Ser Arg
        755                 760                 765

Pro His Tyr Thr Asn His Thr Thr Leu Tyr Ser Thr Thr Tyr Val Ile
770                 775                 780

Glu Thr Lys Thr Ile Thr Glu Thr Ser Cys Glu Gly Asp Lys Gly Cys
785                 790                 795                 800

Ser Tyr Val Ser Val Ser Thr Arg Ile Val Thr Ile Pro Asn Asn Ile
                805                 810                 815

Glu Thr Pro Met Val Thr Asn Thr Val Asp Ser Thr Thr Thr Glu Ser
                820                 825                 830

Thr Ser Gln Ser Pro Ser Gly Ile Phe Ser Glu Ser Gly Val Ser Val
            835                 840                 845

Glu Thr Glu Ser Ser Thr Val Thr Thr Ala Gln Thr Asn Pro Ser Val
            850                 855                 860
```

Pro Thr Thr Glu Ser Glu Val Glu Phe Thr Thr Lys Gly Asn Asn Gly
865                 870                 875                 880

Asn Gly Pro Tyr Glu Ser Pro Ser Thr His Val Lys Ser Ser Met Asp
            885                 890                 895

Glu Asn Ser Glu Phe Thr Thr Ser Thr Ala Ala Ser Thr Ser Thr Asp
                900                 905                 910

Ile Glu Asn Ala Thr Ile Ala Thr Thr Gly Ser Val Glu Ala Ser Ser
            915                 920                 925

Pro Ile Ile Ser Ser Ser Ala Asp Glu Thr Thr Thr Ile Thr Thr Thr
        930                 935                 940

Ala Glu Ser Thr Ser Val Ile Glu Gln Pro Thr Asn Asn Asn Gly Gly
945                 950                 955                 960

Gly Lys Ala Pro Ser Ala Thr Ser Ser Pro Ser Thr Thr Thr Thr Ala
                965                 970                 975

Asn Asn Asp Ser Val Ile Thr Gly Thr Thr Ser Thr Asn Gln Ser Gln
            980                 985                 990

Ser Gln Ser Gln Ser Asn Ser Asp Thr Gln Gln Thr Thr Leu Ser Gln
        995                 1000                1005

Gln Met Thr Ser Ser Leu Val Ser Leu His Met Leu Thr Thr Phe
    1010                1015                1020

Asp Gly Ser Gly Ser Val Ile Gln His Ser Thr Tyr Leu Cys Gly
    1025                1030                1035

Leu Ile Thr Leu Leu Ser Leu Phe Ile
    1040                1045

<210> SEQ ID NO 23
<211> LENGTH: 1404
<212> TYPE: DNA
<213> ORGANISM: Candida albicans

<400> SEQUENCE: 23
atgcttccac aattcatatt gttattcata tctttgacag tgtcgactgc aaaaactatt      60
actggtgttt tcaatagttt tgactcattg acatggacta gatccgttga atatgcttac     120
aaagggccag agactccaac ttggaatgca gttttagggt ggtccttaaa tagtaccact     180
gctgacccag agacacatt caccttgatt ttgccttgtg tatttaaatt tataactacc     240
caaacatctg ttgatttgac tgctgatggt gttagctatg ccacttgtga ctttaatgct     300
ggtgaagaat ttacgacatt tcttccctta tcatgtactg tgaacagtgt tcggtatca      360
tatgctaggg tttctggtac ggtcaaattg cccattacat tcaatgtagg tggaacaggt     420
tcttcagttg atttggcaga ttccaaatgt tttactgccg aaaaaacac tgtgactttc      480
atggatggcg atacaaagat ttctaccact gttgattttg acgcgtctcc agtatcaccc     540
agtggttata ttacaagctc acgaattatt cctagtctca ataactttc aagtcttttc      600
gtggtgccac aatgtgagaa tggttacaca tctggtataa tgggatttgt agctagtaac     660
ggtgctacta ttgattgctc aaatgtcaat ataggaatat caaaaggttt aaatgattgg     720
aattttccag taagttcaga atcattttct tacacgaaaa cttgtacgtc aaccagtatt     780
acagttgaat ttcaaaatgt tcctgctggg atcgcccctt ttgttgatgc atatatttct     840
gcagaaaata ttgataaata taccttgacg tacgcaaatg agtatacttg tgaaaatggc     900
aatactgtgg ttgatccatt tacttttaac tggtgggggt ataaaaactc tgaagcagac     960
tctgacgggg atgtgatcgt agttacaacc agaactgtca cagacagtac aacagctgtg    1020
actactttac ctttcaatcc aagtgtcgat aaaaccgaaa caattgaaat tttgcaaccc    1080

```
attcccacga ccacaattac aacttcatat attggtattt ccacttccta tgaaacatta    1140
accggaacaa ttggtggtac tgcgacagtc attgtcgata caccttatca tatcactgcc    1200
actgttacaa atttctggac tgggtcaatt acaactacca ctacttatac taatcccact    1260
ggttccatag acactgttat tgtgcaaatt ccactgcctg atccaactac aactataact    1320
gaattttggt ctgaatcatt tgctagtact accaccatca ccaacccacc tgacggtact    1380
aatagtgtga tcatcaaaga acca                                          1404
```

<210> SEQ ID NO 24
<211> LENGTH: 468
<212> TYPE: PRT
<213> ORGANISM: Candida albicans

<400> SEQUENCE: 24

```
Met Leu Pro Gln Phe Ile Leu Phe Ile Ser Leu Thr Val Ser Thr
1               5                   10                  15

Ala Lys Thr Ile Thr Gly Val Phe Asn Ser Phe Asp Ser Leu Thr Tyr
            20                  25                  30

Thr Arg Ser Val Glu Tyr Ala Tyr Lys Gly Pro Glu Thr Pro Thr Tyr
        35                  40                  45

Asn Ala Val Leu Gly Tyr Ser Leu Asn Ser Thr Thr Ala Asp Pro Gly
    50                  55                  60

Asp Thr Phe Thr Leu Ile Leu Pro Cys Val Phe Lys Phe Ile Thr Thr
65                  70                  75                  80

Gln Thr Ser Val Asp Leu Thr Ala Asp Gly Val Ser Tyr Ala Thr Cys
                85                  90                  95

Asp Phe Asn Ala Gly Glu Glu Phe Thr Thr Phe Ser Ser Leu Ser Cys
            100                 105                 110

Thr Val Asn Ser Val Ser Val Ser Tyr Ala Arg Val Ser Gly Thr Val
        115                 120                 125

Lys Leu Pro Ile Thr Phe Asn Val Gly Gly Thr Gly Ser Ser Val Asp
    130                 135                 140

Leu Ala Asp Ser Lys Cys Phe Thr Ala Gly Lys Asn Thr Val Thr Phe
145                 150                 155                 160

Met Asp Gly Asp Thr Lys Ile Ser Thr Thr Val Asp Phe Asp Ala Ser
                165                 170                 175

Pro Val Ser Pro Ser Gly Tyr Ile Thr Ser Ser Arg Ile Ile Pro Ser
            180                 185                 190

Leu Asn Lys Leu Ser Ser Leu Phe Val Val Pro Gln Cys Glu Asn Gly
        195                 200                 205

Tyr Thr Ser Gly Ile Met Gly Phe Val Ala Ser Asn Gly Ala Thr Ile
    210                 215                 220

Asp Cys Ser Asn Val Asn Ile Gly Ile Ser Lys Gly Leu Asn Asp Tyr
225                 230                 235                 240

Asn Phe Pro Val Ser Ser Glu Ser Phe Ser Tyr Thr Lys Thr Cys Thr
                245                 250                 255

Ser Thr Ser Ile Thr Val Glu Phe Gln Asn Val Pro Ala Gly Tyr Arg
            260                 265                 270

Pro Phe Val Asp Ala Tyr Ile Ser Ala Glu Asn Ile Asp Lys Tyr Thr
        275                 280                 285

Leu Thr Tyr Ala Asn Glu Tyr Thr Cys Glu Asn Gly Asn Thr Val Val
    290                 295                 300

Asp Pro Phe Thr Leu Thr Tyr Tyr Gly Tyr Lys Asn Ser Glu Ala Asp
```

```
305                 310                 315                 320
Ser Asp Gly Asp Val Ile Val Thr Thr Arg Thr Val Thr Asp Ser
                325                 330                 335

Thr Thr Ala Val Thr Thr Leu Pro Phe Asn Pro Ser Val Asp Lys Thr
            340                 345                 350

Glu Thr Ile Glu Ile Leu Gln Pro Ile Pro Thr Thr Thr Ile Thr Thr
                355                 360                 365

Ser Tyr Ile Gly Ile Ser Thr Ser Tyr Glu Thr Leu Thr Gly Thr Ile
        370                 375                 380

Gly Gly Thr Ala Thr Val Ile Val Asp Thr Pro Tyr His Ile Thr Ala
385                 390                 395                 400

Thr Val Thr Asn Phe Tyr Thr Gly Ser Ile Thr Thr Thr Thr Thr Tyr
                405                 410                 415

Thr Asn Pro Thr Gly Ser Ile Asp Thr Val Ile Val Gln Ile Pro Ser
            420                 425                 430

Pro Asp Pro Thr Thr Thr Ile Thr Glu Phe Tyr Ser Glu Ser Phe Ala
                435                 440                 445

Ser Thr Thr Thr Ile Thr Asn Pro Pro Asp Gly Thr Asn Ser Val Ile
        450                 455                 460

Ile Lys Glu Pro
465

<210> SEQ ID NO 25
<211> LENGTH: 534
<212> TYPE: PRT
<213> ORGANISM: Candida albicans

<400> SEQUENCE: 25

Met Leu Gln Gln Phe Thr Leu Leu Phe Leu Tyr Leu Ser Ile Ala Ser
1               5                   10                  15

Ala Lys Thr Ile Thr Gly Val Phe Asp Ser Phe Asn Ser Leu Thr Trp
            20                  25                  30

Ser Asn Ala Ala Asn Tyr Ala Phe Lys Gly Pro Gly Tyr Pro Thr Trp
        35                  40                  45

Asn Ala Val Leu Gly Trp Ser Leu Asp Gly Thr Ser Ala Asn Pro Gly
    50                  55                  60

Asp Thr Phe Thr Leu Asn Met Pro Cys Val Phe Lys Tyr Thr Thr Ser
65                  70                  75                  80

Gln Thr Ser Val Asp Leu Thr Ala Asp Gly Val Lys Tyr Ala Thr Cys
                85                  90                  95

Gln Phe Tyr Ser Gly Glu Glu Phe Thr Thr Phe Ser Thr Leu Thr Cys
            100                 105                 110

Thr Val Asn Asp Ala Leu Lys Ser Ser Ile Lys Ala Phe Gly Thr Val
        115                 120                 125

Thr Leu Pro Ile Ala Phe Asn Val Gly Gly Thr Gly Ser Ser Thr Asp
130                 135                 140

Leu Glu Asp Ser Lys Cys Phe Thr Ala Gly Thr Asn Thr Val Thr Phe
145                 150                 155                 160

Asn Asp Gly Asp Lys Asp Ile Ser Ile Asp Val Glu Phe Glu Lys Ser
                165                 170                 175

Thr Val Asp Pro Ser Ala Tyr Leu Tyr Ala Ser Arg Val Met Pro Ser
            180                 185                 190

Leu Asn Lys Val Thr Thr Leu Phe Val Ala Pro Gln Cys Glu Asn Gly
        195                 200                 205
```

-continued

```
Tyr Thr Ser Gly Thr Met Gly Phe Ser Ser Asn Gly Asp Val Ala
    210                 215                 220

Ile Asp Cys Ser Asn Ile His Ile Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Thr Ser Asn Gly Ile Gln Ile Lys Tyr Gln Asn Val Pro Ala Gly Tyr
            260                 265                 270

Arg Pro Phe Ile Asp Ala Tyr Ile Ser Ala Thr Asp Val Asn Gln Tyr
        275                 280                 285

Thr Leu Ala Tyr Thr Asn Asp Tyr Thr Cys Ala Gly Ser Arg Leu Gln
    290                 295                 300

Ser Lys Pro Phe Thr Leu Arg Trp Thr Gly Tyr Lys Asn Ser Asp Ala
305                 310                 315                 320

Gly Ser Asn Gly Ile Val Ile Ala Thr Thr Arg Thr Val Thr Asp
                325                 330                 335

Ser Thr Thr Ala Val Thr Thr Leu Pro Phe Asn Pro Ser Val Asp Lys
                340                 345                 350

Thr Lys Thr Ile Glu Ile Leu Gln Pro Ile Pro Thr Thr Thr Ile Thr
            355                 360                 365

Thr Ser Tyr Val Gly Val Thr Thr Ser Tyr Leu Thr Lys Thr Ala Pro
    370                 375                 380

Ile Gly Glu Thr Ala Thr Val Ile Val Asp Val Pro Tyr His Thr Thr
385                 390                 395                 400

Thr Thr Val Thr Ser Glu Trp Thr Gly Thr Ile Thr Thr Thr Thr Thr
                405                 410                 415

Arg Thr Asn Pro Thr Asp Ser Ile Asp Thr Val Val Gln Val Pro
            420                 425                 430

Leu Pro Asn Pro Thr Val Ser Thr Thr Glu Tyr Trp Ser Gln Ser Phe
    435                 440                 445

Ala Thr Thr Thr Thr Val Thr Ala Pro Pro Gly Gly Thr Asp Thr Val
    450                 455                 460

Ile Ile Arg Glu Pro Pro Asn His Thr Val Thr Thr Thr Glu Tyr Trp
465                 470                 475                 480

Ser Gln Ser Phe Ala Thr Thr Thr Val Thr Ala Pro Pro Gly Gly
                485                 490                 495

Thr Asp Ser Val Ile Ile Arg Glu Pro Pro Asn Pro Thr Val Thr Thr
                500                 505                 510

Thr Glu Tyr Trp Ser Gln Ser Phe Ala Thr Thr Thr Thr Val Thr Ala
            515                 520                 525

Pro Pro Gly Gly Thr Asp
    530
```

<210> SEQ ID NO 26
<211> LENGTH: 534
<212> TYPE: PRT
<213> ORGANISM: Candida albicans

<400> SEQUENCE: 26

```
Met Leu Gln Gln Tyr Thr Leu Leu Leu Ile Tyr Leu Ser Val Ala Thr
1               5                   10                  15

Ala Lys Thr Ile Thr Gly Val Phe Asn Ser Phe Asn Ser Leu Thr Trp
            20                  25                  30

Ser Asn Ala Ala Thr Tyr Asn Tyr Lys Gly Pro Gly Thr Pro Thr Trp
        35                  40                  45
```

-continued

```
Asn Ala Val Leu Gly Trp Ser Leu Asp Gly Thr Ser Ala Ser Pro Gly
         50                  55                  60

Asp Thr Phe Thr Leu Asn Met Pro Cys Val Phe Lys Phe Thr Thr Ser
 65                  70                  75                  80

Gln Thr Ser Val Asp Leu Thr Ala His Gly Val Lys Tyr Ala Thr Cys
                 85                  90                  95

Gln Phe Gln Ala Gly Glu Glu Phe Met Thr Phe Ser Thr Leu Thr Cys
                100                 105                 110

Thr Val Ser Asn Thr Leu Thr Pro Ser Ile Lys Ala Leu Gly Thr Val
             115                 120                 125

Thr Leu Pro Leu Ala Phe Asn Val Gly Thr Gly Ser Ser Val Asp
         130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                 165                 170                 175

Asn Val Asp Pro Lys Gly Tyr Leu Thr Asp Ser Arg Val Ile Pro Ser
             180                 185                 190

Leu Asn Lys Val Ser Thr Leu Phe Val Ala Pro Gln Cys Ala Asn Gly
         195                 200                 205

Tyr Thr Ser Gly Thr Met Gly Phe Ala Asn Thr Tyr Gly Asp Val Gln
    210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
                 245                 250                 255

Ser Ser Asn Gly Ile Phe Ile Thr Tyr Lys Asn Val Pro Ala Gly Tyr
             260                 265                 270

Arg Pro Phe Val Asp Ala Tyr Ile Ser Ala Thr Asp Val Asn Ser Tyr
         275                 280                 285

Thr Leu Ser Tyr Ala Asn Glu Tyr Thr Cys Ala Gly Gly Tyr Trp Gln
    290                 295                 300

Arg Ala Pro Phe Thr Leu Arg Trp Thr Gly Tyr Arg Asn Ser Asp Ala
305                 310                 315                 320

Gly Ser Asn Gly Ile Val Ile Ala Thr Thr Arg Thr Val Thr Asp
                 325                 330                 335

Ser Thr Thr Ala Val Thr Thr Leu Pro Phe Asp Pro Asn Arg Asp Lys
             340                 345                 350

Thr Lys Thr Ile Glu Ile Leu Lys Pro Ile Pro Thr Thr Thr Ile Thr
         355                 360                 365

Thr Ser Tyr Val Gly Val Thr Thr Ser Tyr Leu Thr Lys Thr Ala Pro
    370                 375                 380

Ile Gly Glu Thr Ala Thr Val Ile Val Asp Ile Pro Tyr His Thr Thr
385                 390                 395                 400

Thr Thr Val Thr Ser Lys Trp Thr Gly Thr Ile Thr Ser Thr Thr Thr
                 405                 410                 415

His Thr Asn Pro Thr Asp Ser Ile Asp Thr Val Ile Val Gln Val Pro
             420                 425                 430

Leu Pro Asn Pro Thr Val Thr Thr Glu Tyr Trp Ser Gln Ser Phe
         435                 440                 445

Ala Thr Thr Thr Ile Thr Gly Pro Pro Gly Asn Thr Asp Thr Val
    450                 455                 460
```

```
Leu Ile Arg Glu Pro Pro Asn His Thr Val Thr Thr Glu Tyr Trp
465                 470                 475                 480

Ser Glu Ser Tyr Thr Thr Thr Ser Thr Phe Thr Ala Pro Pro Gly Gly
                485                 490                 495

Thr Asp Ser Val Ile Ile Lys Glu Pro Pro Asn Pro Thr Val Thr Thr
            500                 505                 510

Thr Glu Tyr Trp Ser Glu Ser Tyr Thr Thr Ser Thr Phe Thr Ala
            515                 520                 525

Pro Pro Gly Gly Thr Asp
    530

<210> SEQ ID NO 27
<211> LENGTH: 534
<212> TYPE: PRT
<213> ORGANISM: Candida albicans

<400> SEQUENCE: 27

Met Ile Gln Gln Phe Thr Leu Leu Phe Leu Tyr Leu Ser Phe Ala Thr
1               5                   10                  15

Ala Lys Ala Ile Thr Gly Ile Phe Asn Ser Ile Asp Ser Leu Thr Trp
            20                  25                  30

Ser Asn Ala Gly Asn Tyr Ala Phe Lys Gly Pro Gly Tyr Pro Thr Trp
        35                  40                  45

Asn Ala Val Leu Gly Trp Ser Leu Asp Gly Thr Ser Ala Asn Pro Gly
    50                  55                  60

Asp Thr Phe Ile Leu Asn Met Pro Cys Val Phe Lys Phe Thr Ala Ser
65                  70                  75                  80

Gln Lys Ser Val Asp Leu Thr Ala Asp Gly Val Lys Tyr Ala Thr Cys
                85                  90                  95

Gln Phe Tyr Ser Gly Glu Glu Phe Thr Thr Phe Ser Ser Leu Lys Cys
            100                 105                 110

Thr Val Asn Asn Asn Leu Arg Ser Ser Ile Lys Ala Leu Gly Thr Val
        115                 120                 125

Thr Leu Pro Ile Ala Phe Asn Val Gly Gly Thr Gly Ser Ser Val Asp
130                 135                 140

Leu Glu Asp Ser Lys Cys Phe Thr Ala Gly Thr Asn Thr Val Thr Phe
145                 150                 155                 160

Asn Asp Gly Ser Lys Lys Leu Ser Ile Ala Val Asn Phe Glu Lys Ser
                165                 170                 175

Thr Val Asp Gln Ser Gly Tyr Leu Thr Thr Ser Arg Phe Met Pro Ser
            180                 185                 190

Leu Asn Lys Ile Ala Thr Leu Tyr Val Ala Pro Gln Cys Glu Asn Gly
        195                 200                 205

Tyr Thr Ser Gly Thr Met Gly Phe Ser Thr Ser Tyr Gly Asp Val Ala
    210                 215                 220

Ile Asp Cys Ser Asn Val His Ile Gly Ile Ser Lys Gly Val Asn Asp
225                 230                 235                 240

Trp Asn His Pro Val Thr Ser Glu Ser Phe Ser Tyr Thr Lys Ser Cys
                245                 250                 255

Ser Ser Phe Gly Ile Ser Ile Thr Tyr Gln Asn Val Pro Ala Gly Tyr
            260                 265                 270

Arg Pro Phe Ile Asp Ala Tyr Ile Ser Pro Ser Asp Asn Asn Gln Tyr
        275                 280                 285

Gln Leu Ser Tyr Lys Asn Asp Tyr Thr Cys Val Asp Asp Tyr Trp Gln
    290                 295                 300
```

His Ala Pro Phe Thr Leu Lys Trp Thr Gly Tyr Lys Asn Ser Asp Ala
305                 310                 315                 320

Gly Ser Asn Gly Ile Val Ile Val Ala Thr Thr Arg Thr Val Thr Asp
            325                 330                 335

Ser Thr Thr Ala Val Thr Thr Leu Pro Phe Asn Pro Ser Val Asp Lys
        340                 345                 350

Thr Lys Thr Ile Glu Ile Leu Gln Pro Ile Pro Thr Thr Ile Thr
    355                 360                 365

Thr Ser Tyr Val Gly Val Thr Thr Ser Tyr Leu Thr Lys Thr Ala Pro
    370                 375                 380

Ile Gly Glu Thr Ala Thr Val Ile Val Asp Val Pro Tyr His Thr Thr
385                 390                 395                 400

Thr Thr Val Thr Ser Glu Trp Thr Gly Thr Ile Thr Thr Thr Thr
            405                 410                 415

Arg Thr Asn Pro Thr Asp Ser Ile Asp Thr Val Val Gln Val Pro
            420                 425                 430

Leu Pro Asn Pro Thr Thr Thr Thr Gln Phe Trp Ser Glu Ser Phe
        435                 440                 445

Thr Ser Thr Thr Thr Ile Thr Asn Ser Leu Lys Gly Thr Asp Ser Val
    450                 455                 460

Ile Val Arg Glu Pro His Asn Pro Thr Val Thr Thr Glu Phe Trp
465                 470                 475                 480

Ser Glu Ser Phe Ala Thr Thr Glu Thr Ile Thr Ser Lys Pro Glu Gly
            485                 490                 495

Thr Asp Ser Val Ile Val Arg Glu Pro His Asn Pro Thr Val Thr Thr
        500                 505                 510

Thr Glu Phe Trp Ser Glu Ser Tyr Ala Thr Glu Thr Ile Thr Asn
        515                 520                 525

Gly Pro Glu Gly Thr Asp
    530

<210> SEQ ID NO 28
<211> LENGTH: 537
<212> TYPE: PRT
<213> ORGANISM: Candida albicans

<400> SEQUENCE: 28

Met Lys Thr Val Ile Leu Leu His Leu Phe Phe Tyr Cys Thr Ile Ala
1               5                   10                  15

Met Ala Lys Thr Ile Ser Gly Val Phe Thr Ser Phe Asn Ser Leu Thr
            20                  25                  30

Tyr Thr Asn Thr Gly Asn Tyr Pro Tyr Gly Pro Gly Tyr Pro Thr
        35                  40                  45

Trp Thr Ala Val Leu Gly Trp Ser Leu Asp Gly Thr Leu Ala Ser Pro
50                  55                  60

Gly Asp Thr Phe Thr Leu Val Met Pro Cys Val Phe Lys Phe Ile Thr
65                  70                  75                  80

Thr Gln Thr Ser Val Asp Leu Thr Ala Asn Gly Val Lys Tyr Ala Thr
            85                  90                  95

Cys Thr Phe His Ala Gly Glu Asp Phe Thr Thr Phe Ser Ser Met Ser
            100                 105                 110

Cys Val Val Asn Asn Gly Leu Ser Ser Asn Ile Arg Ala Phe Gly Thr
        115                 120                 125

Val Arg Leu Pro Ile Ser Phe Asn Val Gly Gly Thr Gly Ser Ser Val

```
              130                 135                 140
    Asn Ile Gln Asp Ser Lys Cys Phe Thr Ala Gly Thr Asn Thr Val Thr
    145                 150                 155                 160

Phe Thr Asp Gly Asp His Lys Ile Ser Thr Thr Val Asn Phe Pro Lys
                    165                 170                 175

Thr Pro Gln Ser Ser Ser Ser Leu Val Tyr Phe Ala Arg Val Ile Pro
                180                 185                 190

Ser Leu Asp Lys Leu Ser Ser Leu Val Ala Ser Gln Cys Thr Ala
                195                 200                 205

Gly Tyr Ala Ser Gly Val Leu Gly Phe Ser Ala Thr Lys Asp Asp Val
            210                 215                 220

Thr Ile Asp Cys Ser Thr Ile His Val Gly Ile Thr Asn Gly Leu Asn
    225                 230                 235                 240

Ser Trp Asn Met Pro Val Ser Ser Glu Ser Phe Ser Tyr Thr Lys Thr
                    245                 250                 255

Cys Thr Pro Asn Ser Phe Ile Ile Thr Tyr Glu Asn Val Pro Ala Gly
                    260                 265                 270

Tyr Arg Pro Phe Ile Asp Ser Tyr Val Lys Lys Ser Ala Thr Ala Thr
                275                 280                 285

Asn Gly Phe Asn Leu Asn Tyr Thr Asn Ile Tyr Asn Cys Met Asp Gly
                290                 295                 300

Lys Lys Gly Asn Asp Pro Leu Ile Tyr Phe Trp Thr Ser Tyr Thr Asn
    305                 310                 315                 320

Ser Asp Ala Gly Ser Asn Gly Ala Ala Val Val Thr Thr Arg Thr
                    325                 330                 335

Val Thr Asp Ser Thr Thr Ala Ile Thr Thr Leu Pro Phe Asp Pro Thr
                    340                 345                 350

Val Asp Lys Thr Lys Thr Ile Glu Val Ile Glu Pro Ile Pro Thr Thr
                355                 360                 365

Thr Ile Thr Thr Ser Tyr Val Gly Ile Ser Thr Ser Leu Ser Thr Lys
                370                 375                 380

Thr Ala Thr Ile Gly Gly Thr Ala Thr Val Val Asp Val Pro Tyr
    385                 390                 395                 400

His Thr Thr Thr Thr Ile Thr Ser Ile Trp Thr Gly Ser Ala Thr Thr
                    405                 410                 415

Ser Ser Thr Tyr Thr Asn Pro Thr Asp Ser Ile Asp Thr Val Val Val
                420                 425                 430

Gln Val Pro Ser Pro Asn Pro Thr Val Thr Thr Gln Phe Trp Ser
                435                 440                 445

Gly Ser Val Pro Thr Thr Glu Thr Val Thr Gly Pro Gln Gly Thr
    450                 455                 460

Asp Ser Val Ile Ile Lys Glu Pro His Asn Pro Thr Val Thr Thr
    465                 470                 475                 480

Glu Phe Trp Ser Glu Ser Phe Ala Thr Glu Thr Val Thr Asn Gly
                    485                 490                 495

Pro Glu Gly Thr Asp Ser Val Ile Val Arg Glu Pro His Asn Pro Thr
                    500                 505                 510

Val Thr Thr Thr Glu Phe Trp Ser Glu Ser Phe Ala Thr Thr Glu Thr
                515                 520                 525

Val Thr Asn Gly Pro Glu Gly Thr Asp
                530                 535

<210> SEQ ID NO 29
```

```
<211> LENGTH: 536
<212> TYPE: PRT
<213> ORGANISM: Candida albicans

<400> SEQUENCE: 29

Met Lys Lys Leu Tyr Leu Leu Tyr Leu Leu Ala Ser Phe Thr Thr Val
1               5                   10                  15

Ile Ser Lys Glu Val Thr Gly Val Phe Asn Gln Phe Asn Ser Leu Ile
            20                  25                  30

Trp Ser Tyr Thr Tyr Arg Ala Arg Tyr Glu Glu Ile Ser Thr Leu Thr
        35                  40                  45

Ala Lys Ala Gln Leu Glu Trp Ala Leu Asp Gly Thr Ile Ala Ser Pro
    50                  55                  60

Gly Asp Thr Phe Thr Leu Val Met Pro Cys Val Tyr Lys Phe Met Thr
65                  70                  75                  80

Tyr Glu Thr Ser Val Gln Leu Thr Ala Asn Ser Ile Ala Tyr Ala Thr
                85                  90                  95

Cys Asp Phe Asp Ala Gly Glu Asp Thr Lys Ser Phe Ser Ser Leu Lys
            100                 105                 110

Cys Thr Val Thr Asp Glu Leu Thr Glu Asp Thr Ser Val Phe Gly Ser
        115                 120                 125

Val Ile Leu Pro Ile Ala Phe Asn Val Gly Gly Ser Gly Ser Lys Ser
    130                 135                 140

Thr Ile Thr Asp Ser Lys Cys Phe Ser Ser Gly Tyr Asn Thr Val Thr
145                 150                 155                 160

Phe Phe Asp Gly Asn Asn Gln Leu Ser Thr Thr Ala Asn Phe Leu Pro
                165                 170                 175

Arg Arg Glu Leu Ala Phe Gly Leu Val Val Ser Gln Arg Leu Ser Met
            180                 185                 190

Ser Leu Asp Thr Met Thr Asn Phe Val Met Ser Thr Pro Cys Phe Met
        195                 200                 205

Gly Tyr Gln Ser Gly Lys Leu Gly Phe Thr Ser Asn Asp Asp Phe
    210                 215                 220

Glu Ile Asp Cys Ser Ser Ile His Val Gly Ile Thr Asn Glu Ile Asn
225                 230                 235                 240

Asp Trp Ser Met Pro Val Ser Ser Val Pro Phe Asp His Thr Ile Arg
                245                 250                 255

Cys Thr Ser Arg Ala Leu Tyr Ile Glu Phe Lys Thr Ile Pro Ala Gly
            260                 265                 270

Tyr Arg Pro Phe Val Asp Ala Ile Val Gln Ile Pro Thr Thr Glu Pro
        275                 280                 285

Phe Phe Val Lys Tyr Thr Asn Glu Phe Ala Cys Val Asn Gly Ile Tyr
    290                 295                 300

Thr Ser Ile Pro Phe Thr Ser Phe Ser Gln Pro Ile Leu Tyr Asp
305                 310                 315                 320

Glu Ala Leu Ala Ile Gly Ala Asp Leu Val Arg Thr Thr Ser Thr Val
                325                 330                 335

Ile Gly Ser Ile Thr Arg Thr Thr Thr Leu Pro Phe Ile Ser Arg Leu
            340                 345                 350

Gln Lys Thr Lys Thr Ile Leu Val Leu Glu Pro Ile Pro Thr Thr Thr
        355                 360                 365

Val Thr Thr Ser His His Gly Phe Asp Thr Trp Tyr Tyr Thr Lys Lys
    370                 375                 380

Ala Thr Ile Gly Asp Thr Ala Thr Val Phe Ile Asp Val Pro Gln His
```

```
              385                 390                 395                 400
Thr Ala Thr Thr Leu Thr Thr Tyr Trp Gln Glu Ser Ser Thr Ala Thr
                405                 410                 415

Thr Thr Tyr Phe Asp Asp Ile Asp Leu Val Asp Thr Val Ile Val Lys
                420                 425                 430

Ile Pro Tyr Pro Asn Pro Thr Val Thr Thr Lys Phe Trp Ser Glu
                435                 440                 445

Ser Phe Ala Thr Thr Glu Thr Val Thr Asn Gly Pro Glu Gly Thr Asp
            450                 455                 460

Ser Val Ile Ile Lys Glu Pro His Asn Pro Thr Val Thr Thr Thr Lys
465                 470                 475                 480

Phe Trp Ser Glu Ser Phe Ala Thr Thr Glu Thr Val Thr Asn Gly Pro
                485                 490                 495

Glu Gly Thr Asp Ser Val Ile Ile Lys Glu Pro His Asn Pro Thr Val
                500                 505                 510

Thr Thr Thr Lys Phe Trp Ser Glu Ser Phe Ala Thr Thr Glu Thr Val
                515                 520                 525

Thr Asn Gly Pro Glu Gly Thr Asp
530                 535

<210> SEQ ID NO 30
<211> LENGTH: 532
<212> TYPE: PRT
<213> ORGANISM: Candida albicans

<400> SEQUENCE: 30

Met Leu Pro Gln Phe Leu Leu Leu Leu Tyr Leu Thr Val Ser Thr
1               5                   10                  15

Ala Lys Thr Ile Thr Gly Val Phe Asn Ser Phe Asn Ser Leu Thr Trp
                20                  25                  30

Ala Asn Ala Ala Asn Tyr Gly Tyr Gln Thr Pro Glu Thr Pro Thr Trp
                35                  40                  45

Thr Ala Val Leu Gly Trp Ser Leu Asn Ser Thr Thr Ala Asp Ala Gly
            50                  55                  60

Asp Thr Phe Thr Leu Ile Met Pro Cys Val Phe Lys Phe Ile Thr Ser
65                  70                  75                  80

Gln Thr Ser Val Asp Leu Thr Ala Asp Gly Val Ser Tyr Ala Thr Cys
                85                  90                  95

Asp Phe Asn Ala Gly Glu Glu Phe Thr Thr Phe Ser Ser Leu Ser Cys
                100                 105                 110

Thr Val Asn Ser Val Ser Val Ser Tyr Asp Lys Ala Ser Gly Thr Val
                115                 120                 125

Lys Leu Pro Phe Ser Phe Asn Val Gly Gly Thr Gly Ser Ser Val Asp
130                 135                 140

Leu Thr Asp Ser Lys Cys Phe Thr Ala Gly Lys Asn Thr Val Thr Phe
145                 150                 155                 160

Thr Asp Gly Asp Thr Glu Ile Ser Thr Ser Val Asp Phe Gln Ala Ser
                165                 170                 175

Pro Ile Ser Ser Ser Gly Tyr Ile Ala Ser Ala Arg Val Val Pro Ser
                180                 185                 190

Leu Asn Lys Ala Ser Ser Leu Phe Val Leu Pro Gln Cys Glu Asn Gly
                195                 200                 205

Tyr Thr Ser Gly Ile Met Gly Phe Val Thr Ser Gln Gly Ala Thr Ile
            210                 215                 220
```

Asp Cys Ser Asn Ile Asn Ile Gly Ile Ser Lys Gly Leu Asn Asp Trp
225                 230                 235                 240

Asn Phe Pro Val Ser Ser Glu Ser Phe Thr Tyr Thr Lys Thr Cys Ser
            245                 250                 255

Ser Ser Gly Ile Ile Val Glu Tyr Glu Asn Val Pro Ala Gly Tyr Arg
        260                 265                 270

Pro Phe Val Asp Ala Tyr Ile Ser Ser Glu Asn Val Glu Gln Tyr Thr
            275                 280                 285

Leu Thr Tyr Ala Asn Glu Tyr Thr Cys Lys Asn Gly Asn Thr Val Val
        290                 295                 300

Asp Pro Phe Thr Leu Thr Trp Ile Gly Tyr Lys Asn Ser Glu Ala Asp
305                 310                 315                 320

Ser Asn Gly Asp Ile Ile Val Val Thr Thr Lys Thr Val Thr Ala Ser
            325                 330                 335

Thr Thr Ala Val Thr Thr Leu Pro Phe Asn Pro Thr Val Asp Lys Thr
            340                 345                 350

Glu Thr Ile Glu Val Leu Gln Pro Ile Pro Thr Thr Thr Ile Thr Thr
        355                 360                 365

Ser Tyr Val Gly Val Thr Thr Ser Tyr Glu Thr Phe Thr Ala Thr Ile
370                 375                 380

Gly Gly Thr Ala Thr Val Ile Val Asp Thr Pro Tyr His Ile Thr Thr
385                 390                 395                 400

Thr Val Thr Thr Phe Trp Ile Gly Ser Val Thr Thr Thr Thr Thr Tyr
            405                 410                 415

Ser Asn Pro Thr Gly Ser Val Asp Thr Val Ile Val Glu Leu Pro Leu
            420                 425                 430

Pro Ala Pro Thr Val Thr His Glu Phe Trp Ser Glu Ser Phe Ala Ser
            435                 440                 445

Thr Thr Thr Val Thr Asn Pro Pro Asp Gly Thr Asn Ser Val Ile Ile
        450                 455                 460

Lys Glu Pro Tyr Asn Pro Thr Val Thr Thr Glu Phe Trp Ser Glu
465                 470                 475                 480

Ser Phe Ala Ser Thr Thr Thr Val Thr Asn Pro Pro Asp Gly Thr Asn
            485                 490                 495

Ser Val Ile Val Lys Glu Pro Tyr Asn Pro Thr Val Thr Thr Thr Glu
        500                 505                 510

Phe Trp Ser Glu Ser Phe Ala Ser Thr Thr Thr Val Thr Asn Pro Pro
        515                 520                 525

Asp Gly Thr Asn
    530

<210> SEQ ID NO 31
<211> LENGTH: 4
<212> TYPE: PRT
<213> ORGANISM: Artificial Sequence
<220> FEATURE:
<223> OTHER INFORMATION: ALS Consensus

<400> SEQUENCE: 31

Gly Asp Thr Phe
1

<210> SEQ ID NO 32
<211> LENGTH: 4
<212> TYPE: PRT
<213> ORGANISM: Artificial Sequence
<220> FEATURE:

<223> OTHER INFORMATION: ALS Consensus

<400> SEQUENCE: 32

Met Pro Cys Val
1

<210> SEQ ID NO 33
<211> LENGTH: 4
<212> TYPE: PRT
<213> ORGANISM: Artificial Sequence
<220> FEATURE:
<223> OTHER INFORMATION: ALS Consensus

<400> SEQUENCE: 33

Tyr Ala Thr Cys
1

<210> SEQ ID NO 34
<211> LENGTH: 5
<212> TYPE: PRT
<213> ORGANISM: Artificial Sequence
<220> FEATURE:
<223> OTHER INFORMATION: ALS Consensus

<400> SEQUENCE: 34

Phe Asn Val Gly Gly
1               5

<210> SEQ ID NO 35
<211> LENGTH: 5
<212> TYPE: PRT
<213> ORGANISM: Artificial Sequence
<220> FEATURE:
<223> OTHER INFORMATION: ALS Consensus

<400> SEQUENCE: 35

Asp Ser Lys Cys Phe
1               5

<210> SEQ ID NO 36
<211> LENGTH: 5
<212> TYPE: PRT
<213> ORGANISM: Artificial Sequence
<220> FEATURE:
<223> OTHER INFORMATION: ALS Consensus

<400> SEQUENCE: 36

Asn Thr Val Thr Phe
1               5

<210> SEQ ID NO 37
<211> LENGTH: 4
<212> TYPE: PRT
<213> ORGANISM: Artificial Sequence
<220> FEATURE:
<223> OTHER INFORMATION: ALS Consensus

<400> SEQUENCE: 37

Ile Asp Cys Ser
1

<210> SEQ ID NO 38
<211> LENGTH: 7
<212> TYPE: PRT
<213> ORGANISM: Artificial Sequence
<220> FEATURE:
<223> OTHER INFORMATION: ALS Consensus

```
<400> SEQUENCE: 38

Pro Ala Gly Tyr Arg Pro Phe
1               5

<210> SEQ ID NO 39
<211> LENGTH: 5
<212> TYPE: PRT
<213> ORGANISM: Artificial Sequence
<220> FEATURE:
<223> OTHER INFORMATION: ALS Consensus

<400> SEQUENCE: 39

Thr Thr Leu Pro Phe
1               5

<210> SEQ ID NO 40
<211> LENGTH: 6
<212> TYPE: PRT
<213> ORGANISM: Artificial Sequence
<220> FEATURE:
<223> OTHER INFORMATION: ALS Consensus

<400> SEQUENCE: 40

Pro Ile Pro Thr Thr Thr
1               5

<210> SEQ ID NO 41
<211> LENGTH: 4
<212> TYPE: PRT
<213> ORGANISM: Artificial Sequence
<220> FEATURE:
<223> OTHER INFORMATION: ALS Consensus

<400> SEQUENCE: 41

Thr Ala Thr Val
1

<210> SEQ ID NO 42
<211> LENGTH: 5
<212> TYPE: PRT
<213> ORGANISM: Artificial Sequence
<220> FEATURE:
<223> OTHER INFORMATION: ALS Consensus

<400> SEQUENCE: 42

Thr Val Thr Thr Thr
1               5

<210> SEQ ID NO 43
<211> LENGTH: 7
<212> TYPE: PRT
<213> ORGANISM: Artificial Sequence
<220> FEATURE:
<223> OTHER INFORMATION: ALS Consensus

<400> SEQUENCE: 43

Asn Pro Thr Val Thr Thr Thr
1               5
```